(12) United States Patent
Juhl et al.

(10) Patent No.: US 10,011,596 B2
(45) Date of Patent: Jul. 3, 2018

(54) 2-AMINO-3-FLUORO-3-(FLUOROMETHYL)-6-METHYL-6-PHENYL-3,4,5,6-TETRAHYDROPYRIDINES AS BACE1 INHIBITORS

(71) Applicant: H. Lundbeck A/S, Valby (DK)

(72) Inventors: Karsten Juhl, Valby (DK); Lena Tagmose, Valby (DK); Mauro Marigo, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/233,463

(22) Filed: Aug. 10, 2016

(65) Prior Publication Data
US 2017/0044151 A1 Feb. 16, 2017

(30) Foreign Application Priority Data
Aug. 12, 2015 (DK) .................... 2015 00465

(51) Int. Cl.
| | | |
|---|---|---|
| C07D 417/12 | (2006.01) |
| C07B 59/00 | (2006.01) |
| C07D 211/72 | (2006.01) |
| C07D 401/12 | (2006.01) |
| C07D 413/12 | (2006.01) |
| C07D 211/76 | (2006.01) |

(52) U.S. Cl.
CPC .......... *C07D 417/12* (2013.01); *C07B 59/002* (2013.01); *C07D 211/72* (2013.01); *C07D 211/76* (2013.01); *C07D 401/12* (2013.01); *C07D 413/12* (2013.01); *C07B 2200/05* (2013.01)

(58) Field of Classification Search
CPC .. C07D 417/12; C07D 211/72; C07D 401/12; C07D 413/12; C07B 59/002
USPC ................................... 514/255.05
See application file for complete search history.

(56) References Cited

U.S. PATENT DOCUMENTS

| | | | |
|---|---|---|---|
| 7,067,507 B2 | 6/2006 | Pully, Sr. et al. | |
| 8,338,413 B1 | 12/2012 | Rueeger | |
| 9,346,797 B1* | 5/2016 | Juhl ................ | C07D 417/12 |
| 9,353,084 B2* | 5/2016 | Juhl ................ | C07D 405/12 |
| 2011/0009395 A1 | 1/2011 | Audia et al. | |
| 2014/0371212 A1 | 12/2014 | Green et al. | |
| 2015/0232449 A1* | 8/2015 | Juhl ................ | C07D 401/12 514/255.05 |
| 2016/0130267 A1* | 5/2016 | Juhl ................ | C07D 417/12 514/255.05 |
| 2017/0042895 A1 | 2/2017 | Juhl et al. | |
| 2017/0066741 A1 | 3/2017 | Juhl et al. | |
| 2017/0313658 A1 | 11/2017 | Juhl et al. | |
| 2017/0319564 A1 | 11/2017 | Juhl et al. | |
| 2017/0340618 A1 | 11/2017 | Juhl et al. | |

FOREIGN PATENT DOCUMENTS

| | | |
|---|---|---|
| EP | 2703399 | 3/2014 |
| WO | WO 03/032970 | 4/2003 |
| WO | WO 03/068747 | 8/2003 |
| WO | WO 2011/154431 | 12/2011 |
| WO | WO 2012/095463 | 7/2012 |
| WO | WO 2012/095469 | 7/2012 |
| WO | WO 2012/139993 | 10/2012 |
| WO | WO 2012/168164 | 12/2012 |
| WO | WO 2013/027188 | 2/2013 |
| WO | WO 2013/142613 | 9/2013 |
| WO | WO 2014/056816 | 4/2014 |
| WO | WO 2014/065434 | 5/2014 |
| WO | WO 2014/134341 | 9/2014 |
| WO | WO 2015/124576 | 8/2015 |
| WO | WO 2015/156421 | 10/2015 |
| WO | WO 2016075062 | * 5/2016 |
| WO | WO 2016075063 | * 5/2016 |
| WO | WO 2016075064 | * 5/2016 |

OTHER PUBLICATIONS

Munro; JSM Alzheimer's Dis Related Dementia 2014, 1, 1005.*
Scott; J. Med. Chem., 2016, 59, 10435-10450.*
Vassar; Alzheimers Research and Therapy 2014, 6, 89.*
Webb; Current Gerontology and Geriatrics Research, vol. 2012, Article ID 362839, 8 pages, 2012.*
Biffi; J Clin Neurol 2011, 7, 1-9.*
Dubois; Lancet Neurol 2007, 6, 734-746.*
"Understanding Genetics and Alzheimers Disease", Aug. 2014, Alzheimer Society, Toronto, Canada, pp. 1-4.*
Asuni, A., et al. (2007) "Immunotherapy Targeting Pathological Tau Conformers in a Tangle Mouse Model Reduces Brain Pathology with Associated Functional Improvements," J. Neurosci. 27:9115-9129.
Berge, S.M., et al. (1977) "Pharmaceutical Salts," J. Pharma. Sci. 66:1-19.
Boutajangout, A. et al. (2010) "Immunotherapy Targeting Pathological Tau Prevents Cognitive Decline in a New Tangle Mouse Model," J. Neurosci. 30(49):16559-16566.

(Continued)

*Primary Examiner* — Daniel R Carcanague
(74) *Attorney, Agent, or Firm* — Wolf, Greenfield & Sacks, P.C.

(57) ABSTRACT

The present invention provides compounds of Formula I

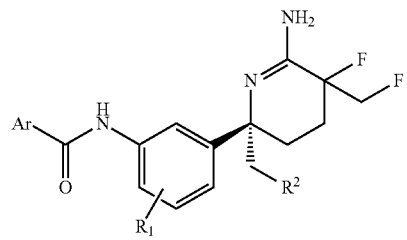

[I]

for the treatment of neurodegenerative or cognitive diseases. The method further provides for piperidine-2-one and piperidine-2-thione intermediates to compounds of formula I.

31 Claims, No Drawings

(56) References Cited

OTHER PUBLICATIONS

Boutajangout, A., et al. (2011) "Targeting Hyperphosphorylated Tau Protein with a Monoclonal Antibody at an Advanced Stage of Tau Pathology Improves Cognition in a Mouse Model," 7(4,suppl):S480-S481.
Ginman, T., et al. (2013) "Core Refinement Toward Permeable β-Secretase (BACE1) Inhibitors with Low hERG Activity," J. Med. Chem. 56:4181-4205.
Hamada, Y., et al. (2009) "Recent Progress in the Drug Discovery on Non-Peptidic BACE1 Inhibitors," Expert Opinion on Drug Disc. 4(4):391-416.
Hampel, H., et al. (2009) "Beta-site Amyloid Precursor Protein Cleaving Enzyme 1 (BACE1) as a Biological Candidate Marker of Alzheimer's Disease," The Scandinavian J. Clin. Lab. Invest. 69(1):8-12.
Hilpert, H., et al. (2013) "S1 Supporting Information β-Secretase (BACE1) Inhibitors with High In Vivo Efficacy Suitable for Clinical Evaluation in Alzheimer's Disease," 56:S1-S44.
Hilpert H., et al. (2013) "β-Secretase (BACE1) Inhibitors with High In Vivo Efficacy Suitable for Clinical Evaluation in Alzheimer's Disease," J. Medicinal Chem. 56(10):3980-3995.
International Search Report PCT/EP2015/053327 (WO 2015/124576) (2015) (5 pages).
International Search Report PCT/EP2015/076017 (WO 2016/075064) (2016) (5 pages).
Jacobsen, H., et al. (2014) "Combined Treatment with a BACE Inhibitor and Anti-Aβ Antibody Gantenerumab Enhances Amyloid Reduction in APPLondon Mice," J. Neurosci. 34(35):11621-11630.
Jeon, S.Y., et al. (2003) "Green Tea Catechins as a BACE1 (β-Secretase) Inhibitor," Bioorganic & Medicinal Chem. Lett. 13:3905-3908.
Jeppsson, F., et al. (2012) "Discovery of AZD3839, a Potent and Selective BACE1 Inhibitor Clinical Candidate for the Treatment of Alzheimer Disease," J. Biol. Chem. 287(49):41245-41257.
Kumar, A., et al. (2015) "A Review on Alzheimer's Disease Pathophysiology and Its Management: An Update," Pharmacol. Reporting 67:195-203.
Malamas, M., et al. (2010) "Novel Pyrrolyl 2-Aminopyridines as Potent and Selective Human β-Secretase (BACE1) Inhibitors," Bioorganic & Medicinal Chem. Lett. 20:2068-2073.
Melis, V., et al. (2015) "Effects of Oxidized and Reduced Forms of Methylthioninium in Two Transgenic Mouse Tauopathy Models," Behav. Pharmacol. 26:353-368.
Oehlrich, D., et al. (2014) "The Evolution of Amidine-Based Brain Penetrant BACE1 Inhibitors," Bioorganic & Medicinal Chem. Lett. 24(9):2033-2045.
Ohno, M. et al.(2004) "BACE1 Deficiency Rescues Memory Deficits and Cholinergic Dysfunction in a Mouse Model of Alzheimer's Disease," Neuron 41:27-33.
Ohno, M., et al. (2007) "BACE1 Gene Deletion Prevents Neuron Loss and Memory Deificits in 5XFAD APP/PS1 Transgenic Mice," Neurobiology of Disease 26:134-145.
Probst, G., et al. (2012): Small-Molecule BACE1 Inhibitors: A Patent Literature Review (2006-2011), Expert Opinion on Thera. Patents 22(5):511-540.
Sheline, Y.I., et al. (2014) "An Antidepressant Decreases CSF AβProduction in Healthy Individuals and in Transgenic AD Mice," Sci. Transl. Med. 6(236):236re4; pp. 1-10.
Willem, M., et al. (2009) "Function, Regulation and Therapeutic Properties of β-Secretase (BACE1)," Seminars in Cell & Developmental Biol. 20:175-182.
Woltering, T.J., et al. (2013) "BACE1 Inhibitors: A Head Group Scan on a Series of Amides," Bioorganic & Medicinal Chem. Lett. 23:4239-4243.
Written Opinion of the International Searching Authority PCT/EP2015/053327 (WO 2015/124576) (2015) (6 pages).
Bermejo-Bescós, P. et al. (2013) "*Processing of the Platelet Amyloid Precursor Protein in the Mild Cognitive Impairment (MCI)*," Neurochem. Res. 38(7):1415-1423.
Cheng, H. et al. (2014) "*Occludin Deficiency With BACE1 Elevation in Cerebral Amyloid Angiopathy*," Neurology 82(19):1707-1715.
Cheng, X. et al. (2014) "*High Activities of BACE1 in Brains With Mild Cognitive Impairment*," Am. J. Pathol. 184(1):141-147.
Holler, C.J. et al. (2012) "*BACE2 Expression Increases in Human Neurodegenerative Disease*," Amer. J. Pathol. 180(1):337-350.
Jiang, H. et al. (2011) "*Elevated CSF Levels of TACE Activity and Soluble TNF Receptors in Subjects With Mild Cognitive Impairment and Patients With Alzheimer's Disease*," Mol. Neurodegener. 6:69.
Jiang, Y. et al. (2010) "*Alzheimer's-Related Endosome Dysfunction in Down Syndrome Is Abeta-Independent But Requires APP and Is Reversed by BACE-1 Inhibition*," Proc. Natl. Acad. Sci. (U.S.A.) 107(4):1630-1635.
Jiang, Y. et al. (2016) "*Partial BACE1 Reduction in a Down Syndrome Mouse Model Blocks Alzheimer-Related Endosomal Anomalies and Cholinergic Neurodegeneration: Role of APP-CTF*," Neurobiol. Aging 39:90-98.
Miners, J.S. et al. (2011) "*Accumulation of Insoluble Amyloid-β in Down's Syndrome Is Associated With Increased BACE-1 and Neprilysin Activities*," J Alzheimers Dis. 23(1):101-108.
Motonaga, K. et al. (2002) "*Elevated Expression of Beta-Site Amyloid Precursor Protein Cleaving Enzyme 2 in Brains of Patients With Down Syndrome*," Neurosci. Lett. 21;326(1):64-66.
Salminen, A. et al. (2017) "*Hypoxia/Ischemia Activate Processing Of Amyloid Precursor Protein: Impact of Vascular Dysfunction in the Pathogenesis Of Alzheimer's Disease*," J. Neurochem. 140(4):536-549.
Sun, X. et al. (2006) "*Increased BACE1 Maturation Contributes to the Pathogenesis Of Alzheimer's Disease in Down Syndrome*," FASEB J. 20(9):1361-1368.
Thakker, D.R. et al. (2015) "*Centrally Delivered BACE1 Inhibitor Activates Microglia, and Reverses Amyloid Pathology and Cognitive Deficit in Aged Tg2576 Mice*," J. Neurosci. 35(17):6931-6936.
Wang. T. et al. (2016) "*Abnormal Changes of Brain Cortical Anatomy and the Association with Plasma MicroRNA107 Level in Amnestic Mild Cognitive Impairment*," Front. Aging Neurosci. 8:112.
Willem, M. et al. (2004) "*Beta-Site Amyloid Precursor Protein Cleaving Enzyme 1 Increases Amyloid Deposition in Brain Parenchyma But Reduces Cerebrovascular Amyloid Angiopathy in Aging BACE X APP[V717I] Double-Transgenic Mice*," Am. J. Pathol. 165(5):1621-1631.
Xue, Z.Q. et al. (2015) "*Non-Neuronal and Neuronal BACE1 Elevation in Association With Angiopathic and Leptomeningeal β-Amyloid Deposition in the Human Brain*," BMC Neurol. 15:71.
Zetterberg, H. et al. (2008) "*Elevated Cerebrospinal Fluid BACE1 Activity in Incipient Alzheimer Disease*," Arch. Neurol. 65(8):1102-1107.
Zhang, X. et al. (2015) "Upregulation of SET expression by BACE1 and its implications in Down syndrome," Mol. Neurobiol. 51(2):781-790.
Zhong, Z. et al. (2007) "*Levels of Beta-Secretase (BACE1) in Cerebrospinal Fluid As a Predictor of Risk in Mild Cognitive Impairment*," Arch. Gen. Psychiatry 64(6):718-726.
Bakker, A., et al. (2012) "Reduction of Hippocampal Hyperactivity Improves Cognition in Amnestic Mild Cognitive Impairment," Neuron 74(3):467-474.
Bohm, C. et al. (2015) "Current and Future Implications of Basic and Translational Research on Amyloid-β Peptide Production and Removal Pathways," Mol. Cell. Neurosci. 66:3-11.
Butchart, J., et al. (2015) "Etanercept in Alzheimer Disease: A Randomized, Placebo-Controlled, Double-Blind, Phase 2 Trial," Neurol. 84(21):2161-2168.
Davtyan, H., et al. (2013) "Immunogenicity, Efficacy, Safety, and Mechanism of Action of Epitope Vaccine (Lu AF20513) for Alzheimer's Disease: Prelude to a Clinical Trial," J. Neurosci. 33(11):4923-4934.
DeMattos, R.B., et al. (2015) "Investigation of Dose-Responses and Longitudinal Effects of Combination Therapy with a Plaque-Specific Amyloid Beta Antibody and BACE Inhibitor in Aged Transgenic Mice," Alzheimer's & Dementia: J. Alzheimer's Assoc. 11(7 suppl):275-276.

(56) References Cited

OTHER PUBLICATIONS

Hartley, D., et al. (2015) "Down Syndrome and Alzheimer's Disease: Common Pathways, Common Goals," Alzheimer's & Dementia 11:700-709.
Heneka, M.T., et al.(2015) "Neuroinflammation in Alzheimer's Disease," Lancet Neurol. 14(4):388-405.
International Search Report PCT/EP2015/076014 (WO 2016/075062) (2015) (4 pages).
International Search Report PCT/EP2015/076015 (WO 2016/075063) (2016) (5 pages).
Koh, M.T., et al. (2010) "Treatment Strategies Targeting Excess Hippocampal Activity Benefit Aged Rates with Cognitive Impairment," Neuropsychopharmacol. 35:1016-1025.
Shi, J.Q., et al. (2013) "Antiepileptics Topiramate and Levetiracetam Alleviate Behavioral Deficits and Reduce Neuropathology in APPswe/PS1dE9 Transgenic Mice," CNS Neurosci. Ther. 19(11):871-881.
Vossel, K.A. , et al. (2013) "Seizures and Epileptiform Activity in the Early Stages of Alzheimer Disease," Jama Neurol. 70(9):1158-1166.
Wang, J., et al. (2015) "Anti-inflammatory Drugs and Risk of Alzheimer's Disease: An Updated Systematic Review and Meta-Analysis," J. Alzheimers Dis. 44(2):385-396.
Written Opinion of the International Searching Authority PCT/EP2015/076014 (WO 2016/075062) (2015) (5 pages).
Written Opinion of the International Searching Authority PCT/EP2015/076015 (WO 2016/075063) (4 pages).
Written Opinion of the International Searching Authority PCT/EP2015/076017 (WO 2016/075064) (4 pages).
Zaitsev, A.V., et al. (2015) "N-methyl-D-aspartate Receptor Channel Blockers Prevent Pentylenetetrazole-Induced Convulsions and Morphological Changes in Rat Brain Neurons," J. Neurosci. Res. 93(3):454-465.
International Search Report and Written Opinion dated Sep. 12, 2016 in connection with PCT/EP2016/069029.
International Search Report and Writte Opinion dated Oct. 18, 2016 in connection with PCT/EP2016/068947.

* cited by examiner

2-AMINO-3-FLUORO-3-(FLUOROMETHYL)-6-METHYL-6-PHENYL-3,4,5,6-TETRAHYDROPYRIDINES AS BACE1 INHIBITORS

FIELD OF THE INVENTION

The present invention provides compounds which are BACE1 inhibitors. Separate aspects of the invention are directed to pharmaceutical compositions comprising said compounds and uses of the compounds to treat neurodegenerative and cognitive disorders.

BACKGROUND ART

Dementia is a clinical syndrome characterized by deficits in multiple areas of cognition that cannot be explained by normal aging, a noticeable decline in function, and an absence of delirium. In addition, neuropsychiatric symptoms and focal neurological findings are usually present. Dementia is further classified based on etiology. Alzheimer's disease (AD) is the most common cause of dementia, followed by mixed AD and vascular dementia, Lewy body dementia (DLB), and fronto-temporal dementia.

β-Amyloid deposits and neurofibrillary tangles are considered to be major pathologic characterizations associated with AD which is characterized by the loss of memory, cognition, reasoning, judgment, and orientation. Also affected, as the disease progresses, are motor, sensory and linguistic abilities until global impairment of multiple cognitive functions occurs. β-Amyloid deposits are predominantly an aggregate of Aβ peptide, which in turn is a product of the proteolysis of amyloid precursor protein (APP) as part of the β-amyloidogenic pathway. Aβ peptide results from the cleavage of APP at the C-terminals by one or more γ-secretases and at the N-terminus by β-secretase 1 (BACE1) also known as aspartyl protease 2. BACE1 activity is correlated directly to the generation of Aβ peptide from APP. Studies indicate that the inhibition of BACE1 impedes the production of Aβ peptide. Further, BACE1 co-localizes with its substrate APP in Golgi and endocytic compartments (Willem M, et al. *Semin. Cell Dev. Biol,* 2009, 20, 175-182). Knock-out studies in mice have demonstrated the absence of amyloid peptide formation while the animals are healthy and fertile (Ohno M, et al. *Neurobiol. Dis.,* 2007, 26, 134-145). Genetic ablation of BACE1 in APP-overexpressing mice has demonstrated absence of plaque formation, and the reversal of cognitive deficits (Ohno M, et al. *Neuron;* 2004, 41, 27-33). BACE1 levels are elevated in the brains of sporadic AD patients (Hempel and Shen, *Scand. J. Clin. Lab. Invest.* 2009, 69, 8-12).

These convergent findings indicate that the inhibition of BACE1 may be a therapeutic target for the treatment of AD as well as neurodegenerative or cognitive disorders for which the reduction of Aβ deposits is beneficial.

AstraZeneca announced the discovery of AZD3839, a potent BACE1 inhibitor clinical candidate for the treatment of AD (Jeppsson, F., et al. *J. Biol. Chem.,* 2012, 287, 41245-41257) in October 2012. The effort which led to the discovery of AZD3839 was further described in Ginman, T., et al. *J. Med. Chem.,* 2013, 56, 4181-4205.

The Ginman publication describes the issues which were overcome in connection with the discovery and identification of AZD3839. These issues related to poor blood brain barrier penetration and P-glycoprotein mediated efflux of the compounds resulting in lack of brain exposure.

The Ginman manuscript hypothesized that the differences in brain exposure would largely be due to the core structures and Structure Activity Relationship data was provided wherein the in vitro properties on the reported compounds were given in four tables according to core sub-types. In Table 6, a series of amidine containing compounds are described that were considered interesting from an activity perspective. However, the data suggests that the amidine containing core did not exhibit a favourable blood brain barrier permeability profile.

Researchers from Hoffmann-La Roche and Siena Biotech also reported the discovery of amidine containing compounds (Woltering, T. J., et al. *Bioorg. Med. Chem. Lett.* 2013, 23, 4239-4243). These compounds (compounds 17 and 18 in the paper) were found not to have any in vivo effect (lack of Aβ40 reduction in brain in wild type mice).

Contrary to the teachings of Ginman, et al. and Woltering, T. J., et al., the present inventors have discovered a series of amidine compounds which are brain penetrating. Accordingly, the present invention relates to novel compounds having BACE1 inhibitory activity, to their preparation, to their medical use and to medicaments comprising them.

SUMMARY OF THE INVENTION

An objective of the present invention is to provide compounds that inhibit BACE1.

Accordingly, the present invention relates to compounds of Formula I.

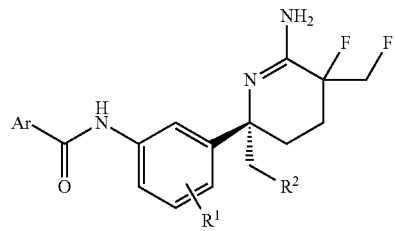

Formula I wherein Ar is selected from the group consisting of phenyl, pyridyl, pyrimidyl, pyrazinyl, imidazolyl, pyrazolyl, thiazolyl, oxazolyl, isoxazolyl, and where Ar is optionally substituted with one or more substituents selected from halogen, CN, $C_1$-$C_6$ alkyl, $C_2$-$C_6$ alkenyl, $C_2$-$C_6$ alkynyl, $C_1$-$C_6$ fluoroalkyl or $C_1$-$C_6$ alkoxy; and $R^1$ is one or more hydrogen, halogen, $C_1$-$C_3$ fluoroalkyl or $C_1$-$C_3$ alkyl;

$R^2$ is hydrogen or fluoro or a pharmaceutically acceptable salt thereof.

In one embodiment the present invention provides compounds of Formula I or a pharmaceutically acceptable salt thereof for use in therapy.

The present invention further provides a pharmaceutical composition comprising a compound of Formula I or a pharmaceutically acceptable salt thereof and a pharmaceutically acceptable carrier.

In one embodiment the invention provides the use of a compound of Formula I or a pharmaceutically acceptable salt thereof in the manufacture of a medicament for the treatment of neurodegenerative or cognitive disorder.

In one embodiment, the invention provides a compound of Formula I or a pharmaceutically acceptable salt thereof for use in a method for the treatment of a neurodegenerative or cognitive disorder.

The present invention provides a method of treating a neurodegenerative or cognitive disorder comprising administering a therapeutically effective amount of a compound of Formula I or a pharmaceutically acceptable salt thereof to a patient in need thereof.

DETAILED DESCRIPTION OF THE INVENTION

One embodiment the present invention provides compounds of Formula Ia or Ib

[Ia]

[Ib]

In one embodiment $R^1$ is halogen, and in particularly $R^1$ is fluoro.
In one embodiment $R^2$ is hydrogen.
In one embodiment $R^2$ is fluoro.
In one embodiment Ar is pyridyl.
In one embodiment Ar is pyrimidyl.
In one embodiment Ar is pyrazinyl.
In one embodiment Ar is oxazolyl.
In one embodiment Ar is imidazolyl.
In one embodiment Ar is thiazolyl.
In one embodiment Ar is pyrazolyl.
In one embodiment Ar is isoxazolyl
In one embodiment Ar is phenyl.
In one embodiment, Ar is substituted by one or more substituents selected from the group consisting of F, Cl, Br, CN, $C_1$-$C_3$ alkyl, $C_1$-$C_3$ haloalkyl or $C_1$-$C_3$ alkoxy.
In one embodiment, a compound of the present invention is selected from the group consisting of:
N-(3-((2S,5S)-6-amino-5-fluoro-5-(fluoromethyl)-2-methyl-2,3,4,5-tetrahydropyridin-2-yl)-4-fluorophenyl)-5-methoxypicolinamide;
N-(3-((2S,5S)-6-amino-5-fluoro-5-(fluoromethyl)-2-methyl-2,3,4,5-tetrahydropyridin-2-yl)-4-fluorophenyl)-5-(methoxy-d3)picolinamide;
N-(3-((2S,5S)-6-amino-5-fluoro-5-(fluoromethyl)-2-methyl-2,3,4,5-tetrahydropyridin-2-yl)-4-fluorophenyl)-5-cyano-3-methylpicolinamide;
N-(3-((2S,5S)-6-amino-5-fluoro-5-(fluoromethyl)-2-methyl-2,3,4,5-tetrahydropyridin-2-yl)-4-fluorophenyl)-5-methoxypyrazine-2-carboxamide;
N-(3-((2S,5S)-6-amino-5-fluoro-5-(fluoromethyl)-2-methyl-2,3,4,5-tetrahydropyridin-2-yl)-4-fluorophenyl)-2-methyloxazole-4-carboxamide;
N-(3-((2S,5S)-6-amino-5-fluoro-5-(fluoromethyl)-2-methyl-2,3,4,5-tetrahydropyridin-2-yl)-4-fluorophenyl)-4-bromo-1-methyl-1H-imidazole-2-carboxamide;
N-(3-((2S,5S)-6-amino-5-fluoro-5-(fluoromethyl)-2-methyl-2,3,4,5-tetrahydropyridin-2-yl)-4-fluorophenyl)-4-methylthiazole-2-carboxamide;
N-(3-((2S,5S)-6-amino-5-fluoro-5-(fluoromethyl)-2-methyl-2,3,4,5-tetrahydropyridin-2-yl)-4-fluorophenyl)-2-(difluoromethypoxazole-4-carboxamide;
N-(3-((2S,5S)-6-amino-5-fluoro-5-(fluoromethyl)-2-methyl-2,3,4,5-tetrahydropyridin-2-yl)-4-fluorophenyl)-1-(difluoromethyl)-1H-pyrazole-3-carboxamide;
N-(3-((2S,5S)-6-amino-5-fluoro-5-(fluoromethyl)-2-methyl-2,3,4,5-tetrahydropyridin-2-yl)-4-fluorophenyl)-5-(difluoromethyl)pyrazine-2-carboxamide;
N-(3-((2S,5S)-6-amino-5-fluoro-5-(fluoromethyl)-2-methyl-2,3,4,5-tetrahydropyridin-2-yl)-4-fluorophenyl)-4-chlorobenzamide;
N-(3-((2S,5S)-6-amino-5-fluoro-5-(fluoromethyl)-2-methyl-2,3,4,5-tetrahydropyridin-2-yl)-4-fluorophenyl)-5-fluoropicolinamide;
N-(3-((2S,5R)-6-amino-5-fluoro-5-(fluoromethyl)-2-methyl-2,3,4,5-tetrahydropyridin-2-yl)-4-fluorophenyl)-5-methoxypicolinamide;
N-[3-[(2S,5S)-6-amino-5-fluoro-5-(fluoromethyl)-2-methyl-2,3,4,5-tetrahydropyridin-2-yl]-4,5-difluoro-phenyl]-5-fluoro-pyridine-2-carboxamide;
N-[3-[(2S,5S)-6-amino-5-fluoro-5-(fluoromethyl)-2-methyl-2,3,4,5-tetrahydropyridin-2-yl]-4,5-difluoro-phenyl]-5-methoxy-pyridine-2-carboxamide;
N-[3-[(2S,5S)-6-amino-5-fluoro-5-(fluoromethyl)-2-methyl-2,3,4,5-tetrahydropyridin-2-yl]-4,5-difluoro-phenyl]-5-methoxy-pyrazine-2-carboxamide:
N-[3-[(2S,5R)-6-amino-5-fluoro-5-(fluoromethyl)-2-methyl-2,3,4,5-tetrahydropyridin-2-yl]-4,5-difluoro-phenyl]-5-fluoro-pyridine-2-carboxamide;
N-[3-[(2S,5R)-6-amino-5-fluoro-5-(fluoromethyl)-2-methyl-2,3,4,5-tetrahydropyridin-2-yl]-4,5-difluoro-phenyl]-5-methoxy-pyridine-2-carboxamide:
N-[3-[(2S,5R)-6-amino-5-fluoro-5-(fluoromethyl)-2-methyl-2,3,4,5-dihydropyridin-2-yl]-4,5-difluoro-phenyl]-5-methoxy-pyrazine-2-carboxamide:
N-[3-[(2S,5S)-6-amino-5-fluoro-2,5-bis(fluoromethyl)-2,3,4,5-tetrahydropyridin-2-yl]-4-fluoro-phenyl]-5-fluoro-pyridine-2-carboxamide;
N-[3-[(2S,5S)-6-amino-5-fluoro-2,5-bis(fluoromethyl)-2,3,4,5-tetrahydropyridin-2-yl]-4-fluoro-phenyl]-5-methoxy-pyridine-2-carboxamide;
N-[3-[(2S,5S)-6-amino-5-fluoro-2,5-bis(fluoromethyl)-2,3,4,5-tetrahydropyridin-2-yl]-4-fluoro-phenyl]-5-methoxy-pyridine-2-carboxamide;
N-[3-[(2S,5R)-6-amino-5-fluoro-2,5-bis(fluoromethyl)-2,3,4,5-tetrahydropyridin-2-yl]-4-fluoro-phenyl]-5-fluoro-pyridine-2-carboxamide;
N-[3-[(2S,5R)-6-amino-5-fluoro-2,5-bis(fluoromethyl)-2,3,4,5-tetrahydropyridin-2-yl]-4-fluoro-phenyl]-5-methoxy-pyridine-2-carboxamide and
N-[3-[(2S,5R)-6-amino-5-fluoro-2,5-bis(fluoromethyl)-2,3,4,5-tetrahydropyridin-2-yl]-4-fluoro-phenyl]-5-methoxy-pyrazine-2-carboxamide;
or a pharmaceutically acceptable salt thereof.

As used herein, the term "$C_1$-$C_6$ alkyl" refers to a straight chained or branched saturated hydrocarbon having from one to six carbon atoms inclusive. Examples of $C_1$-$C_6$ alkyl include, but are not limited to, methyl, ethyl, 1-propyl, 2-propyl, 1-butyl, 2-butyl, 2-methyl-2-propyl, 2-methyl-1-propyl, n-pentyl and n-hexyl. Similarly, the term "$C_1$-$C_3$ alkyl" refers to a straight chained or branched saturated hydrocarbon having from one to three carbon atoms inclusive. Examples of such substituents include, but are not limited to, methyl, ethyl and n-propyl.

Likewise, the term "$C_1$-$C_6$ alkoxy" refers to a straight chained or branched saturated alkoxy group having from one to six carbon atoms inclusive with the open valency on the oxygen. Examples of $C_1$-$C_6$ alkoxy include, but are not limited to, methoxy, ethoxy, n-butoxy, t-butoxy and n-hexyloxy. The "$C_1$-$C_6$ alkoxy" is optionally substituted with one or more fluorine atoms.

As used herein, the term "$C_1$-$C_6$ fluoroalkyl" refers to a straight chained or branched saturated hydrocarbon having from one to six carbon atoms inclusive substituted with one or more fluorine atoms. Examples of $C_1$-$C_6$ fluoroalkyl include, but are not limited to, trifluoromethyl, pentafluoroethyl, 1-fluoroethyl, monofluoromethyl, difluoromethyl, 1,2-difluoroethyl and 3,4 difluorohexyl. Similarly, the term "$C_1$-$C_3$ fluoroalkyl" refers to a straight chained or branched saturated hydrocarbon having from one to three carbon atoms inclusive substituted with one or more fluorine atoms per carbon atom.

The term "halogen" refers to fluoro, chloro, bromo and iodo.

The term "$C_2$-$C_6$ alkenyl" refers to a branched or unbranched alkenyl group having from two to six carbon atoms and one double bond, including but not limited to ethenyl, propenyl, and butenyl.

The term "$C_2$-$C_6$ alkynyl" shall mean a branched or unbranched alkynyl group having from two to six carbon atoms and one triple bond, including but not limited to ethynyl, propynyl and butynyl.

The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

The term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

The present invention is based on the discovery that compounds of Formula I are inhibitors of BACE1, and as such, are useful for the treatment of disorders which pathological characteristics comprise β-amyloid deposits and neurofibrillary tangles, such as neurodegenerative or cognitive disorders.

The compounds of the present invention are, as discussed above, expected to be useful in the treatment of Alzheimer's disease due to their effects on β-amyloid deposits and neurofibrillary tangles. This includes familial Alzheimer's disease where patients carry mutations on specific genes intimately involved in the production of Aβ peptide. It is, however, important to note that aggregates of Aβ peptide is not limited to familial Alzheimer's disease but is similarly an important pathophysiological characteristics of the more common sporadic Alzheimer's disease [*Mol Cell Neurosci*, 66, 3-11, 2015].

The compounds of the present invention are also believed to be useful in the treatment of early-stage Alzheimer's disease, i.e. disease stages where the biological and structural changes have started but the clinical manifestations of the disease have not yet become evident or are not yet well developed. Early-stage Alzheimer's disease may, in fact, start years before any clinical manifestation of the disease becomes manifest. Early-stage Alzheimer's disease includes prodromal Alzheimer's disease, preclinical Alzheimer's disease and mild cognitive impairment. Although mild cognitive impairment may be unrelated to Alzheimer's disease it is often a transitional stage to Alzheimer's disease or due to Alzheimer's disease. Preclinical and prodromal Alzheimer's disease are asymptomatic stages, and they are typically diagnosed by the presence of Alzheimer's disease related biomarkers. In this context the compounds of the present invention are believed to be useful in slowing down the progression of early-stage Alzheimer's disease, such as mild cognitive impairment to Alzheimer's disease. The compounds of the present invention are also believed to be useful in the treatment of memory loss, attention deficits and dementia associated with Alzheimer's disease.

Other diseases, in addition to the continuum of Alzheimer's disease, are characterized by β-amyloid deposits and neurofibrillary tangles. This includes e.g. Trisomy 21 also known as Down's syndrome. Patients suffering from Down's syndrome have an extra chromosome 21 which chromosome contains the gene for the amyloid precursor protein (APP). The extra chromosome 21 leads to overexpression of APP, which leads to increased levels of Aβ peptide, which eventually causes the markedly increased risk of developing Alzheimer's disease seen in Down's syndrome patients [*Alzheimer's & Dementia*, 11, 700-709, 201]. Cerebral amyloid angiopathy is also characterized by β-amyloid deposits and neurofibrillary tangles in blood vessels of the central nervous system [*Pharmacol Reports*, 67, 195-203, 2015] and is as such expected to be treatable with compounds of the present invention.

In one embodiment, the present invention provides a method of treating a disease selected from Alzheimer's disease (familial or sporadic), preclinical Alzheimer's disease, prodromal Alzheimer's disease, mild cognitive impairment, Down's syndrome and cerebral amyloid angiopathy, the method comprising the administration of a therapeutically effective amount of a compound of Formula I or a pharmaceutically acceptable salt thereof to a patient in need thereof. The compounds of the invention are believed to be useful in the treatment of a disease is selected from Alzheimer's disease (familial or sporadic), preclinical Alzheimer's disease, prodromal Alzheimer's disease and mild cognitive impairment.

The present invention further provides a method of inhibiting BACE1 in a patient comprising administering to a patient in need thereof a therapeutically effective amount of a compound of Formula I or a pharmaceutically acceptable salt thereof.

The present invention also provides a method of inhibiting β-secretase mediated cleavage of amyloid precursor protein comprising administering to a patient in need of such treatment a therapeutically effective amount a compound of Formula I or a pharmaceutically acceptable salt thereof.

In further embodiments, the present invention provides the use of a compound of Formula I or a pharmaceutically acceptable salt thereof for the manufacture of a medicament for the treatment of a disease selected from Alzheimer's disease (familial or sporadic), preclinical Alzheimer's disease, prodromal Alzheimer's disease, mild cognitive impairment, Down's syndrome or cerebral amyloid angiopathy.

The present invention also provides the use of a compound of Formula I or a pharmaceutically acceptable salt thereof for the manufacture of a medicament for the inhibition of BACE1. The present invention further provides the use of a compound of Formula I or a pharmaceutically acceptable salt thereof for the manufacture of a medicament for the inhibition of production or accumulation of Aβ peptide.

In one embodiment, the present invention provides a compound of Formula I or a pharmaceutically acceptable salt thereof for use in a method for the treatment of a disease selected form Alzheimer's disease (familial or sporadic), preclinical Alzheimer's disease, prodromal Alzheimer's disease, mild cognitive impairment, Down's syndrome or cerebral amyloid angiopathy.

In one embodiment, the present invention relates to a compound of Formula I or a pharmaceutically acceptable salt thereof for use in a method for inhibiting of BACE1 or in a method for inhibiting of production or accumulation of Aβ peptide.

The compounds of the present invention are as demonstrated in the examples potent inhibitors of BACE1 and capable of lowering the level of Aβ peptide in rat brain and plasma, and said compounds are thus believed to be useful in the treatment of neurodegenerative and cognitive disorders which pathological characteristics comprise Aβ deposits and neurofibrilary tangles, such as e.g. Alzheimer's disease. It may be beneficial to combine a compound of the present invention with another treatment paradigm useful in the treatment of such disease, e.g. Alzheimer's disease.

Tau proteins are abundant in neurons. Tau proteins are soluble, highly phosphorylation labile and bind to tubulin providing regulation and modulation of tubulin assembly, i.e. eventually the microtubular structure and stability. Tau proteins can only associate with tubulin in the most de-phosphorylated state, and phosphorylation/de-phosphorylation acts as a switch controlling the tubulin association. Phosphorylated Tau constitutes an important part of the neurofibrillary tangles which are one of the hallmarks of Alzheimer's disease. The so-called Tau hypothesis suggests targeting these pathological tangles, a main constituent of which is phosphorylated Tau protein, as a treatment paradigm for Alzheimer's disease. In particular, immunotherapies, both active and passive, have been suggested as a way to target Tau neurofibrillary tangles. In active immunotherapy, a pathogenic antigen is injected into the patient and the innate immune system elicits an immune response. This triggers the maturation of B-cells generating high affinity antibodies against the administered antigen. In a passive immunotherapy, the triggering of the innate immune system is circumvented by infusing a specific antibody against the antigen. It is suggested that the inherent clearance system then removes antibody bound ligand. Substantial evidence for the efficacy of both active and passive immunotherapy targeting phosphorylated Tau protein as a treatment for Alzheimer's disease exists [*Alzheimer's & Dementia*, 7(4, suppl) S480-481; *J Neurosci* 30, 16559-16556, 2010; *J Neurosci*, 27, 9115-9129, 2007].

In one embodiment the invention provides a method for the treatment of a neurodegenerative or cognitive disorder, e.g. Alzheimer's disease, the method comprising the administration of a therapeutically effect amount of two components (1) a compound of Formula I or a pharmaceutically acceptable salt thereof and (2) a compound useful in active or passive Tau immunotherapy to a patient in need thereof. Said compound useful in passive Tau immunotherapy may be an antibody directed against phosphorylated Tau protein. Said compound useful in active Tau immunotherapy may be a fragment of the Tau protein amino acid sequence which upon injection in a patient elicits antibodies against phosphorylated Tau protein in said patient. The administration according to this embodiment of the invention may be simultaneous, or there may be a time gap between the administration of the two components.

In one embodiment, the invention relates to the use of a compound of Formula I or a pharmaceutically acceptable salt thereof and a compound useful in active or passive Tau immunotherapy in the manufacture of a medicament for the treatment of neurodegenerative or cognitive disorder, e.g. Alzheimer's disease.

In one embodiment, the invention provides a compound of Formula I or a pharmaceutically acceptable salt thereof and a compound useful in active or passive Tau immunotherapy for use in a method for the treatment of a neurodegenerative or cognitive disorder, e.g. Alzheimer's disease.

In one embodiment, the invention provides a pharmaceutical composition comprising a compound of Formula I or a pharmaceutically acceptable salt thereof and a compound useful in active or passive Tau immunotherapy and a pharmaceutically acceptable carrier.

Another paradigm to treat neurodegenerative and cognitive disorder, e.g. Alzheimer's disease is to target the Aβ peptides. It has been suggested that this can be achieved by either passive or active immunotherapy targeting Aβ peptides [*J Neurosci*, 34, 11621-11630, 2014; *J Neurosci* 33, 4923-4934, 2013]. In combination with compounds of the present invention this would attempt to target the same pathological mechanism via two different routes. Anti-Aβ antibodies (either injected directly into the patient or generated in the patient as a result of active immunotherapy) clear Aβ deposits in the brain, while further accumulation of Aβ peptide is blocked or reduced by the compounds of the present invention.

In one embodiment the invention provides a method for the treatment of a neurodegenerative or cognitive disorder, e.g. Alzheimer's disease, the method comprising the administration of a therapeutically effect amount of two components (1) a compound of Formula I or a pharmaceutically acceptable salt thereof and (2) a compound useful in active or passive Aβ peptide immunotherapy to a patient in need thereof. Said compound useful in passive Aβ peptide immunotherapy may be an anti-Aβ peptide antibody, such as gantenerumab, solanezumab, aducanumab or crenezumab. Said compound useful in active Aβ peptide immunotherapy may be a fragment of the Aβ peptide amino acid sequence which upon injection into a patient elicits anti-Aβ peptide antibodies in said patient. The administration according to this embodiment of the invention may be simultaneous, or there may be a time gap between the administration of the two components.

In one embodiment, the invention relates to the use of a compound of Formula I or a pharmaceutically acceptable salt thereof and a compound useful in active or passive Aβ peptide immunotherapy in the manufacture of a medicament for the treatment of neurodegenerative or cognitive disorder, e.g. Alzheimer's disease.

In one embodiment, the invention provides a compound of Formula I or a pharmaceutically acceptable salt thereof and a compound useful in active or passive Aβ peptide immunotherapy for use in a method for the treatment of a neurodegenerative or cognitive disorder, e.g. Alzheimer's disease.

In one embodiment, the invention provides a pharmaceutical composition comprising a compound of Formula I or a pharmaceutically acceptable salt thereof and a compound useful in active or passive Aβ peptide immunotherapy and a pharmaceutically acceptable carrier.

The NMDA (N-Methyl-D-Aspartate) receptor antagonist memantine and the acetylcholine esterase inhibitors donepezil, rivastigmine and galantamine are approved drugs for the treatment of Alzheimer's disease.

In one embodiment the invention provides a method for the treatment of a neurodegenerative or cognitive disorder, e.g. Alzheimer's disease, the method comprising the administration of a therapeutically effect amount of two components (1) a compound of Formula I or a pharmaceutically acceptable salt thereof and (2) an NMDA receptor antagonist or an acetylcholine esterase inhibitor to a patient in need thereof. The administration according to this embodiment of the invention may be simultaneous, or there may be a time gap between the administration of the two components.

In one embodiment, the invention relates to the use of a compound of Formula I or a pharmaceutically acceptable salt thereof and an NMDA receptor antagonist or an acetylcholine esterase inhibitor in the manufacture of a medicament for the treatment of neurodegenerative or cognitive disorder, e.g. Alzheimer's disease.

In one embodiment, the invention provides a compound of Formula I or a pharmaceutically acceptable salt thereof and an NMDA receptor antagonist or an acetylcholine esterase inhibitor for use in a method for the treatment of a neurodegenerative or cognitive disorder, e.g. Alzheimer's disease.

In one embodiment, the invention provides a pharmaceutical composition comprising a compound of Formula I or a pharmaceutically acceptable salt thereof and an NMDA receptor antagonist or an acetylcholine esterase inhibitor and a pharmaceutically acceptable carrier.

Seizures or epileptiform activity are also associated with Alzheimer's disease, including early stages of Alzheimer's disease, and treatment of said epileptic activity, which seeks to normalise hippocampal hyperactivity, may form part of an Alzheimer's disease treatment paradigm [*JAMA Neurol*, 70, 1158-1166, 2013; *J Neurosci Res*, 93, 454, 465, 2015; *Neuron*, 74, 647-474, 2012; *Neurepsychpharm*, 35, 1016-1025, 2010; *CNS Neurosci Ther*, 19, 871-881, 2013]. Useful antiepileptics include NMDA receptor antagonists and ion channel modulators, such as topiramate, levetiracetam and lamotrigine.

In one embodiment the invention provides a method for the treatment of a neurodegenerative or cognitive disorder, e.g. Alzheimer's disease, the method comprising the administration of a therapeutically effect amount of two components (1) a compound of Formula I or a pharmaceutically acceptable salt thereof and (2) an antiepileptic to a patient in need thereof. The administration according to this embodiment of the invention may be simultaneous, or there may be a time gap between the administration of the two components.

In one embodiment, the invention relates to the use of a compound of Formula I or a pharmaceutically acceptable salt thereof and an antiepileptic in the manufacture of a medicament for the treatment of neurodegenerative or cognitive disorder, e.g. Alzheimer's disease.

In one embodiment, the invention provides a compound of Formula I or a pharmaceutically acceptable salt thereof and an antiepileptic for use in a method for the treatment of a neurodegenerative or cognitive disorder, e.g. Alzheimer's disease.

In one embodiment, the invention provides a pharmaceutical composition comprising a compound of Formula I or a pharmaceutically acceptable salt thereof and an antiepileptic and a pharmaceutically acceptable carrier.

Emerging evidence suggests that inflammation has a causal role in Alzheimer's disease pathogenesis and that neuroinflammation is not a passive system activated by emerging β-amyloid deposits and neurofibrilary tangles, but also contributes to pathogenesis itself [*Lancet Neurol*, 14, 388-405, 2015; *J Alz Dis*, 44, 385-396, 2015; *Neurol*, 84, 2161-2168, 2015]. It follows from this that anti-inflammatory drugs, such as NSAID (non-steriod anti-inflammatory drugs), TNFα inhibitors, such as etanercept and p38 MAP kinase inhibitors, such as VX-745 (5-(2,6-Dichlorophenyl)-2-((2,4-difluorophenyl)thio)-6H-pyrimido[1,6-b]pyridazin-6-one) may be useful in the treatment of Alzheimer's disease.

In one embodiment the invention provides a method for the treatment of a neurodegenerative or cognitive disorder, e.g. Alzheimer's disease, the method comprising the administration of a therapeutically effect amount of two components (1) a compound of Formula I or a pharmaceutically acceptable salt thereof and (2) an anti-inflammatory drug to a patient in need thereof. The administration according to this embodiment of the invention may be simultaneous, or there may be a time gap between the administration of the two components.

In one embodiment, the invention relates to the use of a compound of Formula I or a pharmaceutically acceptable salt thereof and anti-inflammatory drug in the manufacture of a medicament for the treatment of neurodegenerative or cognitive disorder, e.g. Alzheimer's disease.

In one embodiment, the invention provides a compound of Formula I or a pharmaceutically acceptable salt thereof and an anti-inflammatory drug for use in a method for the treatment of a neurodegenerative or cognitive disorder, e.g. Alzheimer's disease.

In one embodiment, the invention provides a pharmaceutical composition comprising a compound of Formula I or a pharmaceutically acceptable salt thereof and an anti-inflammatory drug and a pharmaceutically acceptable carrier.

In addition, efficacy in the treatment of Alzheimer's disease has been demonstrated for Tau protein aggregation inhibitors, such as TRX-0237, also known as Methylene Blue, and SSRIs (Selective Serotonin Reuptake Inhibitor), such as citalopram [*Behav Pharmacol*, 26, 353-368, 2015; *Sci Transl Med*, 6(236re4), 2014].

In one embodiment the invention provides a method for the treatment of a neurodegenerative or cognitive disorder, e.g. Alzheimer's disease, the method comprising the administration of a therapeutically effect amount of two components (1) a compound of Formula I or a pharmaceutically acceptable salt thereof and (2) Tau protein aggregation inhibitor or an SSRI to a patient in need thereof. The administration according to this embodiment of the invention may be simultaneous, or there may be a time gap between the administration of the two components.

In one embodiment, the invention relates to the use of a compound of Formula I or a pharmaceutically acceptable salt thereof and a Tau protein aggregation inhibitor or an SSRI in the manufacture of a medicament for the treatment of neurodegenerative or cognitive disorder, e.g. Alzheimer's disease.

In one embodiment, the invention provides a compound of Formula I or a pharmaceutically acceptable salt thereof and a Tau protein aggregation inhibitor or an SSRI drug for use in a method for the treatment of a neurodegenerative or cognitive disorder, e.g. Alzheimer's disease.

In one embodiment, the invention provides a pharmaceutical composition comprising a compound of Formula I or a pharmaceutically acceptable salt thereof and a Tau protein aggregation inhibitor or an SSRI drug and a pharmaceutically acceptable carrier.

In one embodiment, a mammal is a human.

In one embodiment, the patient is a human patient.

Pharmaceutically Acceptable Salts

The compounds of this invention are generally used as the free base or as a pharmaceutically acceptable salt thereof. Pharmaceutically acceptable salts of a compound of Formula I are prepared e.g. in a conventional manner by treating a solution or suspension of a free base of Formula I with a molar equivalent of a pharmaceutically acceptable acid. Representative examples of suitable organic and inorganic acids are described below. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines (for example, 8-bromotheophylline and the like). Further examples of pharmaceutically acceptable inorganic or organic acid addition salts include the pharmaceutically acceptable salts listed in S. M. Berge, et al., J. Pharm. Sci., 1977, 66, 2.

Furthermore, the compounds of this invention may exist in unsolvated as well as in solvated forms with pharmaceutically acceptable solvents such as water, ethanol and the like.

The compounds of the present invention may have one or more asymmetric centres and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention.

In this context is understood that when specifying the enantiomeric form, then the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms may be resolved into the optical antipodes by known methods, for example, by separation of diastereomeric salts thereof with an optically active acid, and liberating the optically active amine compound by treatment with a base.

Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

Pharmaceutical Compositions

The present invention further provides a pharmaceutical composition comprising a compound of Formula I or a pharmaceutically acceptable salt thereof and a pharmaceutically acceptable carrier. The present invention also provides a pharmaceutical composition comprising a specific compound disclosed in the Experimental Section or a pharmaceutically acceptable salt thereof and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22$^{nd}$ Edition, Gennaro, Ed., Mack Publishing Co., Easton, Pa., 2013.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs. Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.01 to about 100 mg/kg body weight per day.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of Formula I or a pharmaceutically acceptable salt thereof and a pharmaceutically acceptable carrier are readily administered in a variety of dosage forms suitable for the disclosed routes of administration. The formulations may conveniently be presented in unit dosage form by methods known in the art of pharmacy.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

Process and Key Intermediates

Key intermediates in the preparation of a compounds of the invention are (6S)-3-Fluoro-3-(fluoromethyl)-6-(2-fluorophenyl)-6-methylpiperidin-2-one, (6S)-6-(2,3-Difluorophenyl)-3-fluoro-3-(fluoromethyl)-6-methylpiperidin-2-one, and (6S)-3-Fluoro-3,6-bis(fluoromethyl)-6-(2-fluorophenyl)piperidin-2-one. Accordingly, one aspect of the invention is directed to a compound selected from the group consisting of

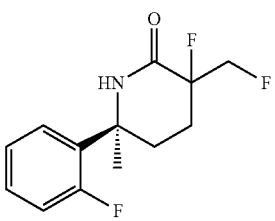 [SMILES: C[C@@]1(c2ccccc2F)CCC(F)(CF)C(=O)N1]

(6S)-3-fluoro-3-(fluoronnethyl)-6-(2-fluorophenyl)-6-methylpiperidin-2-one, and salts thereof;

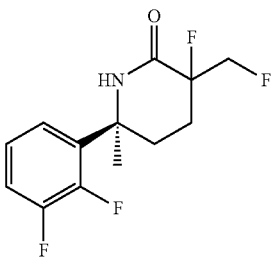 [SMILES: C[C@@]1(c2cccc(F)c2F)CCC(F)(CF)C(=O)N1]

(6S)-6-(2,3-difluorophenyl)-3-fluoro-3-(fluoromethyl)-6-methylpiperidin-2-one, and salts thereof, and

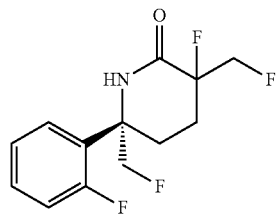 [SMILES: O=C1N[C@](CF)(c2ccccc2F)CCC1(F)CF]

(6S)-3-fluoro-3,6-bis(fluoromethyl)-6-(2-fluorophenyl)pipendin-2-one, and salts thereof.

(6S)-3-Fluoro-3-(fluoromethyl)-6-(2-fluorophenyl)-6-methylpiperidin-2-one and salts thereof, (6S)-6-(2,3-Difluorophenyl)-3-fluoro-3-(fluoromethyl)-6-methylpiperidin-2-one and salts thereof, and (6S)-3-Fluoro-3,6-bis(fluoromethyl)-6-(2-fluorophenyl)piperidin-2-one and salts thereof are central intermediates to the compounds of the invention. Coupling to an aromatic selected from phenyl, pyridyl, pyrimidyl, pyrazinyl, imidazolyl, pyrazolyl, thiazolyl, oxazolyl, isoxazolyl, according to the invention requires functionalization of the phenyl ring of the above phenyl piperidinones. As shown in the Experimental section, the key intermediates (6S)-3-Fluoro-3-(fluoromethyl)-6-(2-fluorophenyl)-6-methylpiperidin-2-one and salts thereof, (6S)-6-(2,3-Difluorophenyl)-3-fluoro-3-(fluoromethyl)-6-methylpiperidin-2-one and salts thereof, and (6S)-3-Fluoro-3,6-bis(fluoromethyl)-6-(2-fluorophenyl)piperidin-2-one and salts thereof were converted to further key intermediates of the invention, namely (3S,6S)-3-Fluoro-6-(2-fluoro-5-nitrophenyl)-3-(fluoromethyl)-6-methylpiperidin-2-one, (3R,6S)-3-fluoro-6-(2-fluoro-5-nitrophenyl)-3-(fluoromethyl)-6-methylpiperidin-2-one, (3S,6S)-6-(2,3-Difluoro-5-nitrophenyl)-3-fluoro-3-(fluoromethyl)-6-methylpiperidin-2-one, (3R,6S)-6-(2,3-difluoro-5-nitrophenyl)-3-fluoro-3-(fluoromethyl)-6-methylpiperidin-2-one and (6S)-3-Fluoro-6-(2-fluoro-5-nitrophenyl)-3,6-bis(fluoromethyl)piperidin-2-one. Accordingly, a further aspect of the invention relates to compounds selected from the group consisting of

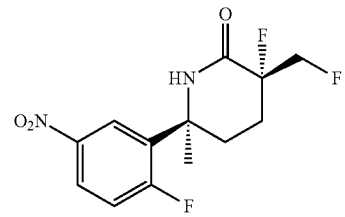

(3R,6S)-3-fluoro-6-(2-fluoro-5-nitrophenyl)-3-(fluoromethyl)-6-methylpiperidin-2-one

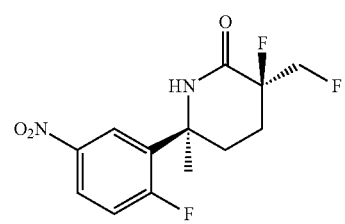

(3S,6S)-3-fluoro-6-(2-fluoro-5-nitrophenyl)-3-(fluoromethyl)-6-methylpiperidin-2-one

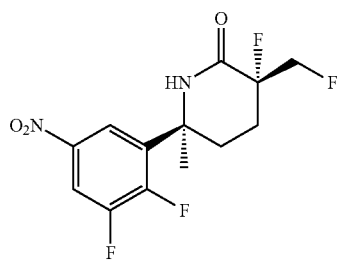 [SMILES: C[C@@]1(c2cc([N+](=O)[O-])cc(F)c2F)CC[C@](F)(CF)C(=O)N1]

(3R,6S)-6-(2,3-difluoro-5-nitrophenyl)-3-fluoro-3-(fluoromethyl)-6-methylpiperidin-2-one

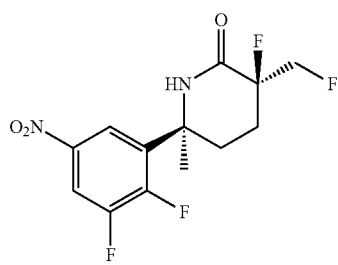 [SMILES: C[C@@]1(c2cc([N+](=O)[O-])cc(F)c2F)CC[C@@](F)(CF)C(=O)N1]

(3S,6S)-6-(2,3-difluoro-5-nitrophenyl)-3-fluoro-3-(fluoromethyl)-6-methylpiperidin-2-one, and

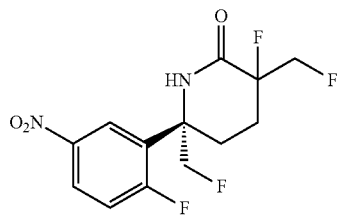

(6S)-3-fluoro-6-(2-fluoro-5-nitrophenyl)-3,6-bis(fluoromethyl)piperidin-2-one, and salts thereof.

As can be seen in greater detail from the experimental section below, the phenyl amino group on an intermediate provides for the key coupling step:

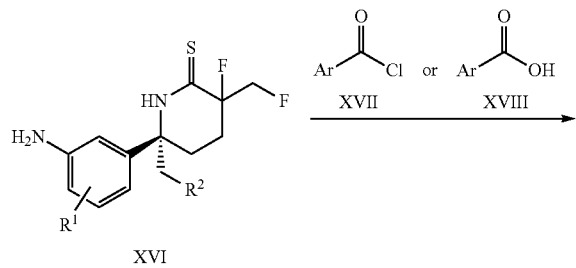

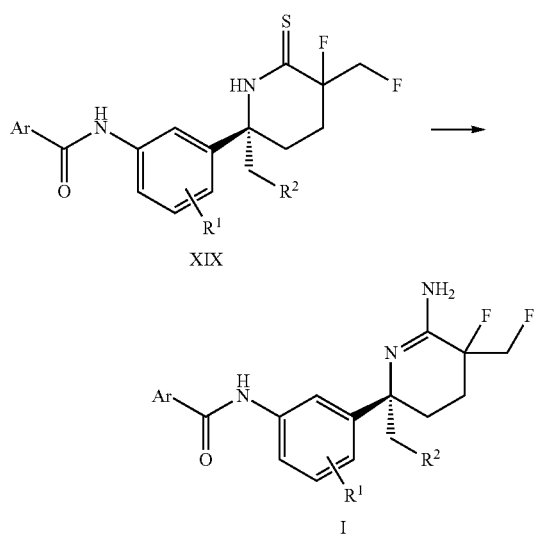

Compounds of formula XVI and salts thereof, and their immediate precursors, compounds of formula XVa and XVb and salts thereof are therefore also key intermediate compounds of the invention.

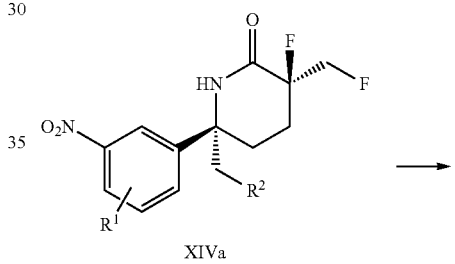

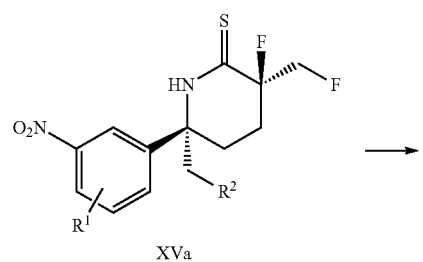

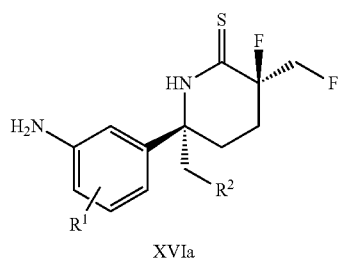

-continued

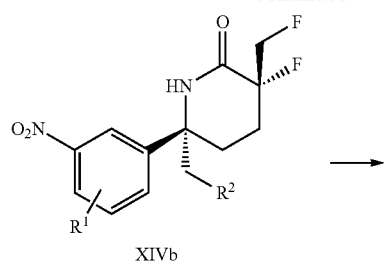
XIVb

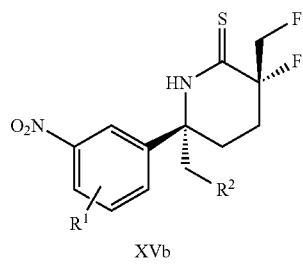
XVb

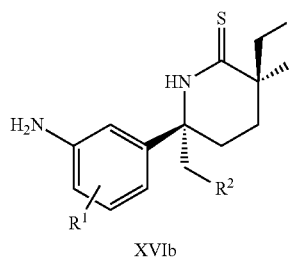
XVIb

Accordingly, a further aspect of the invention is directed to compounds selected from the group consisting of

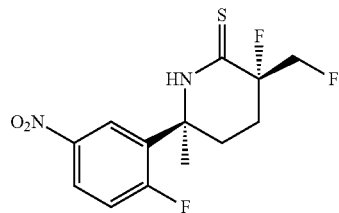 [SMILES: C[C@@]1(c2cc([N+](=O)[O-])ccc2F)CC[C@](F)(CF)C(=S)N1]

(3S,6S)-3-fluoro-6-(2-fluoro-5-nitrophenyl)-3-(fluoromethyl)-6-methylpiperidine-2-thione

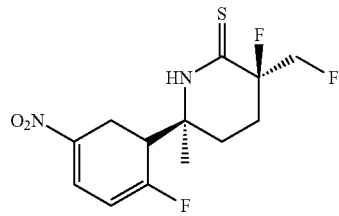 [SMILES: C[C@@]1(C2CC([N+](=O)[O-])=CC=C2F)CC[C@@](F)(CF)C(=S)N1]

(3R,6S)-3-fluoro-6-((R)-2-fluoro-5-nitrocyclohexa-2,4-dien-1-yl)-3-(fluoromethyl)-6-methylpiperidine-2-thione

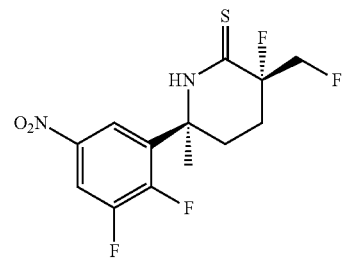 [SMILES: C[C@@]1(c2cc([N+](=O)[O-])cc(F)c2F)CC[C@](F)(CF)C(=S)N1]

(3S,6S)-6-(2,3-difluoro-5-nitrophenyl)-3-fluoro-3-(fluoromethyl)-6-methylpiperidine-2-thione

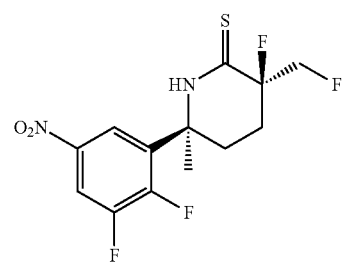

(3R,6S)-6-(2,3-difluoro-5-nitrophenyl)-3-fluoro-3-(fluoromethyl)-6-methylpiperidine-2-thione and

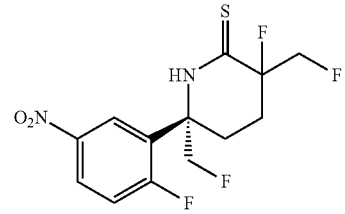 [SMILES: O=[N+]([O-])c1ccc(F)c([C@]2(CF)CCC(F)(CF)C(=S)N2)c1]

(6S)-3-fluoro-6-(2-fluoro-5-nitrophenyl)-3,6-bis(fluoromethyl)piperidine-2-thione, and salts thereof.

The intermediate compounds involved in the coupling step are a further aspect of the invention, namely compounds selected from the group consisting of

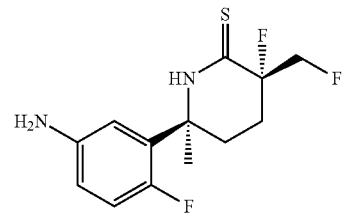

(3S,6S)-6-(5-amino-2-fluorophenyl)-3-fluoro-3-(fluoromethyl)-6-methylpiperidine-2-thione

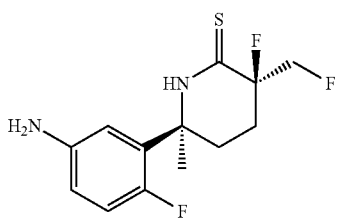

(3R,6S)-6-(5-amino-2-fluorophenyl)-3-fluoro-3-(fluoromethyl)-6-methylpiperidine-2-thione

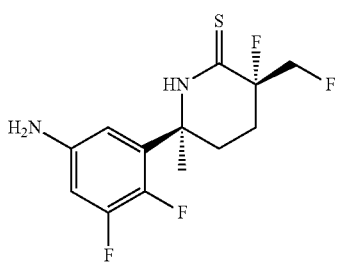

(3S,6S)-6-(5-amino-2,3-difluorophenyl)-3-fluoro-3-(fluoromethyl)-6-methylpiperidine-2-thione

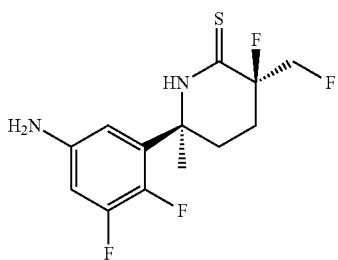 [SMILES: C[C@@]1(c2cc(N)cc(F)c2F)CC[C@@](F)(CF)C(=S)N1]

(3R,6S)-6-(5-amino-2,3-difluorophenyl)-3-fluoro-3-(fluoromethyl)-6-methylpiperidine-2-thione and

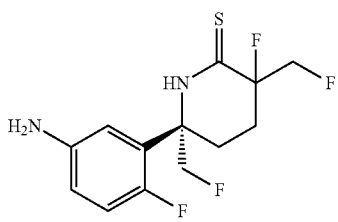

(6S)-6-(5-amino-2-fluorophenyl)-3-fluoro-3,6-bis(fluoromethyl)piperidine-2-thione, and salts thereof.

EXPERIMENTAL SECTION

The compounds of the present invention of general formula I, wherein $R^1$ and Ar are as defined above can be prepared by the methods outlined in the following reaction schemes 1-5 and in the examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

It may be necessary to incorporate protection and deprotection strategies for substituents such as amino, amido, keto and hydroxyl groups in the synthetic methods described below to synthesize the compounds of Formula I. Methods for protection and deprotection of such groups are well known in the art, and may be found in T. Green, et al., Protective Groups in Organic Synthesis, 1991, $2^{nd}$ Edition, John Wiley & Sons, New York.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers.

Analytical LC-MS data was obtained using the following methods.

Method A:

LC-MS was run on Waters Aquity UPLC-MS consisting of Waters Aquity including column manager, binary solvent manager, sample organizer, PDA detector (operating at 254 nm), ELS detector, and SQ-MS equipped with APPI-source operating in positive ion mode.

LC-conditions: The column was Acquity UPLC BEH C18 1.7 µm; 2.1×150 mm operating at 60° C. with 0.6 ml/min of a binary gradient consisting of water+0.05% trifluoroacetic acid (A) and acetonitrile+5% water+0.03% trifluoroacetic acid (B).

Gradient: 0.00 min: 10% B; 3.00 min: 99.9% B; 3.01 min: 10% B; 3.60 min: 10% B. Total run time: 3.60 min.

Method B:

LC-MS was run on Waters Acquity UPLC-MS consisting of Waters Acquity including column manager, binary solvent manager, sample organizer, PDA detector (operating at 254 nm), ELS detector, and TQ-MS equipped with APPI-source operating in positive ion mode.

LC-conditions: The column was Acquity UPLC BEH C18 1.7 µm; 2.1×50 mm operating at 60° C. with 1.2 ml/min of a binary gradient consisting of water+0.05% trifluoroacetic acid (A) and acetonitrile+5% water+0.05% trifluoroacetic acid (B).

Gradient: 0.00 min: 10% B; 1.00 min: 100% B; 1.01 min: 10% B; 1.15 min: 10% B. Total run time: 1.15 min.

Method C:

An Agilent 1200 LCMS system with ELS detector was used. Column: Agilent TC-C18 5 µm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/minute.

Method D:

An Agilent 1200 LCMS system with ELS detector was used. Column: XBridge ShieldRP18, 5 µm, 50×2.1 mm; Column temperature: 40° C.; Solvent system: A=water/ conc. $NH_3$ (aq) (99.95:0.05) and B=acetonitrile; Method: Linear gradient elution with A:B=95:5 to 0:100 in 3.4 minutes and with a flow rate of 0.8 mL/min.

$^1$H NMR spectra were recorded at 600 MHz on a Bruker Avance AV-III-600 instrument or at 400 MHz on a Bruker Avance AV-III-400 instrument or a Varian 400 instrument. Chemical shift values are expressed in ppm-values relative. The following abbreviations are used for multiplicity of NMR signals: s=singlet, d=doublet, t=triplet, q=quartet, dd=double doublet, ddd=double double doublet, dt=double triplet, br=broad, and m=multiplet.

Compounds of general formula XIII may be prepared as shown in Scheme 1.

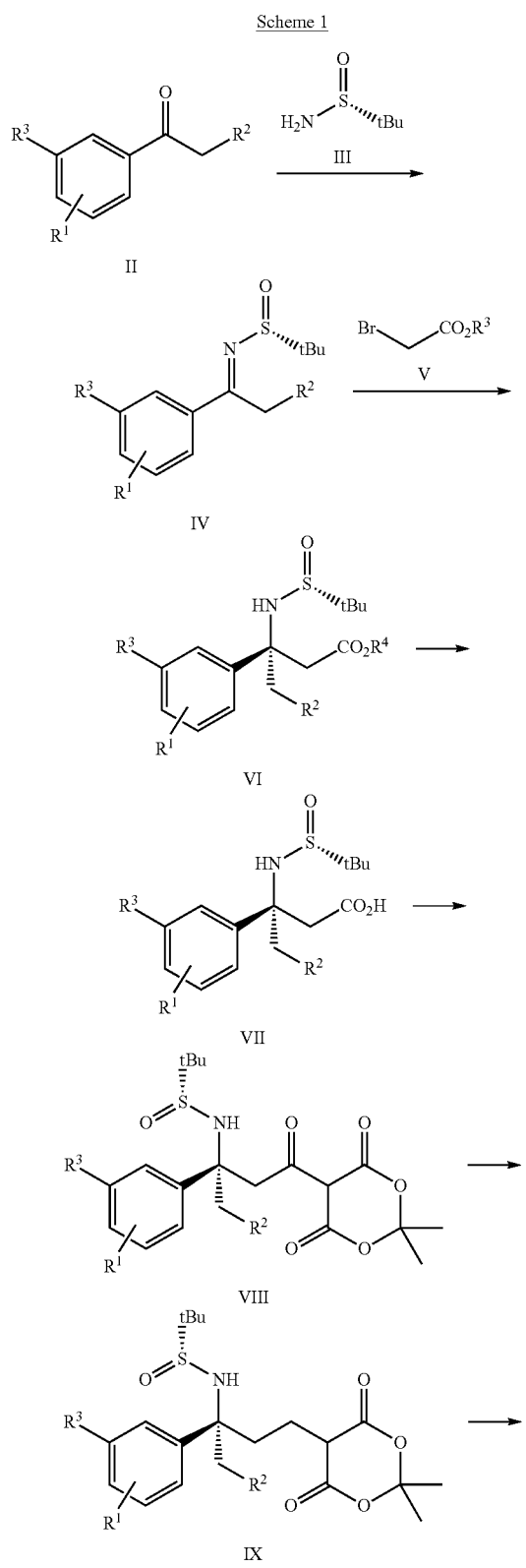

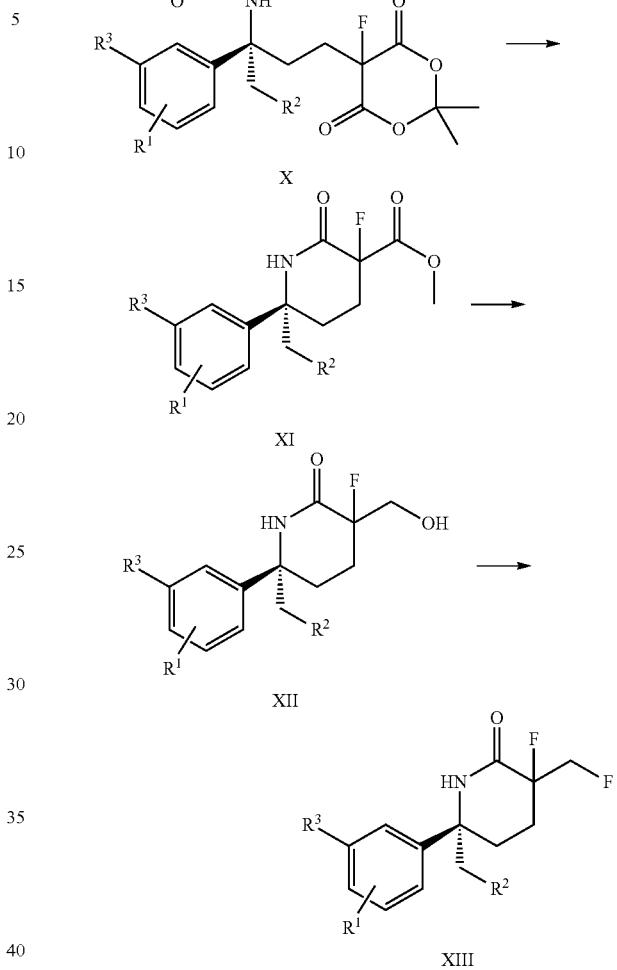

where $R^1$ and $R^2$ are as defined for Formula I, $R^3$ is hydrogen or a nitro group and $R^4$ is as an alkyl group such as methyl or ethyl Compounds of general formula IV (Scheme 1) may be prepared by reacting compounds of formula II with a sulfinamide such as III in the presence of a Lewis acid/drying agent such as titanium tetraethoxide. Treatment of compounds of general formula IV with compounds of general formula V such as ethyl bromoacetate in the presence of Zn powder or in the presence of diethyl zinc and tris(triphenylphosphine)rhodium(I) chloride gives compounds of general formula VI (Hilpert, H. et al *J. Med. Chem.* 2013, 56, 3980-3995). Hydrolysis of compounds of general formula VI with an aqueous base such as sodium hydroxide in water gives compounds of general formula VII. Activation of the acid group of compounds of general formula VII with a coupling reagent such as 1-ethyl-3-(3-dimethylaminopropyl) carbodiimide (EDC) in the presence of a catalyst such as 4-dimethylaminopyridine (DMAP) followed by reaction with Meldrum's acid (2,2-dimethyl-1,3-dioxane-4,6-dione) acid gives compounds of general formula VIII.

Reduction of compounds of general formula VIII with a reducing reagent such as sodium borohydride in a solvent such as acetic acid gives compounds of general formula IX. Compounds of general formula IX can be fluorinated with a fluorination reagent such as N-fluorodibenzenesulfonamide (NFSi) in the precense of a base such as 1,8-diazabicyclo[5.4.0]undec-7-ene (DBU) to give compounds of general formula X. Treating compounds of general formula X with an acid such as hydrochloric acid in methanol will cleave the sulfinamide bond and transesterification will occur on the two ester moieties. Treatment of the resulting intermediate with a base such as potassium carbonate in methanol gives compounds of general formula XI as a mixture of two diastereomers. The ester moiety of compounds of general formula XI can be reduced with a reducing reagent such as sodium borohydride to give compounds of general formula XII. The mixture of two diastereomers of compounds of general formula XII can be converted to compounds of general formula XIII as a mixture of two diastereomers by treatment with reagents such as nonafluorobutanesulfonyl fluoride (NfF) and a base such as triethylamine followed by treatment with a reagent such as tetra-N-butylammonium fluoride (TBAF). The mixture of two diastereomers of compounds of general formula XIII when $R^3$ is a nitro group can be separated by chromatography to give compounds of general formulae XIVa and XIVb (Scheme 2)

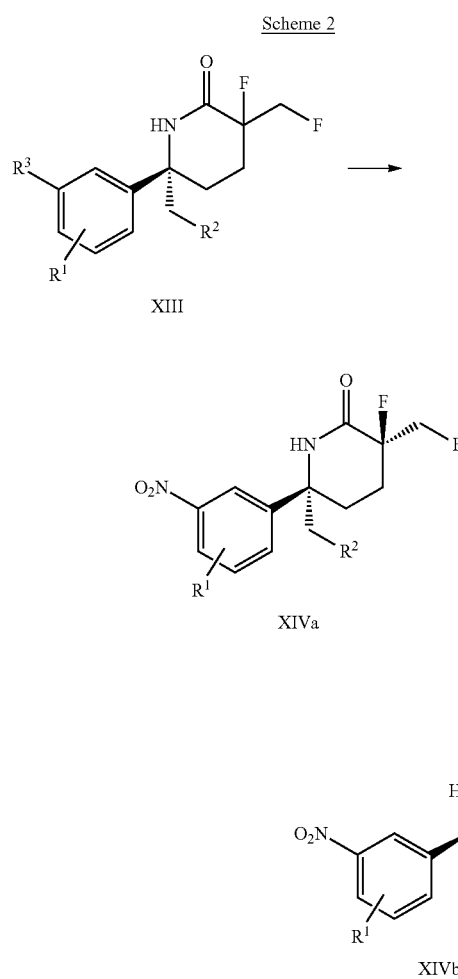

where $R^1$ and $R^2$ are as defined under formula I and $R^3$ is a nitro group.

Compounds of general formulae XIVa and XIVb may be prepared as shown in Scheme 3.

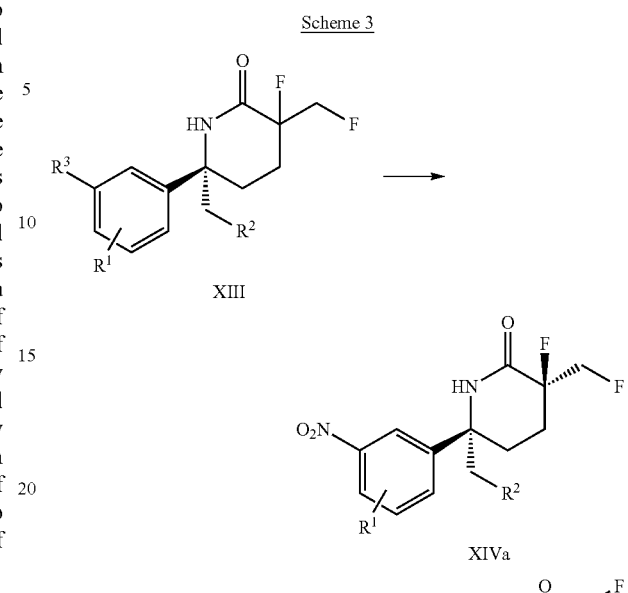

where $R^1$ and $R^2$ are as defined under formula I and $R^3$ is hydrogen Treatment of a mixture of two diastereomers of compounds of general formula XIII with nitric acid in sulfuric acid and trifluoroacetic acid gives compounds of general formulae XIVa and XIVb which can be separated by chromatography (Scheme 3).

Compounds of general formulae XVIa and XVIb may be prepared as shown in Scheme 4.

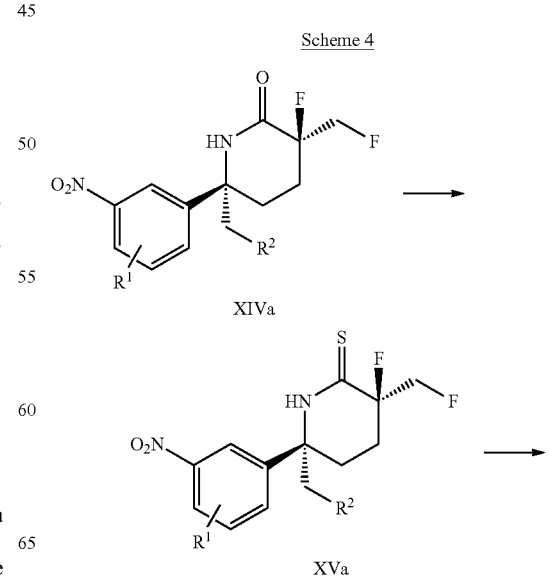

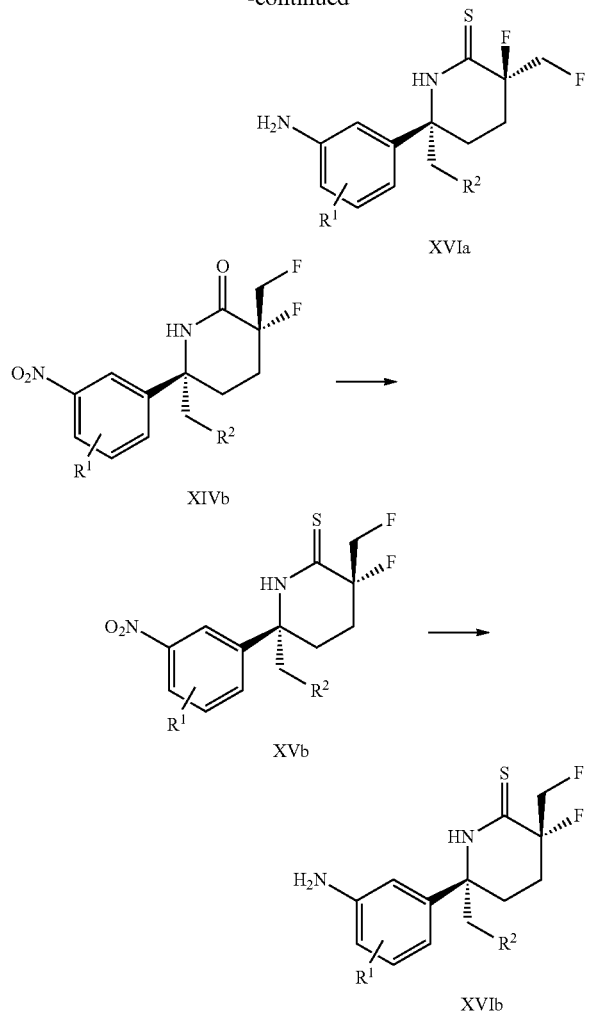

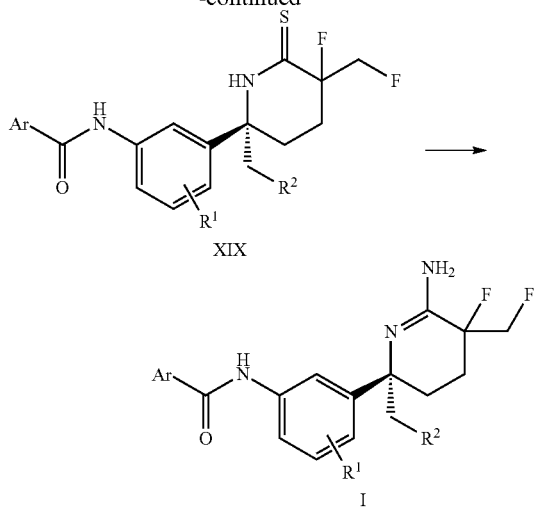

where $R^1$, $R^2$ and Ar are as defined under Formula I.

Compounds of general formula XIX (Scheme 5) may be prepared by reacting compounds of general formula XVI with a carboxylic acid chloride of general formula XVII or by reaction with a carboxylic acid of general formula XVIII using procedures known to chemists skilled in the art. Treatment of compounds of general formula XIX with ammonia gives compounds of general formula I. In some cases, the addition of and oxidizing reagent such as tert-butyl hydroperoxide might be necessary to facilitate the reaction.

Preparation of Intermediates

Intermediate (R)-N-(1-(2-Fluorophenyl)ethylidene)-2-methylpropane-2-sulfinamide

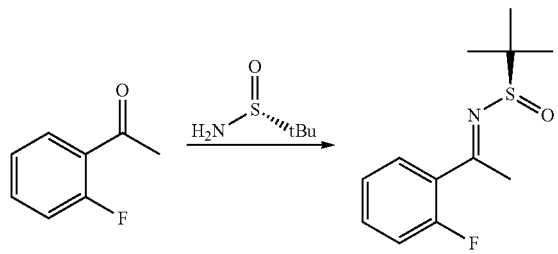

where $R^1$ and $R^2$ are as defined under formula I

Treatment of compounds of general formula XIVa (Scheme 4) with a reagent such as Lawesson's reagent (2,4-bis(4-methoxyphenyl)-1,3,2,4-dithiadiphosphetane-2, 4-disulfide) gives compounds of general formula XVa. Reduction of the nitro group of compounds of general formula XVa gives compounds of general formula XVIa. The same procedures can be used to prepare compounds of general formula XVIb starting from compounds of general formula XIVb.

Compounds of general Formula I may be prepared as shown in Scheme 5.

Scheme 5

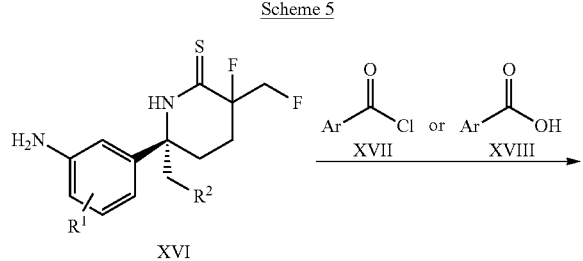

To a solution of 1-(2-fluorophenyl)ethanone (25.0 g, 181 mmol) in THF (500 mL) was added Ti(OEt)$_4$ (82.6 g, 362.0 mmol) and (R)-2-methylpropane-2-sulfinamide (26.3 g, 217 mmol). The mixture was stirred at 85° C. for 14 hours. The reaction mixture was quenched with water (200 mL) and then filtered and the filtrate was extracted with ethyl acetate (3×200 mL). The combined organic layers were washed with brine (100 mL), dried over Na$_2$SO$_4$, filtered and concentrated under reduced pressure. The residue was combined with four similar batches (25 g reactant 1-(2-fluorophenyl)ethanone for each batch), the mixture was purified by column chromatography (silica gel, petroleum ether/ethyl acetate=10/1 to 5:1). (R)-N-(1-(2-fluorophenyl) ethylidene)-2-methylpropane-2-sulfinamide (135.0 g, 77.3% yield) was obtained.

(R)-N-(1-(2,3-Difluorophenyhethylidene)-2-methyl-propane-2-sulfinamide was prepared in a similar way from 1-(2,3-difluorophenypethan-1-one (R)-N-(2-Fluoro-1-(2-fluorophenyl)ethylidene)-2-methylpropane-2-sulfinamide was prepared in a similar way from 2-fluoro-1-(2-fluorophenypethan-1-one Intermediate 2-(2-Fluorophenyl)-2,2-dimethoxyethan-1-ol

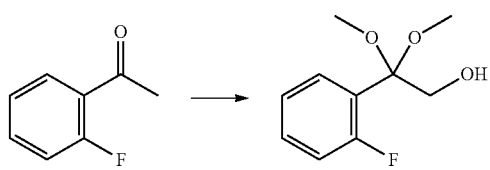

To a mixture of potassium hydroxide (91.4 g, 1.63 mol) in methanol (1 L) was added a solution of 1-(2-fluorophenyl)ethan-1-one (50 g, 362 mmol) in methanol (300 mL) in a dropwise manner at 0° C. Then bis(acetoxy)iodobenzene (175 g, 543 mmol) was added in portions. After stirring at 0° C. for 4 hours, the reaction was quenched with the addition of water (500 mL). The mixture was concentrated to remove methanol and the aqueous phase was extracted with ethyl acetate (700 mL, three times), the combined organic phases were washed with brine (300 mL), dried over Na$_2$SO$_4$ and concentrated. The crude product was used in the next step directly without further purification.

Intermediate 1-(2-Fluorophenyl)-2-hydroxyethan-1-one

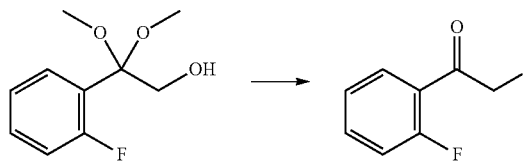

2-(2-Fluorophenyl)-2,2-dimethoxyethan-1-ol (crude, 362 mmol) was dissolved in THF (450 mL) and water (150 mL). Then p-toluene sulfonic acid (125 g, 726 mmol) was added portionwise at room temperature. After the addition, the mixture was stirred under reflux for 5 hours. Water (150 mL) and sat. NaHCO$_3$ was added to quench the reaction, the mixture was extracted with ethyl acetate (500 mL, three times). The combined organic layers were washed with brine and dried over Na$_2$SO$_4$. After removal of the solvents under reduced pressure, the residue was purified by column chromatography with petroleum ether:ethyl acetate=20:1 to give 1-(2-fluorophenyl)-2-hydroxyethan-1-one (42 g, 76% yield, two steps).

Intermediate

2-Fluoro-1-(2-fluorophenypethan-1-one

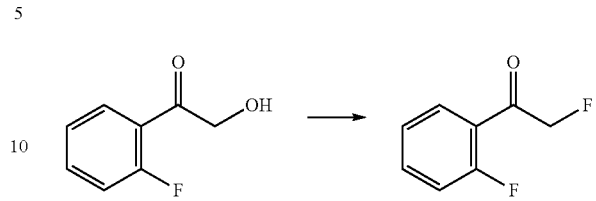

To a solution of 1-(2-fluorophenyl)-2-hydroxyethan-1-one (10 g, 64.88 mmol) in dichloromethane (200 mL) was added Et$_3$N(HF)$_3$ (10.46 g, 227.8 mmol) and CF$_3$(CF$_2$)$_3$SO$_2$F (29.4 g, 97.32 mmol) dropwise at 0° C., the solution was stirred at room temperature for 12 hours. TLC (petroleum ether:ethyl acetate=10:1) showed no starting material. The mixture was poured into a saturated solution of NaHCO$_3$ and ice, extracted with dichloromethane (200 mL three times), the combined organic layers were washed with brine, then dried over Na$_2$SO$_4$ and concentrated under reduced pressure. The mixture was purified by column chromatography on silica gel (eluted with petroleum ether:ethyl acetate=1:0-10:1) to afford 2-fluoro-1-(2-fluorophenyl) ethan-1-one (6 g, yield: 59%).

Intermediate

Ethyl (S)-3-(((R)-tert-butylsulfinyl)amino)-3-(2-fluorophenyl)butanoate

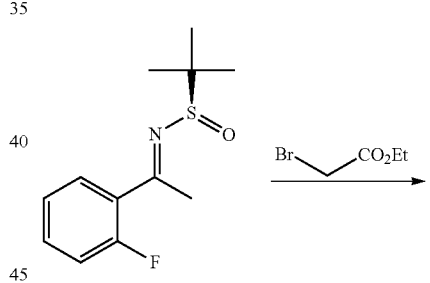

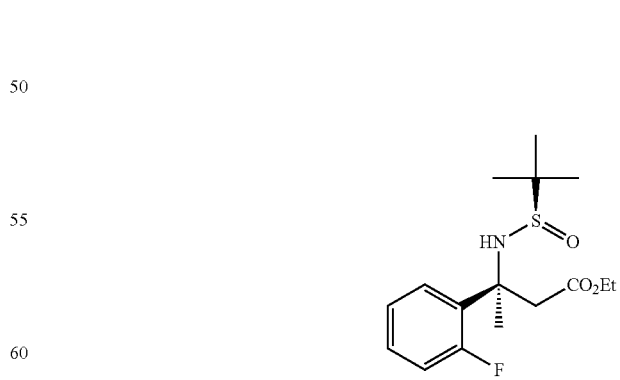

To a solution of (R)-N-(1-(2-fluorophenyl)ethylidene)-2-methylpropane-2-sulfinamide (20.0 g, 82.9 mmol) and Rh(PPh$_3$)$_3$Cl (2.3 g, 2.5 mmol) in dry THF (300 mL) was added dropwise Et$_2$Zn (1 M, 161.6 mL) at −78° C. The mixture was stirred at −78° C.-0° C. for 2 hours. The reaction mixture was quenched by NR₄Cl (sat. aq. 100 mL) at 0° C., and then diluted with water (200 mL) and extracted with ethyl acetate (2×200 mL). The combined organic layers were washed with brine (50 mL) dried over Na$_2$SO$_4$, filtered and concentrated under reduced pressure. The crude product was purified by flash chromatography on silica gel with petroleum ether/ethyl acetate=4/1. Ethyl (S)-3-(((R)-tert-butylsulfinyl)amino)-3-(2-fluorophenyl)butanoate (23.3 g, 85.3% yield) was obtained as a yellow oil. $^1$H NMR (CDCl$_3$ 400 MHz): δ7.53-7.49 (m, 1H), 7.27-7.25 (m, 1H), 7.14-7.12 (m, 1H), 7.05-6.99 (m, 1H), 5.15 (s, 1H), 4.02 (q, J=7.2 Hz, 2H), 3.38 (d, J=16.0 Hz, 1H), 3.10(d, J=17.6 Hz, 1H), 1.85 (s, 3H), 1.31 (s, 9H), 1.13 (t, J=7.2 Hz, 3H).

Ethyl (S)-3-(((R)-tert-butylsulfinyl)amino)-3-(2,3-difluorophenyl)butanoate was prepared in a similar way from (R)-N-(1-(2,3-difluorophenyl)ethylidene)-2-methylpropane-2-sulfinamide Ethyl (S)-3-(((R)-tert-butylsulfinyl)amino)-4-fluoro-3-(2-fluorophenyl)butanoate was prepared in a similar way from ((R)-N-(2-fluoro-1-(2-fluorophenyl)ethylidene)-2-methylpropane-2-sulfinamide Intermediate (S)-3-(((R)-tert-Butylsulfinyl)amino)-3-(2-fluorophenyl)butanoic acid

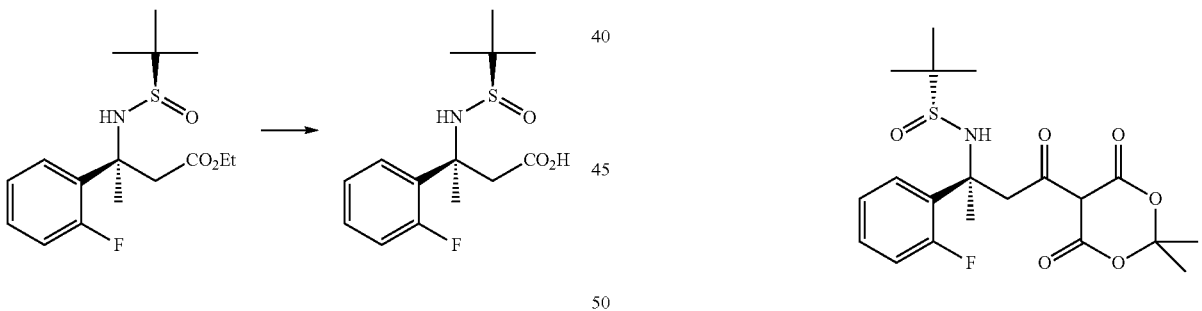

To a solution of ethyl (S)-3-(((R)-tert-butylsulfinyl)amino)-3-(2-fluorophenyl)butanoate (18.3 g, 55.6 mmol) in THF (180 mL) and H$_2$O (60 mL) was added LiOH.H$_2$O (2.8 g, 66.7 mmol). The mixture was stirred at 18° C. for 18 hours. The reaction mixture was adjusted pH to 3~4 by adding KHSO$_4$ (sat. aq.). The resulting mixture was extracted with ethyl acetate (3×200 mL). The combined organic layers were washed with brine (50 mL), dried over Na$_2$SO$_4$ and concentrated. (S)-3-(((R)-tert-butylsulfinyl)amino)-3-(2-fluorophenyl)butanoic acid (16.7 g, crude) was obtained and was used into the next step without further purification.

(S)-3-(((R)-tert-Butylsulfinyl)amino)-3-(2,3-difluorophenyl)butanoic acid was prepared in a similar way from ethyl (S)-3-(((R)-tert-butylsulfinyl)amino)-3-(2,3-difluorophenyl)butanoate (S)-3-(((R)-tert-butylsulfinyl)amino)-4-fluoro-3-(2-fluorophenyl)butanoic acid was prepared in a similar way from ethyl (S)-3-(((R)-tert-butylsulfinyl)amino)-4-fluoro-3-(2-fluorophenyl)butanoate Intermediate (R)-N-((S)-4-(2,2-Dimethyl-4,6-dioxo-1,3-dioxan-5-yl)-2-(2-fluorophenyl)-4-oxobutan-2-yl)-2-methylpropane-2-sulfinamide

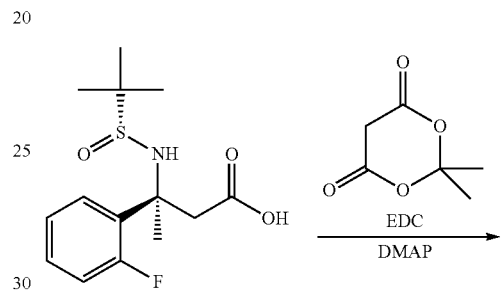

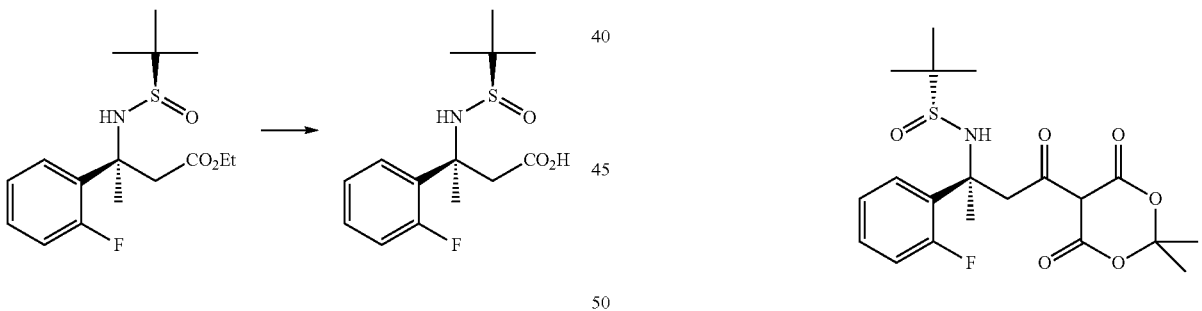

To a solution of (S)-3-(((R)-tert-butylsulfinyl)amino)-3-(2-fluorophenyl)butanoic acid (10.0 g, 33.2 mmol) in dry THF (100 mL) was added 1-ethyl-3-(3-dimethylaminopropyl)carbodiimide (EDC) (7.6 g, 39.8 mmol) and 4-dimethylaminopyridine (DMAP) (4.9 g, 39.8 mmol). The mixture was stirred at 20° C. for 5 min, then Meldrum's acid (2,2-dimethyl-1,3-dioxane-4,6-dione) (4.8 g, 33.2 mmol) was added. The mixture was stirred at 20° C. for 18 hours. Water (150 mL) was added, the resulting mixture was extracted with ethyl acetate (3×150 mL). The combined organic layers were washed with brine (50 mL), dried over Na$_2$SO$_4$ and concentrated. (R)-N-((S)-4-(2,2-dimethyl-4,6-dioxo-1,3-dioxan-5-yl)-2-(2-fluorophenyl)-4-oxobutan-2-yl)-2-methylpropane-2-sulfinamide (14.2 g, crude) was obtained and was used into the next step without further purification.

31

(R)-N-((S)-2-(2,3-Difluorophenyl)-4-(2,2-dimethyl-4,6-dioxo-1,3-dioxan-5-yl)-4-oxobutan-2-yl)-2-methylpropane-2-sulfinamide was prepared in a similar way from (S)-3-(((R)-tert-butylsulfinyl)amino)-3-(2,3-difluorophenyl)butanoic acid (R)-N-((S)-4-(2,2-dimethyl-4,6-dioxo-1,3-dioxan-5-yl)-1-fluoro-2-(2-fluorophenyl)-4-oxobutan-2-yl)-2-methylpropane-2-sulfinamide was prepared in a similar way from (S)-3-(((R)-tert-butylsulfinyl)amino)-4-fluoro-3-(2-fluorophenyl)butanoic acid Intermediate (R)-N-((S)-4-(2,2-Dimethyl-4,6-dioxo-1,3-dioxan-5-yl)-2-(2-fluorophenyl)butan-2-yl)-2-methylpropane-2-sulfinamide

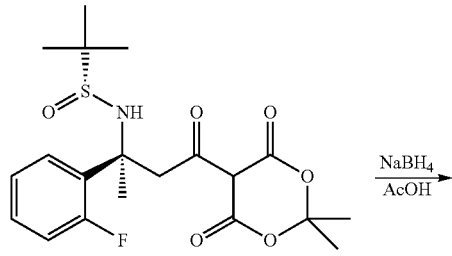

To a solution of (R)-N-((S)-4-(2,2-dimethyl-4,6-dioxo-1,3-dioxan-5-yl)-2-(2-fluorophenyl)-4-oxobutan-2-yl)-2-methylpropane-2-sulfinamide (14.2 g, 33.2 mmol) in acetic acid (150 mL) was added NaBH$_4$ (6.3 g, 165.9 mmol) in 5 portions with 15 minute intervals. Then the mixture was stirred at 20° C. for 18 hours. NR$_4$Cl (sat. aq. 100 mL) was added to quench the reaction, then the mixture was concentrated. Water (150 mL) was added and the mixture was extracted with ethyl acetate (3×170 mL), the combined organic layers were washed with brine (100 mL), dried over Na$_2$SO$_4$ and concentrated. (R)-N-((S)-4-(2,2-dimethyl-4,6-dioxo-1,3-dioxan-5-yl)-2-(2-fluorophenyl)butan-2-yl)-2-methylpropane-2-sulfinamide (13.7 g, crude) was obtained and was used into the next step without further purification.

32

(R)-N-((S)-2-(2,3-Difluorophenyl)-4-(2,2-dimethyl-4,6-dioxo-1,3-dioxan-5-yl)butan-2-yl)-2-methylpropane-2-sulfinamide was prepared in a similar way from (R)-N-((S)-2-(2,3-difluorophenyl)-4-(2,2-dimethyl-4,6-dioxo-1,3-dioxan-5-yl)-4-oxobutan-2-yl)-2-methylpropane-2-sulfinamide (R)-N-((S)-4-(2,2-dimethyl-4,6-dioxo-1,3-dioxan-5-yl)-1-fluoro-2-(2-fluorophenyl)butan-2-yl)-2-methylpropane-2-sulfinamide was prepared in a similar way from (R)-N-((S)-4-(2,2-dimethyl-4,6-dioxo-1,3-dioxan-5-yl)-1-fluoro-2-(2-fluorophenyl)-4-oxobutan-2-yl)-2-methylpropane-2-sulfinamide Intermediate (R)-N-((S)-4-(5-Fluoro-2,2-dimethyl-4,6-dioxo-1,3-dioxan-5-yl)-2-(2-fluorophenyl)butan-2-yl)-2-methylpropane-2-sulfinamide

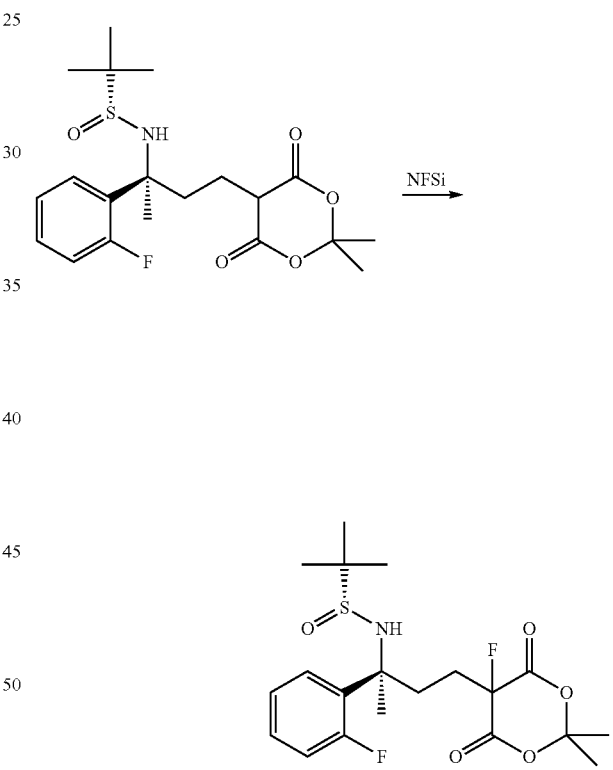

To a solution of (R)-N-((S)-4-(2,2-dimethyl-4,6-dioxo-1,3-dioxan-5-yl)-2-(2-fluorophenyl)butan-2-yl)-2-methylpropane-2-sulfinamide (5.0 g, 12.1 mmol) in anhydrous THF (75 mL) was added N-fluorodibenzenesulfonamide (NFSi) (4.6 g, 14.5 mmol) and 1,8-diazabicyclo[5.4.0]undec-7-ene (DBU) (1.8 g, 12.1 mmol) at 0° C. The mixture was stirred at 0° C.-20° C. for 1 hour. The mixture was filtered and the filtrate was concentrated. (R)-N-((S)-4-(5-fluoro-2,2-dimethyl-4,6-dioxo-1,3-dioxan-5-yl)-2-(2-fluorophenyl)butan-2-yl)-2-methylpropane-2-sulfinamide (5.2 g, crude) was obtained and was used into the next step without further purification.

(R)-N-((S)-2-(2,3-Difluorophenyl)-4-(5-fluoro-2,2-dimethyl-4,6-dioxo-1,3-dioxan-5-yl)butan-2-yl)-2-methylpropane-2-sulfinamide was prepared in a similar way from (R)-N-((S)-2-(2,3-difluorophenyl)-4-(2,2-dimethyl-4,6-dioxo-1,3-dioxan-5-yl)butan-2-yl)-2-methylpropane-2-sulfinamide (R)-N-((S)-1-fluoro-4-(5-fluoro-2,2-dimethyl-4,6-dioxo-1,3-dioxan-5-yl)-2-(2-fluorophenyl)butan-2-yl)-2-methylpropane-2-sulfinamide was prepared in a similar way from (R)-N-((S)-4-(2,2-dimethyl-4,6-dioxo-1,3-dioxan-5-yl)-1-fluoro-2-(2-fluorophenyl)butan-2-yl)-2-methylpropane-2-sulfinamide Intermediate Methyl (6S)-3-fluoro-6-(2-fluorophenyl)-6-methyl-2-xopiperidine-3-carboxylate

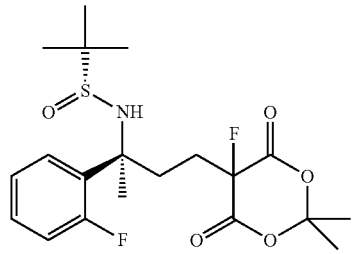

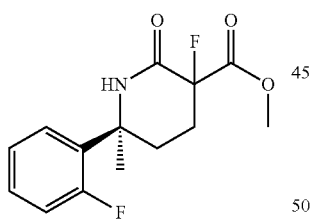

To a solution of (R)-N-((S)-4-(5-fluoro-2,2-dimethyl-4,6-dioxo-1,3-dioxan-5-yl)-2-(2-fluorophenyl)butan-2-yl)-2-methylpropane-2-sulfinamide (5.2 g, 12.1 mmol) in MeOH (50 mL) was added HCl/MeOH (4 M, 30.3 mL). The mixture was stirred at 20° C. for 18 hours. The mixture was concentrated and redissolved in dry MeOH (60 mL). Triethylamine was added (2.9 g, 29.1 mmol). The mixture was stirred at 80° C. for 18 hours. The mixture was concentrated. Then anhydrous THF (100 mL) was added and the mixture was stirred at 20° C. for 5 min. The mixture was filtered and the residue was washed with anhydrous THF (2×30 mL) and the combined filtrates were concentrated. Methyl (6S)-3-fluoro-6-(2-fluorophenyl)-6-methyl-2-oxopiperidine-3-carboxylate (3.4 g, crude) was obtained and was used into the next step without further purification.

Methyl (6S)-6-(2,3-difluorophenyl)-3-fluoro-6-methyl-2-oxopiperidine-3-carboxylate was prepared in a similar way from (R)-N-((S)-2-(2,3-difluorophenyl)-4-(5-fluoro-2,2-dimethyl-4,6-dioxo-1,3-dioxan-5-yl)butan-2-yl)-2-methylpropane-2-sulfinamide Methyl (6S)-3-fluoro-6-(fluoromethyl)-6-(2-fluorophenyl)-2-oxopiperidine-3-carboxylate was prepared in a similar way from (R)-N-((S)-1-fluoro-4-(5-fluoro-2,2-dimethyl-4,6-dioxo-1,3-dioxan-5-yl)-2-(2-fluorophenyl)butan-2-yl)-2-methylpropane-2-sulfinamide Intermediate (6S)-3-Fluoro-6-(2-fluorophenyl)-3-(hydroxymethyl)-6-methylpiperidin-2-one

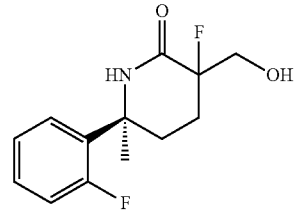

To a solution of methyl (6S)-3-fluoro-6-(2-fluorophenyl)-6-methyl-2-oxopiperidine-3-carboxylate (3.4 g, 12.1 mmol) in anhydrous MeOH (50 mL) was added NaBH₄ (3.7 g, 96.9 mmol) in 5 portions with 15 minute intervals. The mixture was stirred at 20° C. for 17 hours. The mixture was concentrated, then water (200 mL) was added and the mixture was extracted with ethyl acetate (3×150 mL). The combined organic layers were washed with brine (50 mL), dried over Na₂SO₄ and concentrated. The crude product was purified by flash chromatography on silica gel with petroleum ether:ethyl acetate=1:1~1:2 to give (6S)-3-fluoro-6-(2-fluorophenyl)-3-(hydroxymethyl)-6-methylpiperidin-2-one (2.5 g, 80.9% yield).

(6S)-6-(2,3-Difluorophenyl)-3-fluoro-3-(hydroxymethyl)-6-methylpiperidin-2-one was prepared in a similar way from methyl (6S)-6-(2,3-difluorophenyl)-3-fluoro-6-methyl-2-oxopiperidine-3-carboxylate (6S)-3-Fluoro-6-(fluoromethyl)-6-(2-fluorophenyl)-3-(hydroxymethyl)piperidin-2-one was prepared in a similar way from methyl (6S)-3-fluoro-6-(fluoromethyl)-6-(2-fluorophenyl)-2-oxopiperidine-3-carboxylate Intermediate (6S)-3-Fluoro-3-(fluoromethyl)-6-(2-fluorophenyl)-6-methylpiperidin-2-one

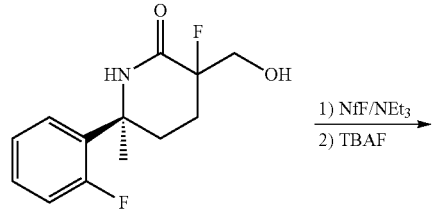

To a solution of (6S)-3-fluoro-6-(2-fluorophenyl)-3-(hydroxymethyl)-6-methylpiperidin-2-one (2.8 g, 11.0 mmol) in anhydrous THF (60 mL) was added nonafluorobutanesulfonyl fluoride (NfF) (9.9 g, 32.9 mmol) and triethylamine (4.4 g, 43.9 mmol). The mixture was stirred at 20° C. for 2.5 hours. A solution of tetra-N-butylammonium fluoride (TBAF) (1 M, 13.2 mL) in THF was added. The mixture was stirred at 50° C. for 16 h. Water (150 mL) was added. The mixture was extracted with ethyl acetate (3×100 mL). The combined organic phase was washed with brine (30 mL), dried over MgSO$_4$ and concentrated in vacuo. The crude material was purified via flash chromatography on silica gel with petroleum ether:ethyl acetate=2:1 to give (6S)-3-fluoro-3-(fluoromethyl)-6-(2-fluorophenyl)-6-methylpiperidin-2-one (2.4 g, 85.1% yield).

(6S)-6-(2,3-Difluorophenyl)-3-fluoro-3-(fluoromethyl)-6-methylpiperidin-2-one was prepared in a similar way from (6S)-6-(2,3-difluorophenyl)-3-fluoro-3-(hydroxymethyl)-6-methylpiperidin-2-one (6S)-3-Fluoro-3,6-bis(fluoromethyl)-6-(2-fluorophenyl)piperidin-2-one was prepared in a similar way from (6S)-3-fluoro-6-(fluoromethyl)-6-(2-fluorophenyl)-3-(hydroxymethyl) piperidin-2-one Intermediates (3S,6S)-3-Fluoro-6-(2-fluoro-5-nitrophenyl)-3-(fluoromethyl)-6-methylpiperidin-2-one and (3R,6S)-3-fluoro-6-(2-fluoro-5-nitrophenyl)-3-(fluoromethyl)-6-methylpiperidin-2-one

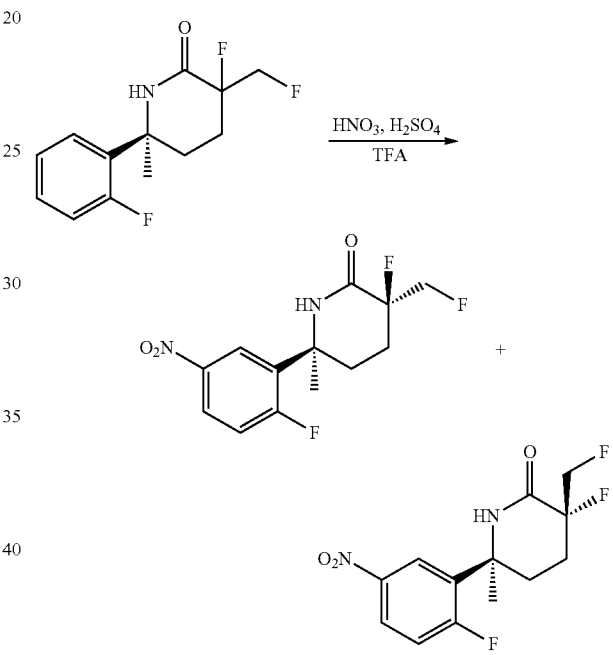

(6S)-3-Fluoro-3-(fluoromethyl)-6-(2-fluorophenyl)-6-methylpiperidin-2-one (1.4 g, 5.4 mmol) was suspended in TFA (9 mL). The mixture was cooled to 0° C. and concentrated H$_2$SO$_4$ (4.2 g, 41.9 mmol) (98%) was added. Finally, HNO$_3$ (1.7 g, 16.3 mmol) (60%) was added dropwise. After addition, the black brown mixture was stirring at 0° C. for 2 h. The mixture was poured onto 100 g ice and basified to pH>11 using 5 M NaOH (aq.). The suspension was extracted with ethyl acetate (150 mL). The phases were separated and the aqueous layer was extracted with ethyl acetate (2×100 mL). The combined organics were washed with a solution of saturated aqueous NH$_4$Cl (50 mL) and water (50 mL), dried over MgSO$_4$, filtered, and concentrated under reduced pressure. The residue was purified by column chromatography (silica gel, petroleum ether/ethyl acetate=2/1) to give (3S,6S)-3-fluoro-6-(2-fluoro-5-nitrophenyl)-3-(fluoromethyl)-6-methylpiperidin-2-one and (3R,6S)-3-fluoro-6-(2-fluoro-5-nitrophenyl)-3-(fluoromethyl)-6-methylpiperidin-2-one. (3S,6S)-3-Fluoro-6-(2-fluoro-5-nitrophenyl)-3-(fluoromethyl)-6-methylpiperidin-2-one (900 mg) $^1$H NMR (CDCl$_3$ 400 MHz): δ8.42-8.40 (m, 1H), 8.26-8.22 (m, 1H), 7.56 (brs, 1H), 7.31-7.26 (m, 1H), 4.78 (d, J=19.6 Hz, 1H), 4.67

(d, J=19.6 Hz, 1H), 2.61-2.57 (m, 1H), 2.38-2.30 (m, 1H), 2.20-2.19 (m, 1H), 2.19-2.16 (m, 1H), 1.78 (s, 3H).

(3R,6S)-3-Fluoro-6-(2-fluoro-5-nitrophenyl)-3-(fluoromethyl)-6-methylpiperidin-2-one (600 mg) $^1$H NMR (CDCl₃ 400 MHz): δ8.29-8.22 (m, 2H), 7.72 (brs, 1H), 7.31-7.26 (m, 1H), 4.72-4.47 (m, 2H), 2.62-2.58 (m, 1H), 2.30-2.25 (m, 2H), 2.19-1.80 (s, 3H), 1.80-1.66 (m, 1H).

(3S,6S)-6-(2,3-Difluoro-5-nitrophenyl)-3-fluoro-3-(fluoromethyl)-6-methylpiperidin-2-one and (3R,6S)-6-(2,3-difluoro-5-nitrophenyl)-3-fluoro-3-(fluoromethyl)-6-methylpiperidin-2-one were prepared in a similar way from (6S)-6-(2,3-difluorophenyl)-3-fluoro-3-(fluoromethyl)-6-methylpiperidin-2-one (6S)-3-Fluoro-6-(2-fluoro-5-nitrophenyl)-3,6-bis(fluoromethyl)piperidin-2-one was prepared in a similar way from (6S)-3-fluoro-3,6-bis(fluoromethyl)-6-(2-fluorophenyl) piperidin-2-one Intermediate (3R,6S)-3-Fluoro-6-(2-fluoro-5-nitrophenyl)-3-(fluoromethyl)-6-methylpiperidine-2-thione

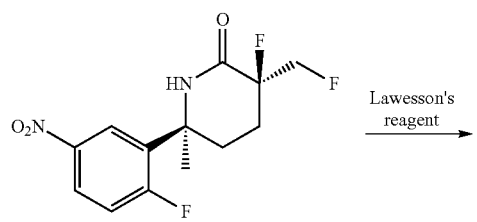

Lawesson's reagent

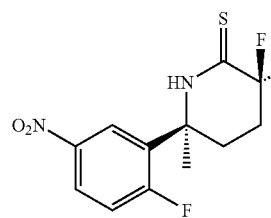

To a solution of (3S,6S)-3-fluoro-6-(2-fluoro-5-nitrophenyl)-3-(fluoromethyl)-6-methylpiperidin-2-one (900 mg, 3.0 mmol) in anhydrous toluene (18 mL) was added 2,4-bis(4-methoxyphenyl)-1,3,2,4-dithiadiphosphetane-2,4-dithione (Lawesson's reagent) (723 mg, 1.8 mmol). The mixture was stirred at 80° C. for 2 hours. The mixture was concentrated. The crude product was purified by flash chromatography with petroleum ether:ethyl acetate=3:1 to give (3R,6S)-3-fluoro-6-(2-fluoro-5-nitrophenyl)-3-(fluoromethyl)-6-methylpiperidine-2-thione (900 mg, 94.9% yield).

(3S,6S)-3-fluoro-6-(2-fluoro-5-nitrophenyl)-3-(fluoromethyl)-6-methylpiperidine-2-thione was prepared in a similar way from (3R,6S)-3-fluoro-6-(2-fluoro-5-nitrophenyl)-3-(fluoromethyl)-6-methylpiperidin-2-one (3R,6S)-6-(2,3-Difluoro-5-nitrophenyl)-3-fluoro-3-(fluoromethyl)-6-methylpiperidine-2-thione was prepared in a similar way from (3S,6S)-6-(2,3-difluoro-5-nitrophenyl)-3-fluoro-3-(fluoromethyl)-6-methylpiperidin-2-one (3S,6S)-6-(2,3-Difluoro-5-nitrophenyl)-3-fluoro-3-(fluoromethyl)-6-methylpiperidine-2-thione was prepared in a similar way from (3R,6S)-6-(2,3-difluoro-5-nitrophenyl)-3-fluoro-3-(fluoromethyl)-6-methylpiperidin-2-one (6S)-3-Fluoro-6-(2-fluoro-5-nitrophenyl)-3,6-bis(fluoromethyl)piperidine-2-thione was prepared in a similar way from (6S)-3-fluoro-6-(2-fluoro-5-nitrophenyl)-3,6-bis (fluoromethyl)piperidin-2-one Intermediate (3R,6S)-6-(5-Amino-2-fluorophenyl)-3-fluoro-3-(fluoromethyl)-6-methylpiperidine-2-thione

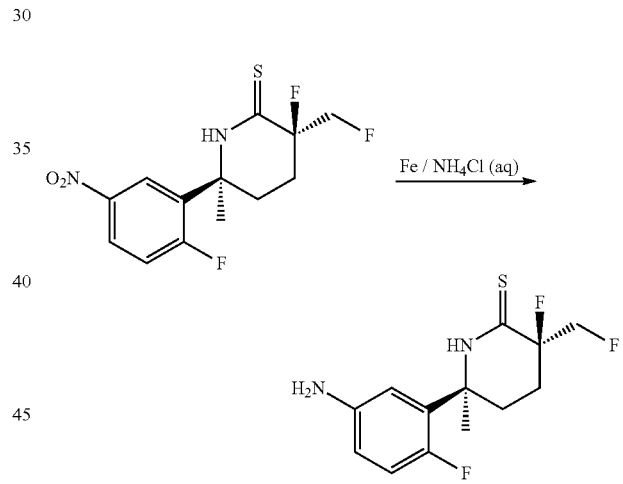

Fe / NH₄Cl (aq)

To a solution of (3R,6S)-3-fluoro-6-(2-fluoro-5-nitrophenyl)-3-(fluoromethyl)-6-methylpiperidine-2-thione (900 mg, 2.8 mmol) in EtOH (18.0 mL) and H₂O (4.5 mL) was added Fe (790 mg, 14.15 mmol) and NH₄Cl (756 mg, 14.2 mmol). The mixture was stirred at 20° C. for 5 hours. The mixture was filtered and the residue was washed with EtOH (30 mL). The combined filtrates were concentrated. The residue was dispersed in ethyl acetate (30 mL) and then filtered. The filter cake was washed with ethyl acetate (2×15 mL). The combined organic layers were concentrated. The crude product was purified by flash chromatography with petroleum ether:ethyl acetate=3:1 to give (3R,6S)-6-(5-amino-2-fluorophenyl)-3-fluoro-3-(fluoromethyl)-6-methylpiperidine-2-thione (712 mg, 87% yield). $^1$H NMR (600 MHz, CDCl₃) δ8.42 (s, 1H), 6.88 (dd, J=11.8, 8.6 Hz, 1H), 6.58 (dt, J=7.0, 3.2 Hz, 1H), 6.50 (dd, J=6.8, 2.8 Hz, 1H), 4.95 (ddd, J=49.0, 12.6, 10.9 Hz, 1H), 4.61 (ddd, J=46.7, 28.4, 10.7 Hz, 1H), 3.70 (s, 2H), 2.62-2.54 (m, 1H), 2.39-

2.30 (m, 1H), 2.10-2.02 (m, 1H), 1.91 (q, J=14.0 Hz, 1H), 1.70 (s, 3H). [α]$_D^{20}$ =−236° (c=0.10, EtOH).

(3S,6S)-6-(5-Amino-2-fluorophenyl)-3-fluoro-3-(fluoromethyl)-6-methylpiperidine-2-thione was prepared in a similar way from (3S,6S)-3-fluoro-6-(2-fluoro-5-nitrophenyl)-3-(fluoromethyl)-6-methylpiperidine-2-thione. $^1$H NMR (600 MHz, CDCl$_3$) δ8.58 (s, 1H), 6.88 (dd, J=11.7, 8.6 Hz, 1H), 6.58 (dt, J=8.4, 3.2 Hz, 1H), 6.38 (dd, J=6.7, 2.7 Hz, 1H), 4.97 (dt, J=48.8, 10.6 Hz, 1H), 4.60 (ddd, J=46.0, 24.6, 10.3 Hz, 1H), 3.68 (s, 2H), 2.53 (d, J=14.1 Hz, 1H), 2.26-2.17 (m, 1H), 2.13 (td, J=13.9, 2.6 Hz, 1H), 1.87-1.74 (m, 1H), 1.73 (s, 3H). [α]$_D^{20}$ =−154° (c=0.10, EtOH).

(3R,6S)-6-(5-Amino-2,3-difluorophenyl)-3-fluoro-3-(fluoromethyl)-6-methylpiperidine-2-thione was prepared in a similar way from (3R,6S)-6-(2,3-difluoro-5-nitrophenyl)-3-fluoro-3-(fluoromethyl)-6-methylpiperidine-2-thione (3S,6S)-6-(5-Amino-2,3-difluorophenyl)-3-fluoro-3-(fluoromethyl)-6-methylpiperidine-2-thione was prepared in a similar way from (3S,6S)-6-(2,3-difluoro-5-nitrophenyl)-3-fluoro-3-(fluoromethyl)-6-methylpiperidine-2-thione (3R,6S)-6-(5-Amino-2-fluorophenyl)-3-fluoro-3,6-bis(fluoromethyl)piperidine-2-thione and (3S,6S)-6-(5-amino-2-fluorophenyl)-3-fluoro-3,6-bis(fluoromethyl)piperidine-2-thione were prepared in a similar way starting from (6S)-3-fluoro-6-(2-fluoro-5-nitrophenyl)-3,6-bis(fluoromethyl)piperidine-2-thione followed by chromatographic separation of the two diastereomers.

(3R,6S)-6-(5-Amino-2-fluorophenyl)-3-fluoro-3,6-bis(fluoromethyl)piperidine-2-thione: $^1$H NMR (CDCl$_3$ 400 MHz) δ8.42 (s, 1H), 6.95-6.89 (m, 1H), 6.65-6.62 (m, 1H), 6.54 (dd, J=6.8, 3.2 Hz, 1H), 5.03-4.51 (m, 4H), 3.73 (s, 2H), 2.48-2.39 (m, 2H), 2.22 (t, J=14.0 Hz, 1H), 1.96 (q, J=12.8 Hz, 1H). [α]$_D^{20}$ =−204° (c=0.10, EtOH).

(3S,6S)-6-(5-Amino-2-fluorophenyl)-3-fluoro-3,6-bis(fluoromethyl)piperidine-2-thione: $^1$H NMR (CDCl$_3$ 400 MHz) δ8.65 (s, 1H), 6.95-6.90 (m, 1H), 6.64-6.62 (m, 1H), 6.41 (dd, J=6.8, 2.8 Hz, 1H), 5.09-4.95 (m, 2 H), 4.89-4.52 (m, 2H), 2.41-2.38 (m, 1H), 2.33-2.24 (m, 1H), 2.21-2.14 (m, 1H), 1.92-1.75 (m, 1H). [α]$_D^{20}$ =−130° (c=0.10, EtOH).

Intermediate

Methyl 5-(methoxy-d$_3$)picolinate

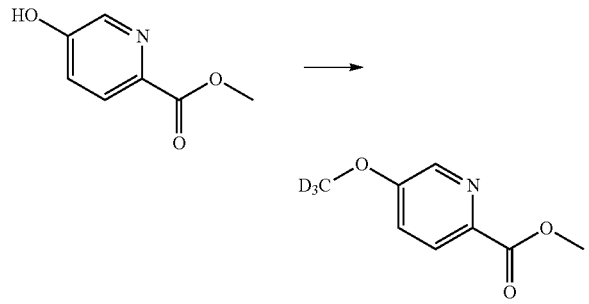

Methyl 5-hydroxypicolinate (2.88 g, 18.8 mmol) was dissolved in dimethylformamide (108 ml) under argon. Potassium carbonate (7.20 g, 52.1 mmol) was added and the orange suspension was stirred for 45 minutes at room temperature. Iodomethane-d$_3$ (1.41 ml, 22.6 mmol) was added. The reaction mixture was stirred for 2 hours. Water was added. The mixture was extracted with ethyl acetate. The organic phase was washed with brine, dried over MgSO$_4$ and concentrated in vacuo and purified by column chromatography on silica gel (heptane: ethyl acetate) to give methyl 5-(methoxy-d$_3$)picolinate.

Intermediate 5-(Methoxy-d$_3$)picolinic acid

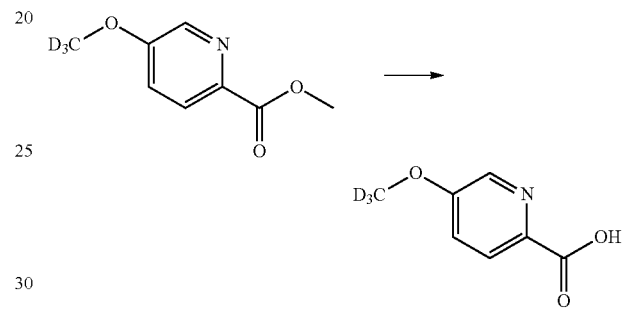

Methyl 5-(methoxy-d$_3$)picolinate (200 mg, 1.175 mmol) was dissolved in water (1.5 ml) and 1,4-dioxane (3 ml). Lithium hydroxide (70.4 mg, 2.94 mmol) was added and the reaction mixture was stirred for 1 hour. The reaction mixture was evaporated to about 2 ml and extracted with diethylether. The organic phase was extracted with 1 M NaOH and the combined aqueous phases were acidified to pH 2 with 6N HCl (aq). The mixture was cooled on an icebath and a precipitate was formed. The precipitate was colected to give 5-(methoxy-d$_3$)picolinic acid.

Stereochemistry

The relative stereochemistry of intermediate (3R,6S)-6-(5-amino-2-fluorophenyl)-3-fluoro-3-(fluoromethyl)-6-methylpiperidine-2-thione was assigned by 2D ROESY (rotating frame nuclear Overhauser effect spectroscopy) (Scheme 6). nOe (nuclear Overhauser effect) signals were observed between H(A) (δ4.61) and H(B) (δ2.10-2.02) and between H(B) (δ2.10-2.02) and H(D) (δ1.70) and an nOe signal was also observed between H(C) (δ4.61) and H(E) (δ6.58). Thus, the relative stereochemistry of intermediate (3R,6S)-6-(5-amino-2-fluorophenyl)-3-fluoro-3-(fluoromethyl)-6-methylpiperidine-2-thione is confirmed since no significant nOe's was observed between H(A) (δ4.60) and H(B) (δ2.53 or 2.13) in the 2D ROESY of (3S,6S)-6-(5-amino-2-fluorophenyl)-3-fluoro-3-(fluoromethyl)-6-methylpiperidine-2-thione. The relative stereochemistries of (3R, 6S)-6-(5-amino-2,3-difluorophenyl)-3-fluoro-3-(fluoromethyl)-6-methylpiperidine-2-thione, (3S,6S)-6-(5-amino-2,3-difluorophenyl)-3-fluoro-3-(fluoromethyl)-6-methylpiperidine-2-thione, (3R,6S)-6-(5-amino-2-fluorophenyl)-3-fluoro-3,6-bis(fluoromethyl)piperidine-2-thione and (3S,6S)-6-(5-amino-2-fluorophenyl)-3-fluoro-3,6-bis(fluoromethyl)piperidine-2-thione were assigned by analogy.

Scheme 6. nOe in ROESY of (3R,6S)-6-(5-amino-2-fluorophenyl)-3-fluoro-3-(fluoromethyl)-6-methylpiperidine-2-thione

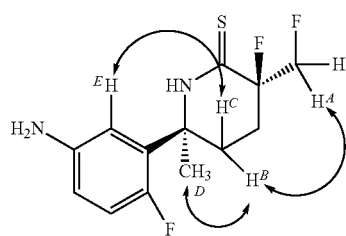

Preparation of Compounds of Formula I

Example 1

N-(3-((2S,5S)-6-Amino-5-fluoro-5-(fluoromethyl)-2-methyl-2,3,4,5-tetrahydropyridin-2-yl)-4-fluorophenyl)-5-methoxypicolinamide (Compound 1)

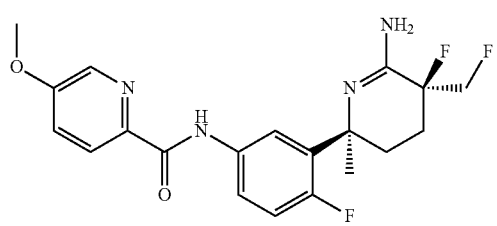 [SMILES: COc1ccc(C(=O)Nc2ccc(F)c([C@]3(C)CC[C@@](F)(CF)C(N)=N3)c2)nc1]

HATU (1-[bis(dimethylamino)methylene]-1H-1,2,3-triazolo[4,5-b]pyridinium 3-oxid hexafluorophosphate) (600 mg, 1.58 mmol) was added to 5-methoxypicolinic acid (242 mg, 1.58 mmol) in DMF (1 ml). The reaction mixture was stirred at room temperature for 5 minutes. (3R,6S)-6-(5-Amino-2-fluorophenyl)-3-fluoro-3-(fluoromethyl)-6-methylpiperidine-2-thione (350 mg, 1.21 mmol) was added followed by DIPEA (N,N-diisopropylethylamine) (1.06 ml, 6.07 mmol) and the reaction mixture was stirred at room temperature for 1 hour. Saturated ammonium chloride (aq) was added. The mixture was extracted with ethyl acetate. The organic phase was washed with brine, dried over magnesium sulfate and concentrated in vacuo. 7 M ammonia in methanol (3 mL, 21 mmol) was added and the reaction mixture was stirred in a sealed vial at 50° C. overnight. The reaction mixture was allowed to cool to room temperature and was concentrated in vacuo. The crude product was purified by flash chromatography on silica gel (eluent: heptane/ethyl acetate). The product was further purified by the following procedure: The product was dissolved in ethyl acetate (50 mL) and washed with a solution of saturated aqueous NaHCO$_3$/water (1/1). The organic phase was washed total of 10 times (using 10 mL each time). The organic phase was dried over MgSO$_4$, filtered, and evaporated to give N-(3-((2S,5S)-6-amino-5-fluoro-5-(fluoromethyl)-2-methyl-2,3,4,5-tetrahydropyridin-2-yl)-4-fluorophenyl)-5-methoxypicolinamide. $^1$H NMR (600 MHz, DMSO) δ10.38 (s, 1H), 8.39 (d, J=2.6 Hz, 1H), 8.12 (d, J=8.6 Hz, 1H), 7.84-7.76 (m, 2H), 7.62 (dd, J=8.7, 2.9 Hz, 1H), 7.13 (dd, J=11.9, 8.6 Hz, 1H), 6.10 (s, 2H), 4.94-4.68 (m, 2H), 3.93 (s, 3H), 2.16-2.03 (m, 2H), 1.971.87 (m, 1H), 1.641.53 (m, 1H), 1.46 (s, 3H). LC-MS (m/z) 407.1 (MH$^+$); t$_R$=0.51 (Method B)

Example 2

N-(3-((2S,5S)-6-Amino-5-fluoro-5-(fluoromethyl)-2-methyl-2,3,4,5-tetrahydropyridin-2-yl)-4-fluorophenyl)-5-(methoxy-d$_3$)picolinamide (Compound 2)

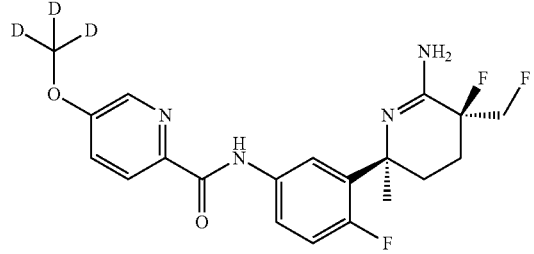 [SMILES: [2H]C([2H])([2H])Oc1ccc(C(=O)Nc2ccc(F)c([C@]3(C)CC[C@@](F)(CF)C(N)=N3)c2)nc1]

Prepared from (3R,6S)-6-(5-amino-2-fluorophenyl)-3-fluoro-3-(fluoromethyl)-6-methylpiperidine-2-thione and 5-(methoxy-d$_3$)picolinic acid $^1$H NMR (600 MHz, DMSO) δ10.35 (s, 1H), 8.39 (dd, J=2.9, 0.5 Hz, 1H), 8.12 (dd, J=8.7, 0.5 Hz, 1H), 7.84-7.77 (m, 2H), 7.61 (dd, J=8.7, 2.9 Hz, 1H), 7.12 (dd, J=11.9, 8.6 Hz, 1H), 6.24 (s, 2H), 4.96-4.74 (m, 2H), 2.16-2.05 (m, 2H), 1.99-1.89 (m, 1H), 1.66-1.55 (m, 1H), 1.47 (s, 3H). LC-MS (m/z) 410.2 (MH$^+$); t$_R$=0.5 (Method B)

Example 3

N-(3-((2S,5S)-6-Amino-5-fluoro-5-(fluoromethyl)-2-methyl-2,3,4,5-tetrahydropyridin-2-yl)-4-fluorophenyl)-5-cyano-3-methylpicolinamide (Compound 3)

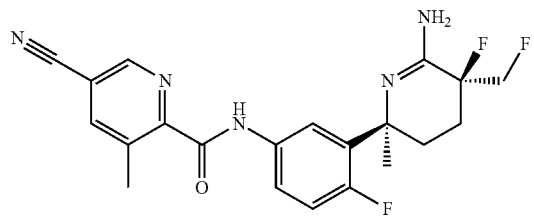 [SMILES: Cc1cc(C#N)cnc1C(=O)Nc1ccc(F)c([C@]2(C)CC[C@@](F)(CF)C(N)=N2)c1]

Prepared from (3R,6S)-6-(5-amino-2-fluorophenyl)-3-fluoro-3-(fluoromethyl)-6-methylpiperidine-2-thione and 5-cyano-3-methylpicolinic acid $^1$H NMR (600 MHz, DMSO) δ10.72 (s, 1H), 8.98 (s, 1H), 8.40 (s, 1H), 7.84-7.79 (m, 1H), 7.67 (dd, J=7.4, 2.6 Hz, 1H), 7.19-7.13 (m, 1H), 4.97-4.72 (m, 2H), 2.51 (s, 3H), 2.17-2.09 (m, 2H), 1.98-1.89 (m, 1H), 1.62-1.52 (m, 1H), 1.49 (s, 3H). LC-MS (m/z) 416.1 (MH$^+$); t$_R$=0.5 (Method A)

Example 4

N-(3-((2S,5S)-6-Amino-5-fluoro-5-(fluoromethyl)-2-methyl-2,3,4,5-tetrahydropyridin-2-yl)-4-fluorophenyl)-5-chloropicolinamide (Compound 4)

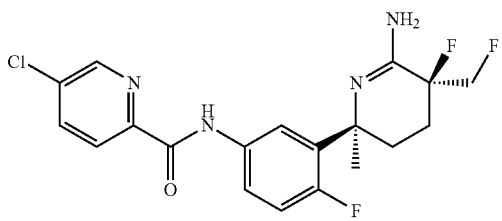 [SMILES: C[C@@]1(c2cc(NC(=O)c3ccc(Cl)cn3)ccc2F)CC[C@@](F)(CF)C(N)=N1]

Prepared from (3R,6S)-6-(5-amino-2-fluorophenyl)-3-fluoro-3-(fluoromethyl)-6-methylpiperidine-2-thione and 5-chloropicolinic acid $^1$H NMR (600 MHz, DMSO) δ10.61 (s, 1H), 8.78 (d, J=1.9 Hz, 1H), 8.20 (dd, J=8.4, 2.2 Hz, 1H), 8.15 (d, J=8.4 Hz, 1H), 7.86-7.82 (m, 1H), 7.82-7.78 (m, 1H), 7.14 (dd, J=11.7, 8.8 Hz, 1H), 6.17 (s, 2H), 4.97-4.66 (m, 2H), 2.16-2.05 (m, 2H), 1.97-1.89 (m, 1H), 1.65-1.55 (m, 1H), 1.47 (s, 3H). LC-MS (m/z) 411.1 (MH$^+$); $t_R$=0.53 (Method A)

Example 5

N-(3-((2S,5S)-6-Amino-5-fluoro-5-(fluoromethyl)-2-methyl-2,3,4,5-tetrahydropyridin-2-yl)-4-fluorophenyl)-5-methoxypyrazine-2-carboxamide (Compound 5)

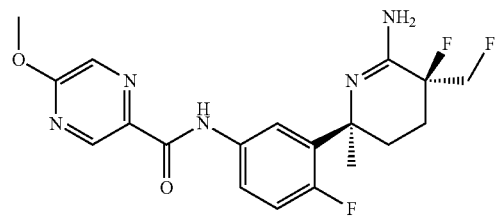 [SMILES: COc1cnc(C(=O)Nc2ccc(F)c([C@]3(C)CC[C@@](F)(CF)C(N)=N3)c2)cn1]

Prepared from (3R,6S)-6-(5-amino-2-fluorophenyl)-3-fluoro-3-(fluoromethyl)-6-methylpiperidine-2-thione and 5-methoxypyrazine-2-carboxylic acid $^1$H NMR (600 MHz, DMSO) δ10.45 (s, 1H), 8.88 (d, J=1.0 Hz, 1H), 8.41 (d, J=1.0 Hz, 1H), 7.83 (dd, J=7.3, 2.4 Hz, 1H), 7.78-7.74 (m, 1H), 7.13 (dd, J=11.8, 8.8 Hz, 1H), 6.12 (s, 2H), 4.96-4.68 (m, 2H), 4.02 (s, 3H), 2.26-2.04 (m, 2H), 1.96-1.89 (m, 1H), 1.64-1.53 (m, 1H), 1.46 (s, 3H). LC-MS (m/z) 408.1 (MH$^+$); $t_R$=0.48 (Method A)

Example 6

N-(3-((2S,5S)-6-Amino-5-fluoro-5-(fluoromethyl)-2-methyl-2,3,4,5-tetrahydropyridin-2-yl)-4-fluorophenyl)-2-methyloxazole-5-carboxamide (Compound 6)

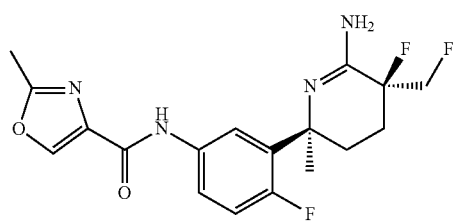 [SMILES: Cc1nc(C(=O)Nc2ccc(F)c([C@]3(C)CC[C@@](F)(CF)C(N)=N3)c2)co1]

Prepared from (3R,6S)-6-(5-amino-2-fluorophenyl)-3-fluoro-3-(fluoromethyl)-6-methylpiperidine-2-thione and 2-methyloxazole-4-carboxylic acid $^1$H NMR (600 MHz, DMSO) δ10.09 (s, 1H), 8.62 (s, 1H), 7.76 (dd, J=7.5, 2.7 Hz, 1H), 7.70-7.65 (m, 1H), 7.10 (dd, J=11.9, 8.7 Hz, 1H), 6.08 (s, 2H), 4.94-4.68 (m, 2H), 2.50 (s, 3H), 2.14-2.04 (m, 2H), 1.95-1.87 (m, 1H), 1.60-1.52 (m, 1H), 1.46 (s, 3H). LC-MS (m/z) 381.1 (MH$^+$); $t_R$=0.43 (Method A)

Example 7

N-(3-((2S,5S)-6-Amino-5-fluoro-5-(fluoromethyl)-2-methyl-2,3,4,5-tetrahydropyridin-2-yl)-4-fluorophenyl)-4-bromo-1-methyl-1H-imidazole-2-carboxamide (Compound 7)

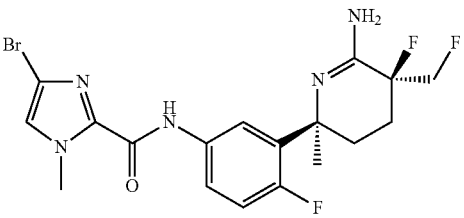 [SMILES: Cn1cc(Br)nc1C(=O)Nc1ccc(F)c([C@]2(C)CC[C@@](F)(CF)C(N)=N2)c1]

Prepared from (3R,6S)-6-(5-amino-2-fluorophenyl)-3-fluoro-3-(fluoromethyl)-6-methylpiperidine-2-thione and 4-bromo-1-methyl-1H-imidazole-2-carboxylic acid $^1$H NMR (600 MHz, DMSO) δ10.40 (s, 1H), 7.77 (dd, J=14.3, 9.2 Hz, 1H), 7.70-7.65 (m, 1H), 7.63 (s, 1H), 7.10 (dd, J=11.8, 8.8 Hz, 1H), 6.10 (s, 2H), 4.95-4.68 (m, 2H), 3.96 (s, 3H), 2.15-2.02 (m, 2H), 1.95-1.85 (m, 1H), 1.64-1.53 (m, 1H), 1.45 (s, 3H). LC-MS (m/z) 460 (MH$^+$); $t_R$=0.51 (Method A)

Example 8

N-(3-((2S,5S)-6-Amino-5-fluoro-5-(fluoromethyl)-2-methyl-2,3,4,5-tetrahydropyridin-2-yl)-4-fluorophenyl)-4-methylthiazole-2-carboxamide (Compound 8)

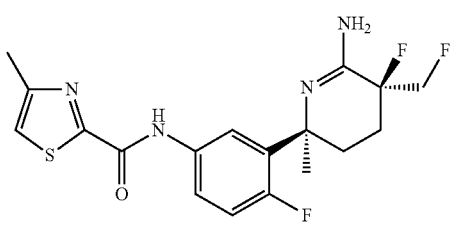 [SMILES: Cc1csc(C(=O)Nc2ccc(F)c([C@]3(C)CC[C@@](F)(CF)C(N)=N3)c2)n1]

Prepared from (3R,6S)-6-(5-amino-2-fluorophenyl)-3-fluoro-3-(fluoromethyl)-6-methylpiperidine-2-thione and 4-methylthiazole-2-carboxylic acid $^1$H NMR (600 MHz, DMSO) δ10.72 (s, 1H), 7.87 (dd, J=7.4, 2.5 Hz, 1H), 7.73-7.67 (m, 2H), 7.12 (dd, J=11.8, 8.8 Hz, 1H), 6.12 (s, 2H), 4.97-4.68 (m, 2H), 2.50 (s, s 3H), 2.15-2.04 (m, 2H), 1.95-1.87 (m, 1H), 1.63-1.52 (m, 1H), 1.46 (s, 3H). LC-MS (m/z) 397.1 (MH$^+$); $t_R$=0.49 (Method A)

Example 9

N-(3-((2S,5S)-6-Amino-5-fluoro-5-(fluoromethyl)-2-methyl-2,3,4,5-tetrahydropyridin-2-yl)-4-fluorophenyl)-2-(difluoromethyhoxazole-4-carboxamide (Compound 9)

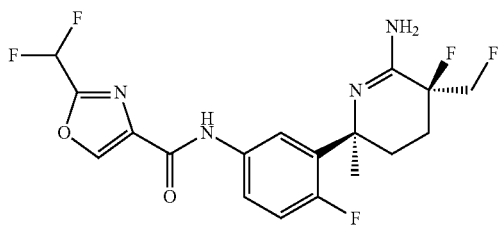 [SMILES: C[C@@]1(c2cc(NC(=O)c3coc(C(F)F)n3)ccc2F)CC[C@@](F)(CF)C(N)=N1]

Prepared from (3R,6S)-6-(5-amino-2-fluorophenyl)-3-fluoro-3-(fluoromethyl)-6-methylpiperidine-2-thione and 2-(difluoromethyl)oxazole-4-carboxylic acid $^1$H NMR (600 MHz, DMSO) δ10.40 (s, 1H), 9.04-8.99 (m, 1H), 7.75 (dd, J=11.8, 6.7 Hz, 1H), 7.71-7.64 (m, 1H), 7.34 (t, J=51.9 Hz, 1H), 7.12 (dd, J=11.7, 8.9 Hz, 1H), 6.10 (s, 2H), 4.96-4.68 (m, 2H), 2.16-2.03 (m, 2H), 1.961.86 (m, 1H), 1.62-1.52 (m, 1H), 1.46 (s, 3H). LC-MS (m/z) 417.1 (MH$^+$); $t_R$=0.46 (Method A)

Example 10

N-(3-((2S,5S)-6-Amino-5-fluoro-5-(fluoromethyl)-2-methyl-2,3,4,5-tetrahydropyridin-2-yl)-4-fluorophenyl)-1-(difluoromethyl)-1H-imidazole-4-carboxamide (Compound 10)

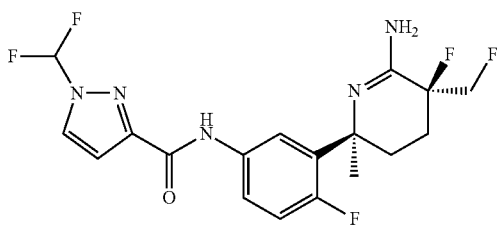 [SMILES: C[C@@]1(c2cc(NC(=O)c3ccn(C(F)F)n3)ccc2F)CC[C@@](F)(CF)C(N)=N1]

Prepared from (3R,6S)-6-(5-amino-2-fluorophenyl)-3-fluoro-3-(fluoromethyl)-6-methylpiperidine-2-thione and 1-(difluoromethyl)-1H-pyrazole-3-carboxylic acid $^1$H NMR (600 MHz, DMSO) δ10.36 (s, 1H), 8.41 (d, J=2.5 Hz, 1H), 7.92 (t, J=58.7 Hz, 1H), 7.76 (dd, J=7.1, 2.1 Hz, 1H), 7.71-7.66 (m, 1H), 7.12 (dd, J=11.7, 8.9 Hz, 1H), 7.01 (d, J=2.5 Hz, 1H), 6.08 (s, 2H), 4.96-4.69 (m, 2H), 2.15-2.03 (m, 2H), 1.97-1.87 (m, 1H), 1.64-1.53 (m, 1H), 1.46 (s, 3H). LC-MS (m/z) 416.1 (MH$^+$); $t_R$=0.46 (Method A)

Example 11

N-(3-((2S,5S)-6-Amino-5-fluoro-5-(fluoromethyl)-2-methyl-2,3,4,5-tetrahydropyridin-2-yl)-4-fluorophenyl)-5-(difluoromethyppyrazine-2-carboxamide (Compound 11)

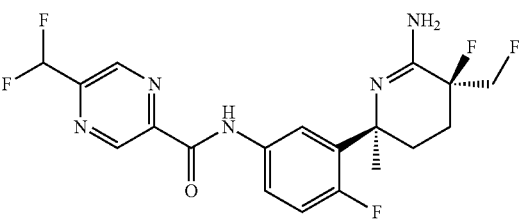 [SMILES: C[C@@]1(c2cc(NC(=O)c3cnc(C(F)F)cn3)ccc2F)CC[C@@](F)(CF)C(N)=N1]

Prepared from (3R,6S)-6-(5-amino-2-fluorophenyl)-3-fluoro-3-(fluoromethyl)-6-methylpiperidine-2-thione and 5-(difluoromethyl)pyrazine-2-carboxylic acid $^1$H NMR (600 MHz, DMSO) δ10.88 (s, 1H), 9.38 (s, 1H), 9.09 (s, 1H), 7.89 (dd, J=7.3, 2.4 Hz, 1H), 7.83-7.77 (m, 1H), 7.27 (t, J=51.0 Hz, 2H), 7.18-7.13 (m, 1H), 6.16 (s, 2H), 4.96-4.69 (m, 2H), 2.15-2.07 (m, 2H), 1.97-1.88 (m, 1H), 1.62-1.54 (m, 1H), 1.48 (s, 3H). LC-MS (m/z) 428.1 (MH$^+$); $t_R$=0.48 (Method A)

Example 12

N-(3-((2S,5S)-6-Amino-5-fluoro-5-(fluoromethyl)-2-methyl-2,3,4,5-tetrahydropyridin-2-yl)-4-fluorophenyl)-4-chlorobenzamide (Compound 12)

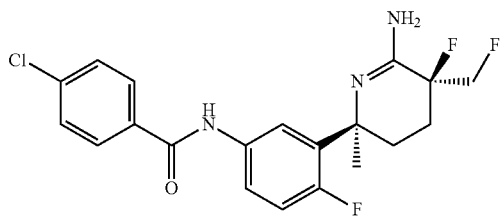 [SMILES: C[C@@]1(c2cc(NC(=O)c3ccc(Cl)cc3)ccc2F)CC[C@@](F)(CF)C(N)=N1]

Prepared from (3R,6S)-6-(5-amino-2-fluorophenyl)-3-fluoro-3-(fluoromethyl)-6-methylpiperidine-2-thione and 4-chlorobenzoic acid $^1$H NMR (600 MHz, DMSO) δ10.42 (s, 1H), 7.98 (d, J=8.3 Hz, 2H), 7.70 (d, J=5.7 Hz, 2H), 7.60 (d, J=8.4 Hz, 2H), 7.13 (dd, J=11.5, 9.1 Hz, 1H), 6.09 (s, 2H), 4.96-4.68 (m, 2H), 2.17-2.05 (m, 2H), 1.98-1.89 (m, 1H), 1.64-1.52 (m, 1H), 1.46 (s, 3H). LC-MS (m/z) 410.1 (MH$^+$); $t_R$=0.54 (Method A)

Example 13

N-(3-((2S,5S)-6-Amino-5-fluoro-5-(fluoromethyl)-2-methyl-2,3,4,5-tetrahydropyridin-2-yl)-4-fluorophenyl)-5-fluoropicolinamide (Compound 13)

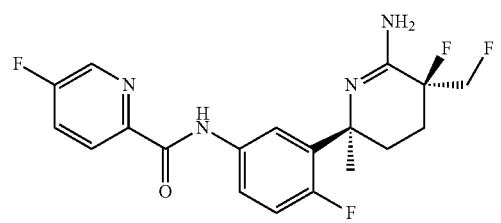 [SMILES: C[C@@]1(c2cc(NC(=O)c3ccc(F)cn3)ccc2F)CC[C@@](F)(CF)C(N)=N1]

Prepared from (3R,6S)-6-(5-amino-2-fluorophenyl)-3-fluoro-3-(fluoromethyl)-6-methylpiperidine-2-thione and 5-fluoropicolinic acid $^1$H NMR (600 MHz, DMSO) δ11.11 (s, 1H), 10.92 (s, 1H), 9.88 (s, 1H), 9.73 (s, 1H), 8.75 (d, J=2.2 Hz, 1H), 8.24 (dd, J=8.7, 4.6 Hz, 1H), 8.05-8.01 (m, 1H), 7.99 (dd, J=8.7, 2.8 Hz, 1H), 7.91 (dd, J=7.6, 2.4 Hz, 1H), 7.30 (dd, J=12.1, 8.9 Hz, 1H), 5.19-4.94 (m, 2H), 2.39 (d, J=12.8 Hz, 1H), 2.36-2.29 (m, 1H), 2.15 (t, J=13.8 Hz, 1H), 1.79-1.71 (m, 4H). LC-MS (m/z) 395.1 (MH$^+$); $t_R$=0.49 (Method A)

Example 14

N-(3-((2S,5R)-6-Amino-5-fluoro-5-(fluoromethyl)-2-methyl-2,3,4,5-tetrahydropyridin-2-yl)-4-fluorophenyl)-5-methoxypicolinamide (Compound 14)

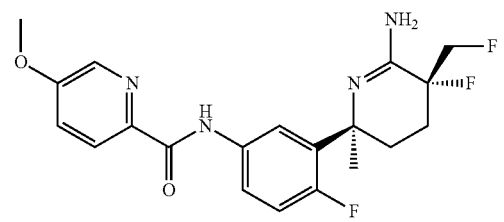 [SMILES: COc1ccc(C(=O)Nc2ccc(F)c([C@]3(C)CC[C@](F)(CF)C(N)=N3)c2)nc1]

Prepared from (3S,6S)-6-(5-amino-2-fluorophenyl)-3-fluoro-3-(fluoromethyl)-6-methylpiperidine-2-thione and 5-methoxypicolinic acid LC-MS (m/z) 407 (MH$^+$); $t_R$=0.5 (Method B)

Example 15

N-[3-[(2S,5S)-6-Amino-5-fluoro-5-(fluoromethyl)-2-methyl-2,3,4,5-tetrahydropyridin-2-yl]-4,5-difluoro-phenyl]-5-fluoro-pyridine-2-carboxamide (Compound 15)

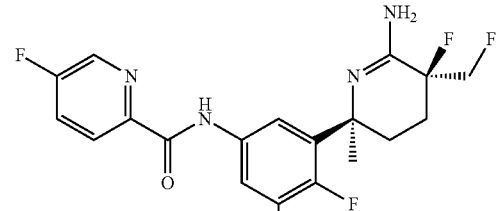

Prepared from (3R,6S)-6-(5-amino-2,3-difluorophenyl)-3-fluoro-3-(fluoromethyl)-6-methylpiperidine-2-thione and 5-fluoropicolinic acid $^1$H NMR (400 MHz, CDCl$_3$): δ 9.83 (s, 1H), 8.45 (d, J=2.8 Hz, 1H), 8.32 (q, J=4.4 Hz, 1H), 8.11-8.06 (m, 1H), 7.60 (td, J=8.0, 2.8 Hz, 1H), 7.17 (dt, J=5.6, 2.4 Hz, 1H), 4.80-4.55 (m, 2H), 3.49 (brs, 2H), 2.50-2.44 (m, 1H), 2.19-2.12 (m, 1H), 1.93 (td, J=14.0, 2.0 Hz, 1H), 1.80-1.68 (m, 1H), 1.63 (s, 3H). LC-MS (m/z) 413.1 (MH$^+$); $t_R$=2.07 min (Method C) $[α]_D^{20}$=−10.00 (589 nm, c=0.10, MeOH).

Example 16

N-[3-[(2S,5S)-6-Amino-5-fluoro-5-(fluoromethyl)-2-methyl-2,3,4,5-tetrahydropyridin-2-yl]-4,5-difluoro-phenyl]-5-methoxy-pyridine-2-carboxamide (Compound 16)

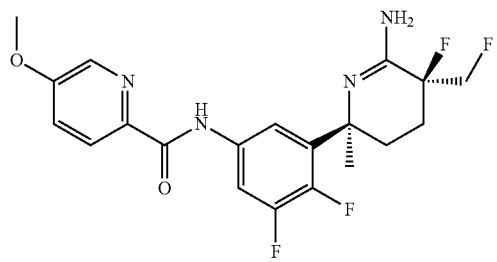 [SMILES: COc1ccc(C(=O)Nc2cc(F)c(F)c([C@]3(C)CC[C@@](F)(CF)C(N)=N3)c2)nc1]

Prepared from (3R,6S)-6-(5-amino-2,3-difluorophenyl)-3-fluoro-3-(fluoromethyl)-6-methylpiperidine-2-thione and 5-methoxypicolinic acid $^1$H NMR (400 MHz, CDCl$_3$): δ 9.86 (s, 1H), 8.26 (d, J=2.8 Hz, 1H), 8.22 (d, J=8.4 Hz, 1H), 8.14-8.08(m, 1H), 7.34 (dd, J=8.8, 3.2 Hz, 1H), 7.15 (dt, J=6.0, 2.0 Hz, 1H), 4.80-4.55 (m, 2H), 3.95 (s, 3H), 3.38 (brs, 2H), 2.50-2.44 (m, 1H), 2.20-2.13 (m, 1H), 1.93 (td, J=13.8, 2.0 Hz, 1H), 1.80-1.68 (m, 1H), 1.62 (d, J=1.2 Hz, 3H). LC-MS (m/z) 425.1 (MH$^+$); t$_R$=2.10 min (Method C) [α]$_D^{20}$ =+13.00 (589 nm, c=0.10, MeOH).

Example 17

N-[3-[(2S,5S)-6-Amino-5-fluoro-5-(fluoromethyl)-2-methyl-2,3,4,5-tetrahydropyridin-2-yl]-4,5-difluoro-phenyl]-5-methoxy-pyridine-2-carboxamide (Compound 17)

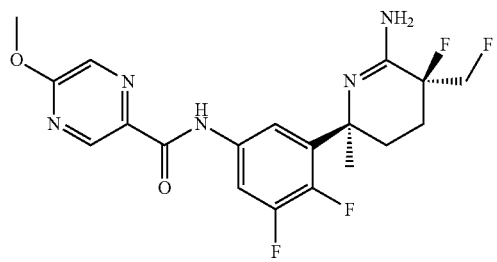 [SMILES: COc1cnc(C(=O)Nc2cc(F)c(F)c([C@]3(C)CC[C@@](F)(CF)C(N)=N3)c2)cn1]

Prepared from (3R,6S)-6-(5-amino-2,3-difluorophenyl)-3-fluoro-3-(fluoromethyl)-6-methylpiperidine-2-thione and 5-methoxypyrazine-2-carboxylic acid $^1$H NMR (400 MHz, CDCl$_3$): δ 9.54 (s, 1H), 9.00 (d, J=1.6 Hz, 1H), 9.15 (d, J=1.6 Hz, 1H), 8.13-8.07 (m, 1H), 7.14 (dt, J=6.0, 2.0 Hz, 1H), 4.81-4.56 (m, 2H), 4.08 (s, 3H), 3.05 (brs, 2H), 2.53-2.46 (m, 1H), 2.20-2.13 (m, 1H), 1.94 (td, J=13.6, 2.4 Hz, 1H), 1.82-1.70 (m, 1H), 1.64 (d, J=1.2 Hz, 3H). LC-MS (m/z) 426.1 (MH$^+$); t$_R$=2.07 (Method C) [α]$_D^{20}$ =+12.00 (589 nm, c=0.10, MeOH).

Example 18

N-[3-[(2S,5R)-6-Amino-5-fluoro-5-(fluoromethyl)-2-methyl-2,3,4,5-tetrahydropyridin-2-yl]-4,5-difluoro-phenyl]-5-fluoro-pyridine-2-carboxamide (Compound 18)

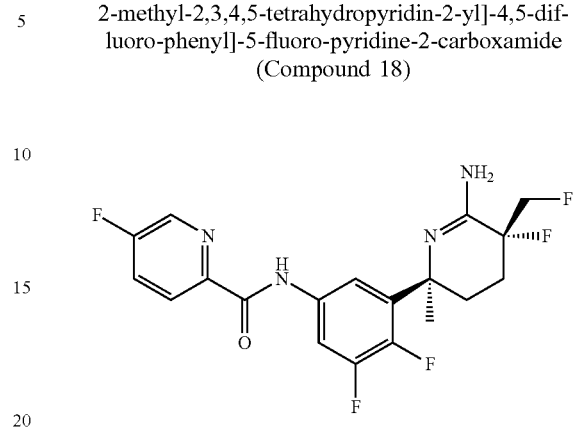

Prepared from (3S,6S)-6-(5-amino-2,3-difluorophenyl)-3-fluoro-3-(fluoromethyl)-6-methylpiperidine-2-thione and 5-fluoropicolinic acid $^1$H NMR (400 MHz, CDCl$_3$): δ 9.80 (s, 1H), 8.46 (d, J=2.8 Hz, 1H), 8.32 (q, J=4.4 Hz, 1H), 7.98-7.92 (m, 1H), 7.61 (td, J=8.0, 2.8 Hz, 1H), 7.19(dt, J=6.0, 2.4 Hz, 1H), 4.69-4.41 (m, 2H), 3.29 (brs, 2H), 2.19 (d, J=5.6 Hz, 2H), 2.14-2.06 (m, 1H), 1.95-1.84 (m, 1H), 1.66 (s, 3H). LC-MS (m/z) 413.1 (MH+); t$_R$=2.07 (Method C) [α]$_D^{20}$ =+9.00 (589 nm, c=0.10, MeOH).

Example 19

N-[3-[(2S,5R)-6-Amino-5-fluoro-5-(fluoromethyl)-2-methyl-2,3,4,5-tetrahydropyridin-2-yl]-4,5-difluoro-phenyl]-5-methoxy-pyridine-2-carboxamide (Compound 19)

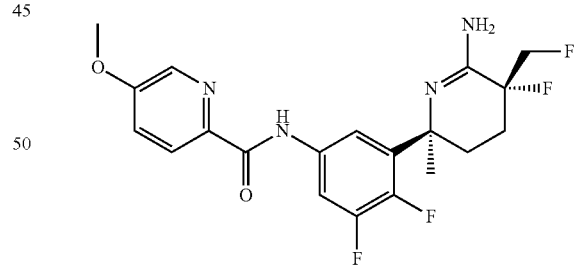

Prepared from (3S,6S)-6-(5-amino-2,3-difluorophenyl)-3-fluoro-3-(fluoromethyl)-6-methylpiperidine-2-thione and 5-methoxypicolinic acid $^1$H NMR (400 MHz, CDCl$_3$): δ 9.83 (s, 1H), 8.26 (d, J=2.8 Hz, 1H), 8.22 (d, J=8.4 Hz, 1H), 7.99-7.94 (m, 1H), 7.34 (dd, J=8.4, 2.4 Hz, 1H), 7.17 (dt, J=5.6, 2.0 Hz, 1H), 4.69-4.41 (m, 2H), 3.95 (s, 3H), 3.49 (brs, 2H), 2.18 (d, J=6.0 Hz, 2H), 2.13-2.05 (m, 1H), 1.94-1.83 (m, 1H), 1.65 (s, 3H). LC-MS (m/z) 425.1 (MH$^+$); t$_R$=2.10 (Method C) [α]$_D^{20}$ =+11.00 (589 nm, c=0.10, MeOH).

Example 20

N-[3-[(2S,5R)-6-Amino-5-fluoro-5-(fluoromethyl)-2-methyl-2,3,4,5-tetrahydropyridin-2-yl]-4,5-difluoro-phenyl]-5-methoxy-pyrazine-2-carboxamide (Compound 20)

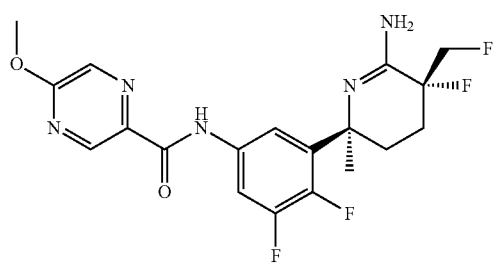 [SMILES: COc1cnc(C(=O)Nc2cc(F)c(F)c([C@]3(C)CC[C@](F)(CF)C(N)=N3)c2)cn1]

Prepared from (3S,6S)-6-(5-amino-2,3-difluorophenyl)-3-fluoro-3-(fluoromethyl)-6-methylpiperidine-2-thione and 5-methoxypyrazine-2-carboxylic acid $^1$H NMR (400 MHz, CDCl$_3$): δ 9.51 (s, 1H), 9.00 (d, J=1.2 Hz, 1H), 8.16 (d, J=1.2 Hz, 1H), 7.98-7.93 (m, 1H), 7.16 (dt, J=5.6, 2.4 Hz, 1H), 4.70-4.43 (m, 2H), 4.08 (s, 3H), 2.80 (brs, 2H), 2.20 (dd, J=8.4, 4.0 Hz, 2H), 2.15-2.09 (m, 1H), 1.94-1.82 (m, 1H), 1.68 (s, 3H). LC-MS (m/z) 426.1 (MH$^+$); t$_R$=2.07 (Method C) [α]$_D^{20}$ =−9.00 (589 nm, c=0.10, MeOH).

Example 21

N-[3-[(2S,5S)-6-amino-5-fluoro-2,5-bis(fluoromethyl)-2,3,4,5-tetrahydropyridin-2-yl]-4-fluoro-phenyl]-5-fluoro-pyridine-2-carboxamide (Compound 21)

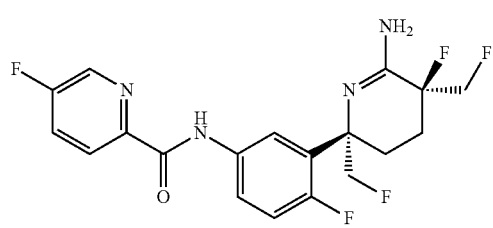 [SMILES: NC1=N[C@](CF)(c2cc(NC(=O)c3ccc(F)cn3)ccc2F)CC[C@@]1(F)CF]

Prepared from (3R,6S)-6-(5-amino-2-fluorophenyl)-3-fluoro-3,6-bis (fluoromethyl)piperidine-2-thione and 5-fluoropicolinic acid $^1$H NMR (400 MHz, CDCl$_3$) δ 9.85 (s, 1H), 8.48-8.47 (m, 1H), 8.34 (dd, J=8.8, 4.4 Hz, 1H), 8.02-7.98 (m, 1H), 7.63-7.58 (m, 2H), 7.10 (dd, J=11.6, 8.8 Hz, 1H), 4.87-4.82 (m, 1H), 4.77-4.64 (m, 2H), 4.49 (dd, J=48.0, 8.0 Hz 1H), 2.22-2.38 (m, 1H), 2.26-2.19 (m, 2H), 1.77 (br, s, 1H). LC-MS (m/z) 413.1 (MH$^+$); t$_R$=1.92 (Method C).

Example 22

N-[3-[(2S,5S)-6-amino-5-fluoro-2,5-bis(fluoromethyl)-2,3,4,5-tetrahydropyridin-2-yl]-4-fluoro-phenyl]-5-methoxy-pyridine-2-carboxamide (Compound 22)

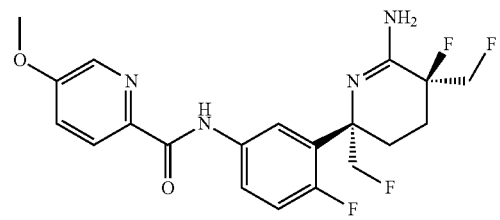 [SMILES: COc1ccc(C(=O)Nc2ccc(F)c([C@]3(CF)CC[C@@](F)(CF)C(N)=N3)c2)nc1]

Prepared from (3R,6S)-6-(5-amino-2-fluorophenyl)-3-fluoro-3,6-bis (fluoromethyl)piperidine-2-thione and 5-methoxypicolinic acid $^1$H NMR (400 MHz, CDCl$_3$) δ 9.87 (s, 1H), 8.28-8.23 (m, 2H), 8.01-7.99 (m, 1H), 7.59 (d, J=4.0 Hz, 1H), 7.09 (dd, J=11.8, 8.8 Hz 1H), 4.87-4.82 (m, 1H), 4.76-4.64 (m, 2H), 4.48 (dd, J=47.6, 8.8 Hz, 1H), 3.91 (t, J=9.6 Hz, 2H), 3.95 (s, 3H), 2.43-2.37 (m, 1H), 2.26-2.18 (m, 1H), 1.84-1.77 (m, 1H). LC-MS (m/z) 425.1 (MH$^+$); t$_R$=1.95 (Method C).

Example 23

N-[3-[(2S,5S)-6-amino-5-fluoro-2,5-bis(fluoromethyl)-2,3,4,5-tetrahydropyridin-2-yl]-4-fluoro-phenyl]-5-methoxy-pyrazine-2-carboxamide (Compound 23)

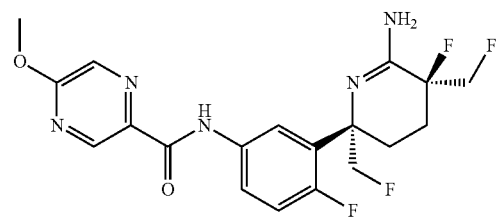 [SMILES: COc1cnc(C(=O)Nc2ccc(F)c([C@]3(CF)CC[C@@](F)(CF)C(N)=N3)c2)cn1]

Prepared from (3R,6S)-6-(5-amino-2-fluorophenyl)-3-fluoro-3,6-bis (fluoromethyl)piperidine-2-thione and 5-methoxypyrazine-2-carboxylic acid $^1$H NMR (400 MHz, CDCl$_3$) δ 9.46 (s, 1H), 8.94 (s, 1H), 8.08 (s, 1H), 7.93-7.89 (m, 1H), 7.50 (dd, J=7.2, 2.8Hz, 1 Hz), 7.02 (dd, J=11.6, 8.8Hz, 1H), 4.78-4.74 (m, 1H), 4.68-4.55 (m, 2H), 4.40 (dd, J=47.4, 8.8 Hz, 1H), 4.00 (s, 3H), 2.32-2.27 (m, 1H), 2.17-2.09 (m, 2H), 1.74-1.63 (m, 1H). LC-MS (m/z) 426.1 (MH$^+$); t$_R$=1.9 (Method C).

Example 24

N-[3-[(2S,5R)-6-amino-5-fluoro-2,5-bis(fluoromethyl)-2,3,4,5-tetrahydropyridin-2-yl]-4-fluoro-phenyl]-5-fluoro-pyridine-2-carboxamide (Compound 24)

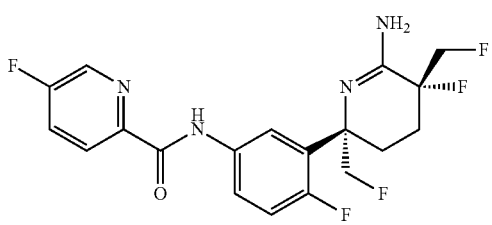 [SMILES: NC1=N[C@](CF)(c2cc(NC(=O)c3ccc(F)cn3)ccc2F)CC[C@]1(F)CF]

Prepared from (3R,6S)-6-(5-amino-2-fluorophenyl)-3-fluoro-3,6-bis(fluoromethyl)piperidine-2-thione and 5-fluoropicolinic acid $^1$H NMR (400 MHz, CDCl$_3$) δ 9.80 (s, 1H), 8.46 (d, J=2.4 Hz 1H), 8.34-8.31 (m, 1H), 7.87-7.84 (m, 1H), 7.62-7.58 (m, 2H), 7.11-7.06 (m, 1H), 4.79-4.50 (m, 4H), 2.37-2.32 (m, 1H), 2.26-2.21 (m, 2H), 1.87-1.82 (m, 1H). LC-MS (m/z) 413.1 (MH$^+$); $t_R$=1.9 (Method C).

Example 25

N-[3-[(2S,5R)-6-amino-5-fluoro-2,5-bis(fluoromethyl)-2,3,4,5-tetrahydropyridin-2-yl]-4-fluoro-phenyl]-5-methoxy-pyridine-2-carboxamide (Compound 25)

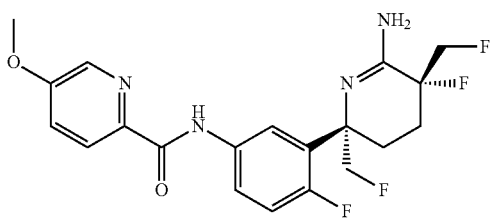 [SMILES: COc1ccc(C(=O)Nc2ccc(F)c([C@]3(CF)CC[C@](F)(CF)C(N)=N3)c2)nc1]

Prepared from (3R,6S)-6-(5-amino-2-fluorophenyl)-3-fluoro-3,6-bis(fluoromethyl)piperidine-2-thione and 5-methoxypicolinic acid $^1$H NMR (400 MHz, CDCl$_3$) δ 9.82 (s, 1H), 8.26-8.22 (m, 2H), 7.88-7.86 (m, 1H), 7.58-7.56 (m, 1H), 7.33 (dd, J=8.6, 2.0 Hz 1H), 7.07 (dd, J=11.6, 9.2 Hz, 1H), 4.79-4.38 (m, 4H), 3.94 (s, 3H), 2.36-2.31 (m, 1H), 2.26-2.10 (m, 2H), 1.90-1.78 (m, 1H). LC-MS (m/z) 425.1 (MH$^+$); $t_R$=2.26 (Method D).

Example 26

N-[3-[(2S,5R)-6-amino-5-fluoro-2,5-bis(fluoromethyl)-2,3,4,5-tetrahydropyridin-2-yl]-4-fluoro-phenyl]-5-methoxy-pyrazine-2-carboxamide (Compound 26)

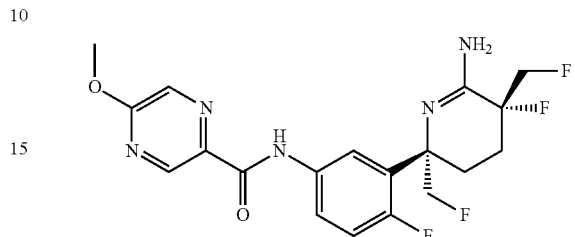

Prepared from (3R,6S)-6-(5-amino-2-fluorophenyl)-3-fluoro-3,6-bis(fluoromethyl)piperidine-2-thione and 5-methoxypyrazine-2-carboxylic acid $^1$H NMR (400 MHz, CDCl$_3$) δ 9.50 (s, 1H), 9.01 (s, 1H), 8.16 (s, 1H), 7.88-7.86 (m, 1H), 7.55 (dd, J=6.8, 2.0 Hz, 1H), 7.11-7.06 (m, 1H), 4.80-4.50 (m, 4H), 4.08 (s, 3H), 2.40-2.34 (m, 1H), 2.27-2.12 (m, 2H), 1.92-1.79(m, 1H). LC-MS (m/z) 426.1 (MH$^+$); $t_R$=2.21 (Method D).

Pharmacoloqical Testing

BACE1 Bindinq Assay

The binding assay was performed as SPA-based assay using a biotinylated form of human BACE1 recombinantly expressed and subsequently purified from Freestyle HEK293 cells. The binding assay was run in a 50 mM sodium acetate buffer, pH 4.5 containing 50 mM NaCl and 0.03% Tween-20 in white clear bottom 384 plates (Corning #3653). 10 nM (final concentration) radioligand ([$^3$H]-N-((1S,2R)-1-benzyl-3-cyclopropylamino-2-hydroxy-propyl)-5-(methanesulfonyl-methyl-amino)-N-((R)-1-phenyl-ethyl)-isophthalamide) (TRQ11569 purchased from GE Healthcare) was mixed with test compound at a given concentration, 6 nM (final concentration) human BACE1 and 25 µg Streptavidin coated PVT core SPA beads (RPNQ0007, GE Healthcare Life Sciences) in a total volume of 40 µl. Several concentrations of each test compound were tested in the assay for IC$_{50}$ determination. The plates were incubated for one hour at room temperature and counted in a Wallac Trilux counter. Total and non-specific binding were determined using buffer and 1 µM (final concentration) of the high affinity BACE1 reference inhibitor (S)-6-[3-chloro-5-(5-prop-1-ynyl-pyridin-3-yl)-thiophen-2-yl]-2-imino-3,6-dimethyl-tetrahydro-pyrimidin-4-one, respectively. For each test compound, a IC$_{50}$ value (the concentration mediating 50% inhibition of the specific binding of the radioligand) was determined from concentration-response curve and used to calculate the K$_i$ from the equation K$_i$=IC$_{50}$/(1+L/K$_d$), where L and K$_d$ are the final concentration of the radioligand used in the assay and the dissociation constant of the radioligand, respectively. The K$_d$ of the radioligand was determined from saturation binding experiments.

TABLE 1 binding affinity of selected compounds

| Compound | BACE1 |
|---|---|
| 1 | 22 |
| 2 | 20 |
| 3 | 10 |
| 4 | 11 |
| 5 | 24 |
| 6 | 46 |
| 7 | 67 |
| 8 | 62 |
| 9 | 26 |
| 10 | 22 |
| 11 | 55 |
| 12 | 140 |
| 13 | 40 |
| 14 | 130 |
| 15 | 52 |
| 16 | 27 |
| 17 | 42 |
| 18 | 300 |
| 19 | 130 |
| 20 | 230 |
| 21 | 67 |
| 22 | 28 |
| 23 | 17 |
| 24 | 180 |
| 25 | 160 |
| 26 | 160 |

BACE1 Efficacy Assay

The efficacy assay was performed as a FRET-based assay using a commercially available BACE1 kit (Life Technologies, P2985). 2 µl test compound at 10 µM (final concentration) and 15 µl BACE1 enzyme from the kit (final concentration 3 nM) were preincubated for 15 minutes at room temperature before addition of 15 µl of substrate from the kit (250 nM final concentration) and incubated for additional 90 minutes at room temperature. The assay plate was subsequently read in a Pherastar (Ex540/Em590). The enzyme activity observed in presence of test compound were normalized to the enzyme activity observed in presence of buffer and 10 µM (final concentration) of the high affinity BACE1 reference inhibitor (S)-6-[3-Chloro-5-(5-prop-1-ynyl-pyridin-3-yl)-thiophen-2-yl]-2-imino-3,6-dimethyl-tetrahydropyrimidin-4-one, respectively. The efficacy of the test compounds was evaluated at 10 µM (final concentration) and defined as the percent inhibition of the enzyme activity using the equation % inhibition=100%—normalized enzyme activity in percent.

TABLE 2

BACE1 activity of selected compounds

| Compound No | BACE1 inhibition at 10 µM (%) |
|---|---|
| 1 | 106 |
| 2 | 104 |
| 3 | 105 |
| 4 | 102 |
| 5 | 103 |
| 6 | 106 |
| 7 | 104 |
| 9 | 103 |
| 10 | 103 |
| 11 | 103 |
| 12 | 103 |
| 13 | 100 |
| 14 | 103 |
| 15 | 104 |
| 16 | 104 |
| 17 | 104 |
| 18 | 103 |
| 19 | 104 |
| 20 | 102 |

Assessment of Aβ Levels in Rat Brain and Plasma Following BACE1 Inhibition.

Animals.

All rat care and experimental procedures were approved by Lundbeck Veterinary Staff, according to Danish legislature. The rats were maintained in a barrier facility with a 12/12-h light/dark cycle and ad libitum food and water access.

Treatment of Naïve Rats.

Young adult Male Sprague Dawley rats of approximately 250 g weight were purchased from Charles River and received 0-30 mg/kg of vehicle (10% HP betaCD+1M MeSO$_4$, pH 2.5) or test compounds (dissolved in vehicle) only by oral gavage (p.o). The compounds are dosed at a volume of 5 ml/kg. Cohorts of 5-10 animals were established for each treatment condition.

The animals undergoing treatment were closely monitored by veterinary staff for any signs of toxicity. Monitoring parameters included body weight, physical appearance, changes in coat appearance, occurrence of unprovoked behavior, and blunted or exaggerated responses to external stimuli.

Tissue Collection.

At T=180 minutes after initial dosing the animals were stunned and decapitated with a guillotine. Trunk-blood was sampled in EDTA coated tubes after decapitation of the animal. The blood was centrifuged at 2200 G at 4° C. for 15 minutes and the plasma was collected and frozen at −80° C. The blood was aliquoted for Aβ ELISA and pharmacokinetic analysis. Immediately following sacrifice, the brain was extracted and split into 2 halves. The right hemibrains were snap frozen on dry ice and stored at −80° C. The left half was dissected; with the front forebrain taken for Aβ ELISA and the remainder used for DMPK analysis. These samples were also snap frozen on dry ice and stored at −80° C. until use for analysis.

Tissue Processing.

The cortex samples were thawed slightly on wet ice before they were homogenized with a small volume dispersing instrument (T10 basic ULTRA-TURRAX®) which was set at speed 5 for approximately 5-7 sec. The tissue was processed in a 10 times volume of the weight, for example 100 mg of tissue was homogenized in 1000 µL of Homogenization buffer. Homogenization buffer: 50 ml Milli Q water+50 nM NaCl+0.2% Diethylamin (DEA)+1 tablet of Complete Protease inhibitor cocktail+1 nM 4-(2-aminoethyl) benzenesulfonyl fluoride hydrochloride irreversible serine protease inhibitor (AEBSF).

After homogenization 450 µL aliquots of the samples were collected into a 1.5 ml Eppendorf tube and placed on wet ice, 0.5% NP-40 (50 ul) was added to all samples and then they were incubated on ice for 30 min. After which all samples were sonicated using an Ultrasonic homogenizer with 20 kHz homogeneous sound (SONOPLUS HD2070, Bandelin Electronic) 10 pulse set at 12-13% power to extract all the Aβ species. The samples were then centrifuged (Ole Dich 157 MPRF Micro centrifuge) at 20000 G for 20 minutes at 4° C. After centrifugation 285 µL of the supernatant was pipetted into 600 µL microtubes tubes and neutralized with 15 µL of 1M Tris-HCL buffer.

ELISA Protocol.

WAKO 294-62501 Human/Rat Abeta amyloid (40) kit was used for all ELISA analyses. 30 µL plasma samples or 30 µL of the cortex supernatants generated as described above were placed in 600 µL microtubes tubes on wet ice. To this 30 µL of 8M urea (AppliChem A1049, 9025) was added to generate a 2-fold dilution. Both plasma and cortex supernatants were incubated on ice for 30 min. Standard rows were prepared from the standard peptide stock provided in the kit and standard diluent containing 1.6M Urea (200 µL 8M urea+800 µL of standard diluent) and 0.8M urea (400 µL 8M urea+3600 µL Standard diluent). A serial 2-fold dilution of Aβ40 from 100 µmol/ml to 0 pmol/L was prepared for the assay.

After incubation with urea, all samples were further diluted by addition of 5 times standard diluent from the Kit. This was done by adding 240 µL Standard Diluent to 60 µL sample/urea mixture, which was then mixed well. 100 µL of each diluted sample was pipetted into designated wells of the ELISA plate in duplicates. The plate was then covered and incubated overnight at 4° C. The following day, the ELISA kit was brought to room temperature before use. The incubated plate was washed 5 times with the 20× washing solution diluted in Milli Q water. 100 µL HRP-conjugate was applied to each well, and the plate was covered and incubates at 4° C. for 1 hr. The wash was repeated again for 5 times. 100 µL 3,3',5,5'-Tetramethylbenzidine (TMB) solution was applied to each well and the plate was covered and incubated in the dark at room temperature for 30 minutes. 100 µL STOP-solution was next applied to each well, and the plate was read at 450 nm wavelength in a spectrophotometer (Labsystems Multiscan Ascent) within 30 min of adding the STOP-solution to the wells.

Concentration of Aβ in the samples was determined based on a standard curve generated from standards containing known concentrations of synthetic Aβ40. Those skilled in the art will appreciate that diethylamine (DEA) and urea extractions will release soluble Aβ, and insoluble Aβ respectively. Since the ELISA kit is validated and widely used, it is accepted that as long as the treatment conditions and assay conditions are the same for each compound tested, then the assay should yield consistent robust data for the compounds tested and produce minimal discrepancies.

Data Analysis

To determine the concentration of Aβ40 in the samples, the interpolated values of the samples loaded on plates are multiplied by 20 to account for the dilutions made when the volumes of DEA, urea and neutralization solution were added up. Values are calculated as percentage change in Aβ40 compared to vehicle treated animals.

Bioanalysis of Brain and Plasma Samples

TC (test compound) was determined in plasma and brain homogenate using UltraPerformance LC® (U PLC®) chromatography followed by tandem-MS (MS/MS) detection.

Apparatus:

Tecan Genesis RSP 200; Biomek NXP, Beckman Coulter; Sigma 4K15 centrifuge; Acquity UPLC, Waters; Sciex API4000 TQ, Applied Biosystems; MS software: Analyst version 1.4.1

Chemicals

Acetonitrile, HPLC-grade, Fluke, No. 34967N; Methanol, HPLC-grade, Sigma-Aldrich, Lot 9003S; Formic acid, HPLC-grade, Riedel-de Haen, Lot 51660; Purified water, Millipore Synergy UV Sample Preparation Brain homogenate was prepared by homogenizing the brain 1:4 (v/v) with water:2-propanol:DMSO (50:30:20 v/v/v) followed by centrifugation and collection of the supernatant. Calibration standards and QC samples were prepared using a Hamilton robot. 150 µL of ISTD in acetonitrile (1 ng/mL ISTD) was added to 25 µL of calibration standards, QC samples and test samples (plasma and brain homogenate) using a Biomek robot. After centrifugation (6200 g, 4° C., 20 min) 100 µL supernatant from each sample was transferred to a new plate and mixed with 100 µL water with 0.1% formic acid using a Biomek robot (method file InVivo transfer). After a quick centrifugation (6200 g, 4° C., 5 min) the samples were placed in the auto-sampler.

UPLC-MS/MS Analysis

MS/MS detection was done with an Applied Biosystems Sciex API 4000 instrument in positive-ion electrospray ionisation mode. TC and ISDD were detected at a parent>daughter mass to charge ratio (m/z). Nitrogen was used for the nebulizer and collision gases. The peak area correlated linearly with the plasma and brain concentration of the analytes in the range of 1.00-1000 ng/mL plasma and 5.00-5000 ng/g brain (corrected for dilution). If the plasma/brain sample drug concentration was above 1000 ng/mL or 5000 ng/g, the sample was diluted appropriately in blank plasma/blank brain homogenate before analysis.

Chromatographic System

Analytical columns:

Waters Acquity UPLC HSS C18 SB (pH 2-8) 1.8 µm, 2.1×30 mm.

Mobile phase A: 0.1% aq. formic acid or 0.1% aq. ammonium hydroxide

Mobile phase B: Acetonitrile with 0.1% aq. formic acid or 0.1% aq. ammonium hydroxide.

Weak wash: Methanol

Strong wash: Acetonitrile/Isopropanol/formic acid (50/50/2 v/v/v)

Flow: 0.6 mL/min

Run time: 3 min.

To waste: 0-0.5 min

Temperature: 40° C.

Gradient:

| Time (min) | % A | % B |
| --- | --- | --- |
| 0 | 98 | 2 |
| 0.01 | 98 | 2 |
| 1.5 | 5 | 95 |
| 2 | 5 | 95 |
| 2.2 | 98 | 2 |
| 3 | 98 | 2 |

Compound 1 was administered at doses of 10 mg/kg p.o. and 30 mg/kg p.o. and brain and plasma samples were collected at 3 hours post dose and the following exposures were measured as described above.

TABLE 3

Results for compound 11

|  | Dose (mg/kg) | Exp (ng/g) | Brain/Plasma ratio | Aβ40 reduction (%) |
|---|---|---|---|---|
| Brain Rat | 10 | 416 | 2.1 | 21 |
| Plasma Rat |  | 195 |  | 39 |
| Brain Rat | 30 | 1352 | 2.3 | 41 |
| Plasma Rat |  | 590 |  | 60 |

TABLE 4

Results for compound 13

|  | Dose (mg/kg) | Exp (ng/g) | Brain/Plasma ratio | Aβ40 reduction (%) |
|---|---|---|---|---|
| Brain Rat | 10 | 588 | 1.25 | 43 |
| Plasma Rat |  | 469 |  | 38 |
| Brain Rat | 30 | 1592 | 1.59 | 59 |
| Plasma Rat |  | 1000 |  | 38 |

TABLE 5

Results for compound 5

|  | Dose (mg/kg) | Exp (ng/g) | Brain/Plasma ratio | Aβ40 reduction (%) |
|---|---|---|---|---|
| Brain Rat | 10 | 536 | 1.95 | 56 |
| Plasma Rat |  | 275 |  | 44 |
| Brain Rat | 30 | 1606 | 2.74 | 65 |
| Plasma Rat |  | 587 |  | 46 |

As shown in table 3, table 4, and table 5 compounds of the present invention are able to penetrate the blood brain barrier and show efficacy in the CNS.

MDCK-MDR1 Assay

The permeability of the test compounds was assessed in MDCK-MDR1 cells that were cultured to confluency (4-6 days) in a 96 transwell plate. Test compounds were diluted with the transport buffer (HBSS+1% BSA) to a concentration of 0.5 µM and applied to the apical or basolateral side of the cell monolayer. Permeation of the test compounds from A to B direction or B to A direction was determined in triplicate over a 60-minute incubation time at 37° C. and 5% CO2 with a relative humidity of 95%. Test compounds were quantified by LC-MS/MS analysis based on the peaks area ratios of analyte/IS in both the receiver and donor wells of the transwell plate.

The apparent permeability coefficient Papp (cm/s) was calculated using the equation:

$$Papp = (dCr/dt) \times Vr/(A \times C0)$$

Where dCr/dt is the cumulative concentration of compound in the receiver chamber as a function of time (µM/s); Vr is the solution volume in the receiver chamber (0.05 mL on the apical side; 0.25 mL on the basolateral side); A is the surface area for the transport, i.e. 0.0804 cm² for the area of the monolayer; C0 is the initial concentration in the donor chamber (µM).

Compounds are classified Pgp substrates when efflux ratio (Papp BA/Papp AB) is ≥2.

TABLE 6

Efflux ratio of selected compounds

| Compound | MDCK-MDR1 efflux ratio |
|---|---|
| 1 | 0.89 |
| 2 | 2.32 |
| 3 | 4.87 |
| 4 | 1.34 |
| 5 | 1.07 |
| 6 | 7 |
| 8 | 2.36 |
| 9 | 8.61 |
| 10 | 10.6 |
| 11 | 1.89 |
| 13 | 1.5 |
| 14 | 1.06 |
| 15 | 1.17 |
| 16 | 1 |
| 17 | 0.95 |
| 19 | 1.18 |
| 20 | 0.77 |
| 21 | 0.97 |
| 22 | 1.08 |
| 23 | 1.06 |
| 24 | 0.88 |
| 25 | 1.09 |
| 26 | 0.92 |

As shown in tables 4, the majority of the exemplified compounds of the present invention have MDCK- MDR1 efflux ratios below 2 and are thus likely to be able to cross the blood brain barrier (E Kerns, L Di, Drug-like Properties: Concepts, Structure Design and Methods (2008) Elsevier).

The invention claimed is:

1. A compound of Formula I:

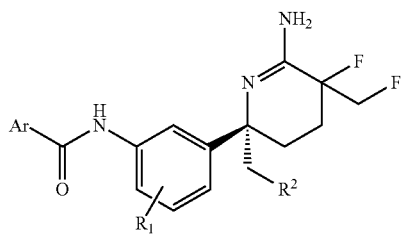

wherein:

Ar is: (1) selected from the group consisting of phenyl, pyridyl, pyrimidyl, pyrazinyl, imidazolyl, pyrazolyl, thiazolyl, oxazolyl, isoxazolyl; and (2) optionally substituted with one or more substituents selected from the group consisting of halogen, CN, $C_1$-$C_6$ alkyl, $C_2$-$C_6$ alkenyl, $C_2$-$C_6$ alkynyl, $C_1$-$C_6$ fluoroalkyl and $C_1$-$C_6$ alkoxy;

$R^1$ is one or more hydrogen, halogen, $C_1$-$C_3$ fluoroalkyl or $C_1$-$C_3$ alkyl; and $R^2$ is hydrogen or fluoro;

or a pharmaceutically acceptable salt thereof.

2. The compound or pharmaceutically acceptable salt thereof according to claim 1, wherein Formula I is Formula Ia or Ib:

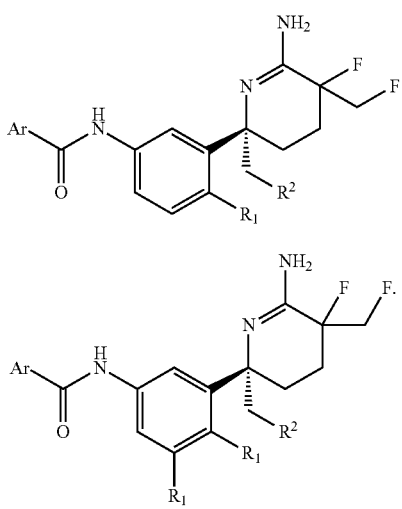

3. The compound or the pharmaceutically acceptable salt thereof according to claim 1, wherein R¹ is halogen.

4. The compound or the pharmaceutically acceptable salt thereof according to claim 1, wherein R¹ is fluoro.

5. The compound or the pharmaceutically acceptable salt thereof according to claim 1, wherein R² is hydrogen.

6. The compound or the pharmaceutically acceptable salt thereof according to claim 1, wherein R² is fluoro.

7. The compound or the pharmaceutically acceptable salt thereof according to claim 1, wherein Ar is pyridyl.

8. The compound or the pharmaceutically acceptable salt thereof according to claim 1, wherein Ar is pyrimidyl.

9. The compound or the pharmaceutically acceptable salt thereof according to claim 1, wherein Ar is pyrazinyl.

10. The compound or the pharmaceutically acceptable salt thereof according to claim 1, wherein Ar is oxazolyl.

11. The compound or the pharmaceutically acceptable salt thereof according to claim 1, wherein Ar is imidazolyl.

12. The compound or the pharmaceutically acceptable salt thereof according to claim 1, wherein Ar is thiazolyl.

13. The compound or the pharmaceutically acceptable salt thereof according to claim 1, wherein Ar is pyrazolyl.

14. The compound or the pharmaceutically acceptable salt thereof according to claim 1, wherein Ar is isoxazolyl.

15. The compound or the pharmaceutically acceptable salt thereof according to claim 1, wherein Ar is phenyl.

16. The compound according to claim 1, wherein Ar is substituted by one or more substituents selected from the group consisting of: F, Cl, Br, CN, $C_1$-$C_3$ alkyl, $C_1$-$C_3$ fluoroalkyl and $C_1$-$C_3$ alkoxy.

17. A compound, a pharmaceutically acceptable salt thereof, wherein said compound is selected from the group consisting of:

(1) N-(3-((2S,5S)-6-amino-5-fluoro-5-(fluoromethyl)-2-methyl-2,3,4,5-tetrahydropyridin-2-yl)-4-fluorophenyl)-5-methoxypicolinamide;

(3) N-(3-((2S,5S)-6-amino-5-fluoro-5-(fluoromethyl)-2-methyl-2,3,4,5-tetrahydropyridin-2-yl)-4-fluorophenyl)-5-cyano-3-methylpicolinamide;

(4) N-(3-((2S,5S)-6-amino-5-fluoro-5-(fluoromethyl)-2-methyl-2,3,4,5-tetrahydropyridin-2-yl)-4-fluorophenyl)-5-chloropicolinamide;

(5) N-(3-((2S,5S)-6-amino-5-fluoro-5-(fluoromethyl)-2-methyl-2,3,4,5-tetrahydropyridin-2-yl)-4-fluorophenyl)-5-methoxypyrazine-2-carboxamide;

(6) N-(3-((2S,5S)-6-amino-5-fluoro-5-(fluoromethyl)-2-methyl-2,3,4,5-tetrahydropyridin-2-yl)-4-fluorophenyl)-2-methyloxazole-4-carboxamide;

(7) N-(3-((2S,5S)-6-amino-5-fluoro-5-(fluoromethyl)-2-methyl-2,3,4,5-tetrahydropyridin-2-yl)-4-fluorophenyl)-4-bromo-1-methyl-1H-imidazole-2-carboxamide;

(8) N-(3-((2S,5S)-6-amino-5-fluoro-5-(fluoromethyl)-2-methyl-2,3,4,5-tetrahydropyridin-2-yl)-4-fluorophenyl)-4-methylthiazole-2-carboxamide;

(9) N-(3-((2S,5S)-6-amino-5-fluoro-5-(fluoromethyl)-2-methyl-2,3,4,5-tetrahydropyridin-2-yl)-4-fluorophenyl)-2-(difluoromethyl)oxazole-4-carboxamide;

(10) N-(3-((2S,5S)-6-amino-5-fluoro-5-(fluoromethyl)-2-methyl-2,3,4,5-tetrahydropyridin-2-yl)-4-fluorophenyl)-1-(difluoromethyl)-1H-pyrazole-3-carboxamide;

(11) N-(3-((2S,5S)-6-amino-5-fluoro-5-(fluoromethyl)-2-methyl-2,3,4,5-tetrahydropyridin-2-yl)-4-fluorophenyl)-5-(difluoromethyl)pyrazine-2-carboxamide;

(12) N-(3-((2S,5S)-6-amino-5-fluoro-5-(fluoromethyl)-2-methyl-2,3,4,5-tetrahydropyridin-2-yl)-4-fluorophenyl)-4-chlorobenzamide;

(13) N-(3-((2S,5S)-6-amino-5-fluoro-5-(fluoromethyl)-2-methyl-2,3,4,5-tetrahydropyridin-2-yl)-4-fluorophenyl)-5-fluoropicolinamide;

(14) N-(3-((2S,5R)-6-amino-5-fluoro-5-(fluoromethyl)-2-methyl-2,3,4,5-tetrahydropyridin-2-yl)-4-fluorophenyl)-5-methoxypicolinamide;

(15) N-[3-[(2S,5S)-6-amino-5-fluoro-5-(fluoromethyl)-2-methyl-2,3,4,5-tetrahydropyridin-2-yl]-4,5-difluorophenyl]-5-fluoro-pyridine-2-carboxamide;

(16) N-[3-[(2S,5S)-6-amino-5-fluoro-5-(fluoromethyl)-2-methyl-2,3,4,5-tetrahydropyridin-2-yl]-4,5-difluorophenyl]-5-methoxy-pyridine-2-carboxamide;

(17) N-[3-[(2S,5S)-6-amino-5-fluoro-5-(fluoromethyl)-2-methyl-2,3,4,5-tetrahydropyridin-2-yl]-4,5-difluorophenyl]-5-methoxy-pyrazine-2-carboxamide;

(18) N-[3-[(2S,5R)-6-amino-5-fluoro-5-(fluoromethyl)-2-methyl-2,3,4,5-tetrahydropyridin-2-yl]-4,5-difluorophenyl]-5-fluoro-pyridine-2-carboxamide;

(19) N-[3-[(2S,5R)-6-amino-5-fluoro-5-(fluoromethyl)-2-methyl-2,3,4,5-tetrahydropyridin-2-yl]-4,5-difluorophenyl]-5-methoxy-pyridine-2-carboxamide;

(20) N-[3-[(2S,5R)-6-amino-5-fluoro-5-(fluoromethyl)-2-methyl-2,3,4,5-tetrahydropyridin-2-yl]-4,5-difluorophenyl]-5-methoxy-pyrazine-2-carboxamide;

(21) N-[3-[(2S,5S)-6-amino-5-fluoro-2,5-bis(fluoromethyl)-2,3,4,5-tetrahydropyridin-2-yl]-4-fluoro-phenyl]-5-fluoro-pyridine-2-carboxamide;

(22) N-[3-[(2S,5S)-6-amino-5-fluoro-2,5-bis(fluoromethyl)-2,3,4,5-tetrahydropyridin-2-yl]-4-fluoro-phenyl]-5-methoxy-pyridine-2-carboxamide;

(23) N-[3-[(2S,5S)-6-amino-5-fluoro-2,5-bis(fluoromethyl)-2,3,4,5-tetrahydropyridin-2-yl]-4-fluoro-phenyl]-5-methoxy-pyrazine-2-carboxamide;

(24) N-[3-[(2S,5R)-6-amino-5-fluoro-2,5-bis(fluoromethyl)-2,3,4,5-tetrahydropyridin-2-yl]-4-fluoro-phenyl]-5-fluoro-pyridine-2-carboxamide;

(25) N-[3-[(2S,5R)-6-amino-5-fluoro-2,5-bis(fluoromethyl)-2,3,4,5-tetrahydropyridin-2-yl]-4-fluoro-phenyl]-5-methoxy-pyridine-2-carboxamide; and

(26) N-[3-[(2S,5R)-6-amino-5-fluoro-2,5-bis(fluoromethyl)-2,3,4,5-tetrahydropyridin-2-yl]-4-fluoro-phenyl]-5-methoxy-pyrazine-2-carboxamide.

18. A pharmaceutical composition comprising the compound or pharmaceutically acceptable salt thereof according to claim 1, and a pharmaceutically acceptable carrier.

19. A method of treating a disease selected from the group consisting of:
   (A) familial Alzheimer's disease; and
   (B) sporadic Alzheimer's disease;
   the method comprising the administration of a therapeutically effective amount of a compound, or pharmaceutically acceptable salt thereof, according to claim 1 to a patient in need thereof.

20. A compound, or a pharmaceutically acceptable salt thereof, wherein said compound is selected from the group consisting of:
   (1) (6S)-3-Fluoro-3-(fluoromethyl)-6-(2-fluorophenyl)-6-methylpiperidin-2-one;
   (2) (6S)-6-(2,3-Difluorophenyl)-3-fluoro-3-(fluoromethyl)-6-methylpiperidin-2-one; and
   (3) (6S)-3-Fluoro-3,6-bis(fluoromethyl)-6-(2-fluorophenyl)piperidin-2-one.

21. A compound, or a pharmaceutically acceptable salt thereof, wherein said compound is selected from the group consisting of:
   (1) (3S,6S)-3-fluoro-6-(2-fluoro-5-nitrophenyl)-3-(fluoromethyl)-6-methylpiperidin-2-one;
   (2) (3R,6S)-3-fluoro-6-(2-fluoro-5-nitrophenyl)-3-(fluoromethyl)-6-methylpiperidin-2-one;
   (3) (3S,6S)-6-(2,3-Difluoro-5-nitrophenyl)-3-fluoro-3-(fluoromethyl)-6-methylpiperidin-2-one;
   (4) (3R,6S)-6-(2,3-difluoro-5-nitrophenyl)-3-fluoro-3-(fluoromethyl)-6-methylpiperidin-2-one; and
   (5) (6S)-3-Fluoro-6-(2-fluoro-5-nitrophenyl)-3,6-bis(fluoromethyl)piperidin-2-one.

22. A compound, or a pharmaceutically acceptable salt thereof, wherein said compound is selected from the group consisting of:
   (1) (3S,6S)-3-Fluoro-3-(fluoromethyl)-6-(2-fluoro-5-nitro-phenyl)-6-methylpiperidin-2-thione;
   (2) (3R, 6S)-3-Fluoro-3-(fluoromethyl)-6-(2-fluoro-5-nitro-phenyl)-6-methylpiperidin-2-thione;
   (3) (3S,6S)-6-(2,3-Difluoro-5-nitrophenyl)-3-fluoro-3-(fluoromethyl)-6-methylpiperidin-2-thione;
   (4) (3R,6S)-6-(2,3-difluoro-5-nitrophenyl)-3-fluoro-3-(fluoromethyl)-6-methylpiperidin-2-thione; and
   (5) (6S)-3-Fluoro-6-(2-fluoro-5-nitrophenyl)-3,6-bis(fluoromethyl)piperidin-2-thione.

23. A compound, or a pharmaceutically acceptable salt thereof, wherein said compound is selected from the group consisting of:

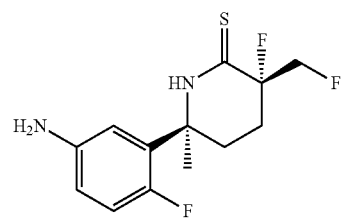

(3S,6S)-6-(5-amino-2-fluorophenyl)-3-fluoro-3-(fluoromethyl)-6-methylpiperidine-2-thione;

(1)

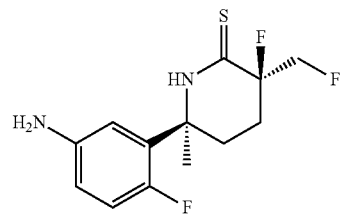

(3R,6S)-6-(5-amino-2-fluorophenyl)-3-fluoro-3-(fluoromethyl)-6-methylpiperidine-2-thione;

(2)

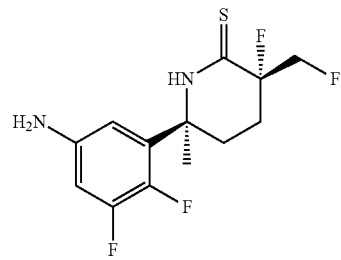

(3S,6S)-6-(5-amino-2,2-difluorophenyl)-3-fluoro-3-(fluoromethyl)-6-methylpiperidine-2-thione;

(3)

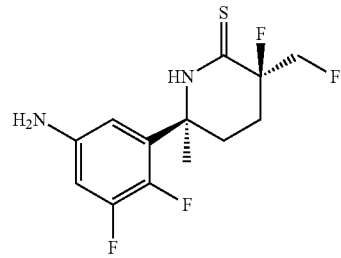

(3R,6S)-6-(5-amino-2,3-difluorophenyl)-3-fluoro-3-(fluoromethyl)-6-methylpiperidine-2-thione; and (4)

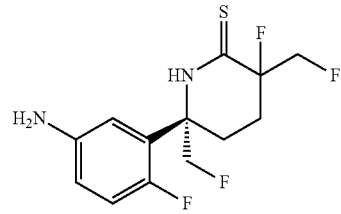

(6S)-6-(5-amino-2-fluorophenyl)-3-fluoro-3,6-bis(fluoromethyl)piperidine-2-thione.

(5)

24. A method of treating a disease selected from the group consisting of:
   (A) preclinical Alzheimer's disease; and
   (B) prodromal Alzheimer's disease;
   the method comprising the administration of a therapeutically effective amount of a compound, or pharmaceutically acceptable salt thereof, according to claim 1 to a patient in need thereof.

25. A method of treating mild cognitive impairment which comprises the administration of a therapeutically effective amount of a compound, or pharmaceutically acceptable salt thereof, according to claim 1 to a patient in need thereof.

26. A method of treating a disease selected from the group consisting of:
   (A) Down's syndrome; and
   (B) cerebral amyloid angiopathy;
   the method comprising the administration of a therapeutically effective amount of a compound, or pharmaceutically acceptable salt thereof, according to claim 1 to a patient in need thereof.

27. A pharmaceutical composition comprising the compound or pharmaceutically acceptable salt thereof according to claim 17, and a pharmaceutically acceptable carrier.

28. A method of treating a disease selected from the group consisting of:
   (A) familial Alzheimer's disease; and
   (B) sporadic Alzheimer's disease;
   the method comprising the administration of a therapeutically effective amount of a compound, or pharmaceutically acceptable salt thereof, according to claim 17 to a patient in need thereof.

29. A method of treating a disease selected from the group consisting of:
   (A) preclinical Alzheimer's disease; and
   (B) prodromal Alzheimer's disease;
   the method comprising the administration of a therapeutically effective amount of a compound, or pharmaceutically acceptable salt thereof, according to claim 17 to a patient in need thereof.

30. A method of treating mild cognitive impairment which comprises the administration of a therapeutically effective amount of a compound, or pharmaceutically acceptable salt thereof, according to claim 17 to a patient in need thereof.

31. A method of treating a disease selected from the group consisting of:
   (A) Down's syndrome; and
   (B) cerebral amyloid angiopathy;
   the method comprising the administration of a therapeutically effective amount of a compound, or pharmaceutically acceptable salt thereof, according to claim 17 to a patient in need thereof.

* * * * *